United States Patent
Yang et al.

(10) Patent No.: US 11,021,438 B2
(45) Date of Patent: Jun. 1, 2021

(54) CURABLE COMPOUND

(71) Applicant: DAICEL CORPORATION, Osaka (JP)

(72) Inventors: Fei Yang, Shanghai (CN); Yoshimichi Okano, Himeji (JP); Kouji Nakatani, Himeji (JP); Feng Liu, Shanghai (CN); Michiyo Nakai, Himeji (JP); Takayuki Yaegashi, Himeji (JP); Yusuke Okamoto, Himeji (JP); Tsukasa Yoshida, Himeji (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 16/470,057

(22) PCT Filed: Nov. 10, 2017

(86) PCT No.: PCT/CN2017/110386
§ 371 (c)(1),
(2) Date: Jun. 14, 2019

(87) PCT Pub. No.: WO2018/107929
PCT Pub. Date: Jun. 21, 2018

(65) Prior Publication Data
US 2020/0079726 A1    Mar. 12, 2020

(30) Foreign Application Priority Data

Dec. 16, 2016  (WO) ................ PCT/CN2016/110302

(51) Int. Cl.
*C07D 207/452*  (2006.01)
*C07D 209/50*  (2006.01)
*C07C 225/22*  (2006.01)

(52) U.S. Cl.
CPC ........ *C07C 225/22* (2013.01); *C07D 207/452* (2013.01); *C07D 209/50* (2013.01)

(58) Field of Classification Search
CPC .. C07D 207/452; C07D 209/50; C07C 225/22
See application file for complete search history.

(56) References Cited

U.S. PATENT DOCUMENTS

| | | | |
|---|---|---|---|
| 4,691,025 A | 9/1987 | Domeier et al. | |
| 5,043,419 A | 8/1991 | Ohta | |
| 6,281,323 B1 | 8/2001 | Yokota et al. | |
| 7,897,715 B1 | 3/2011 | Laskoski et al. | |
| 2019/0119489 A1 | 4/2019 | Nakatani et al. | |
| 2020/0079726 A1 | 3/2020 | Yang et al. | |

FOREIGN PATENT DOCUMENTS

| | | | |
|---|---|---|---|
| JP | 8-333450 A | 12/1996 | |
| JP | 9-12882 A | 1/1997 | |
| JP | 2000-219741 A | 8/2000 | |
| JP | 2000-248252 A | 9/2000 | |
| JP | 2001-323067 A | 11/2001 | |

(Continued)

OTHER PUBLICATIONS

Benicewicz, et al. Document No. 118:39586, retrieved from STN, May 19, 1992.*
Evsyukov, et al. Document No. 161:551457, retrieved from STN, Oct. 2, 2014.*
International Search Report dated Jan. 25, 2018, in PCT/CN2017/110386.
International Search Report dated Sep. 20, 2017, in PCT/CN2018/110302.
Kimura et al., "Synthesis of Thermally Cross-Linkable Fluorine-containing Poly(aryl ether ketone)s I. Phenylethynyl Terminated Poly(aryl ether ketones)s," Polymer Journal (2002), vol. 34, No. 3, pp. 209-218.

(Continued)

*Primary Examiner* — Shawquia Jackson
(74) *Attorney, Agent, or Firm* — Birch, Stewart, Kolasch & Birch, LLP

(57) ABSTRACT

There is provided a curable compound having good solvent solubility and being capable of forming a cured material having super heat resistance. The curable compound according to the present invention is represented by the following formula (1). In the formula (1), $R^1$ and $R^2$ each represent a curable functional group; $D^1$ and $D^2$ each represent a single bond or a linking group; and L represents a divalent group having a repeating unit containing a structure represented by the following formula (I) and a structure represented by the following formula (II) (wherein $Ar^1$ to $Ar^3$ each represent a group made by eliminating two hydrogen atoms from a structural formula of an aromatic ring or a group made by eliminating two hydrogen atoms from a structural formula in which two or more aromatic rings are bound through a single bond or a linking group; X represents —CO—, —S— or —SO$_2$—; each Y represents —S—, —SO$_2$—, —O—, —CO—, —COO— or —CONH—; and n represents an integer of 0 or more):

[Formula 1]

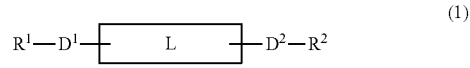

[Formula 2]

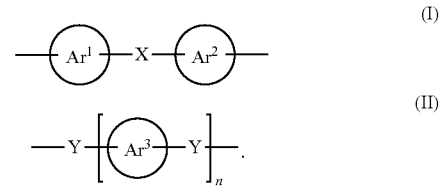

11 Claims, 39 Drawing Sheets

(56) References Cited

FOREIGN PATENT DOCUMENTS

| JP | 2003-213130 A | 7/2003 |
|---|---|---|
| WO | WO 2017/169738 A1 | 10/2017 |
| WO | WO 2018/107453 A1 | 6/2018 |
| WO | WO 2018/107929 A1 | 6/2018 |

OTHER PUBLICATIONS

Lyle et al., "Synthesis, Curing and physical behaviour of maleimide-terminated poly(ether ketones)," Polymer (Jun. 1989), vol. 30, pp. 978-985.

Martinez Nunez, F. and J. de Abajo, "Acetylene-terminated etherketone Oligomers," Polymer (1992), vol. 33, No. 15, pp. 3286-3291.

Qu et al., "Study on Bismaleimide Resin Containing Ether and Ketone Groups Modified by Diallyl Bisphenol A," Engineering Plastics Application (Aug. 2013), vol. 41, No. 8, pp. 83-88.

Written Opinion of the International Searching Authority dated Jan. 26, 2018, in PCT/CN2017/110386.

Written Opinion of the International Searching Authority dated Sep. 20, 2017, in PCT/CN2016/110302.

English translation of International Preliminary Report on Patentability and Written Opinion dated Jun. 27, 2019, in PCT/CN2017/110386 (Forms PCT/IB/326, PCT/IB/373, and PCT/ISA/237).

Extended European Search Report for European Application No. 17881052.9, dated Sep. 3, 2020.

Sundell et al., "Cross-Linking Disulfonated Poly(arylene ether sulfone) Telechelic Oligomers. 1. Synthesis, Characterization, and Membrane Preparation," Industrial & Engineering Chemistry Research, vol. 53, No. 7, Feb. 19, 2014, pp. 2583-2593.

English translation of International Search Report dated Aug. 27, 2019 in PCT/JP2019/022923.

English translation of International Search Report dated Sep. 10, 2019 in PCT/JP2019/022929.

Hedrick et al., "Novel High Temperature Elastomers: Poly(aryl ether ketones)," Polymer Preprints, vol. 31, No. 1, 1990, pp. 444-445.

Hedrick et al., "Elastomeric Behaviour of Crosslinked Poly(aryl ether ketone)s at Elevated Temperatures," Polymer, vol. 33, No. 23, 1992, pp. 5094-5097.

Hedrick et al., "Electromagnetic Processing of Polymers: I. Basic Concepts and Molecular Design of the Macromolecules," Materials Research Society Symposium Proceedings, vol. 189, 1991, pp. 421-430.

Hedrick et al., "Microwave Processing of Functionalized Poly(arylene ether ketones)," Proceedings of the Third International Conference on Polyimides, Ellenville, New York, Nov. 2-4, 1988, pp. 438-442 (Total 7 pages).

Lewis et al., "Microwave Processing of Polymers," Materials Research Society Symposium Proceedings, vol. 124, 1988, pp. 181-188.

Lyle et al., "Synthesis and Characterization of Maleimide Terminated Poly(arylene ether ketone)s," Polyimides: Mater. Chem. Charact., 1989, pp. 213-227.

Lyle et al., "Synthesis, Curing, and Physical Behavior of Maleimide Terminated Poly(arylene ethers)," Polymer Preprints, vol. 29, No. 1, 1988, pp. 346-348.

Wu et al., "Synthesis, Curing and Physical Behavior of Maleimide and Nadimide Terminated Poly(arylene Ether Ketone) Networks," 34th International SAMPE Symposium, vol. 34, May 8-11, 1989, pp. 139-149.

* cited by examiner

[FIG. 1]
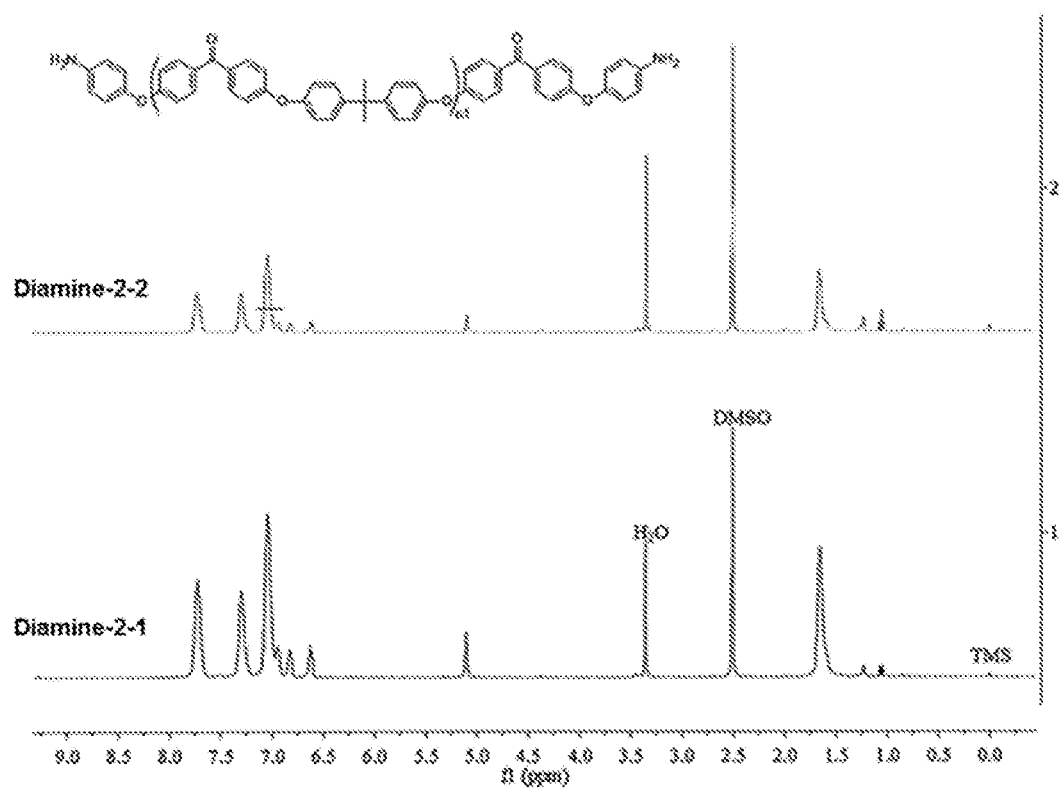

[FIG. 2]
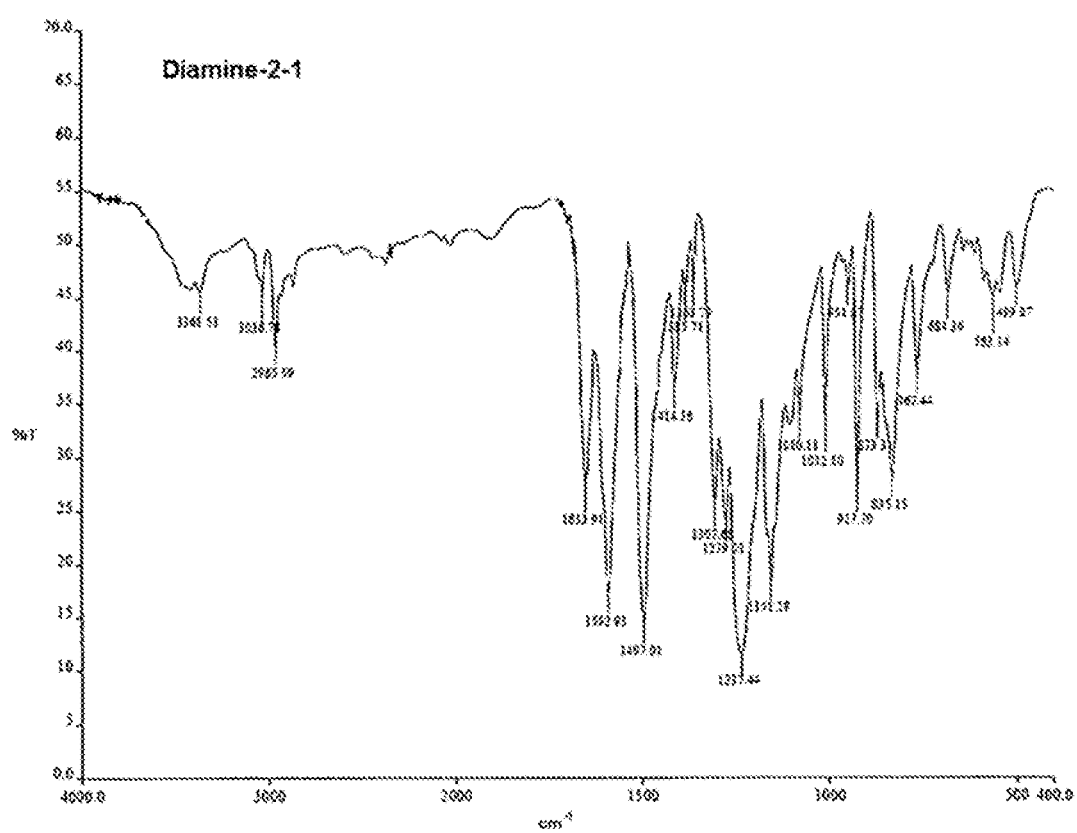

[FIG. 3]
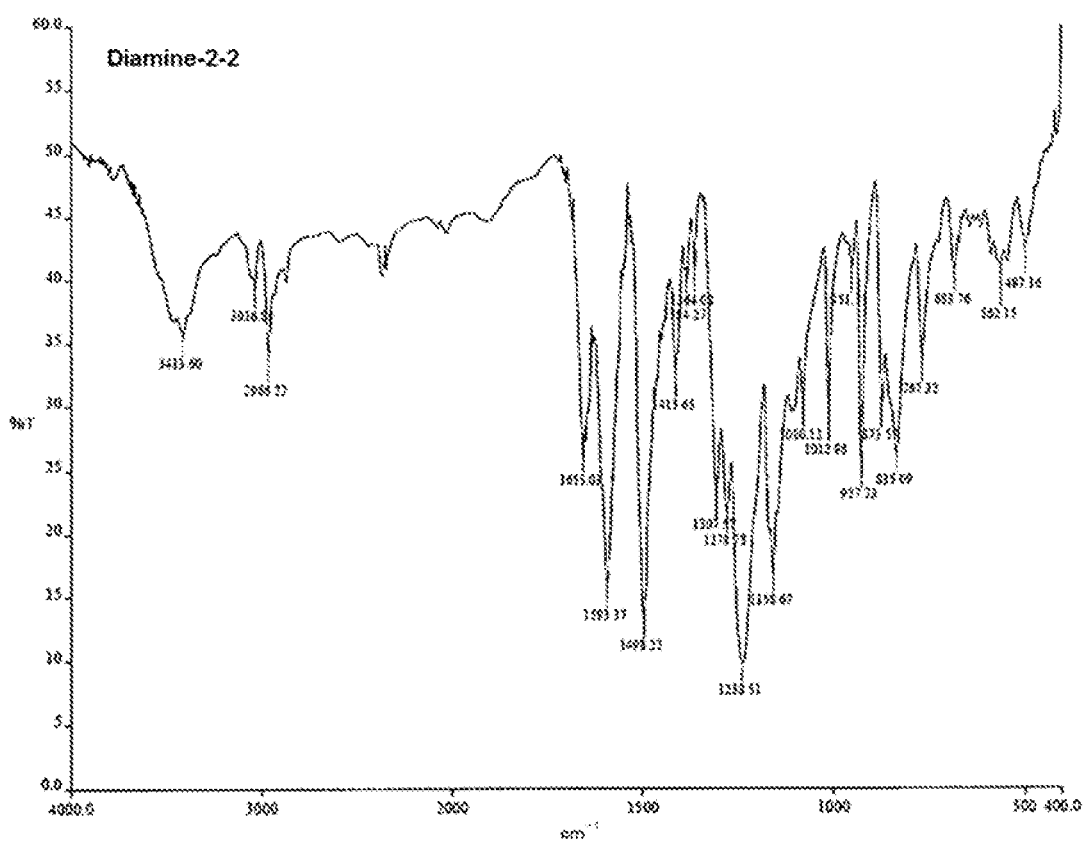

[FIG. 4]
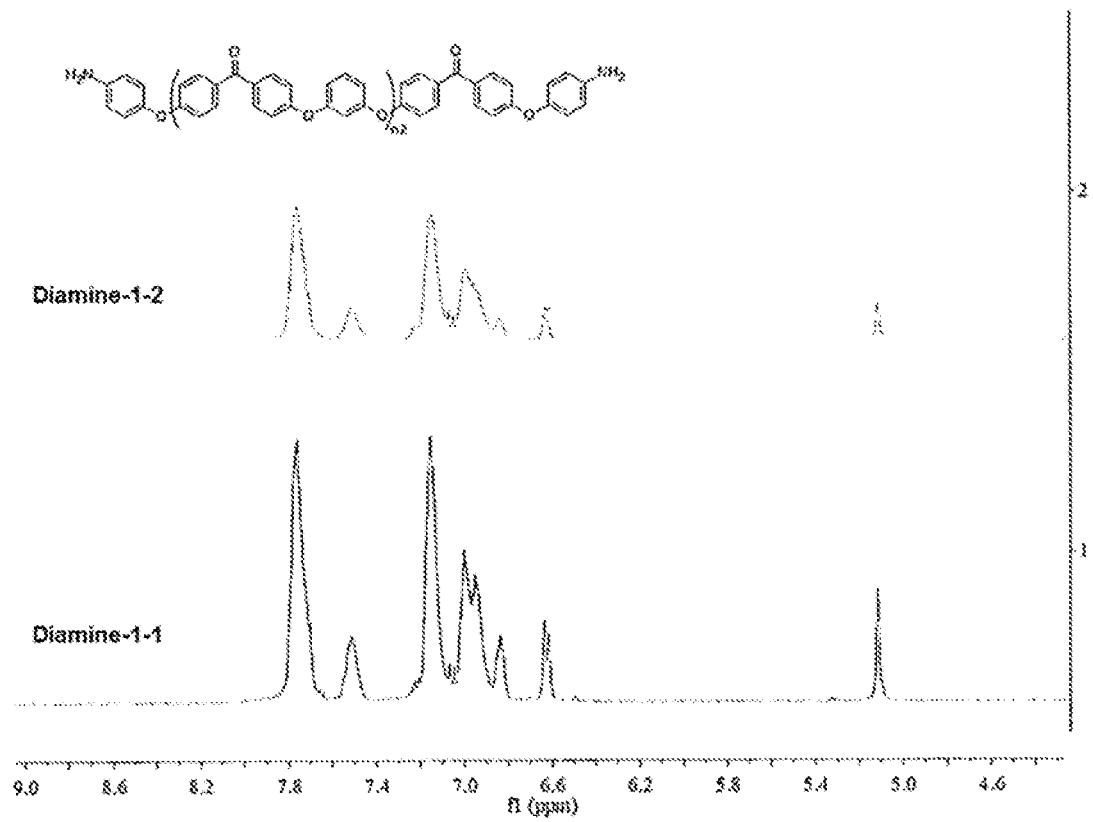

[FIG. 5]
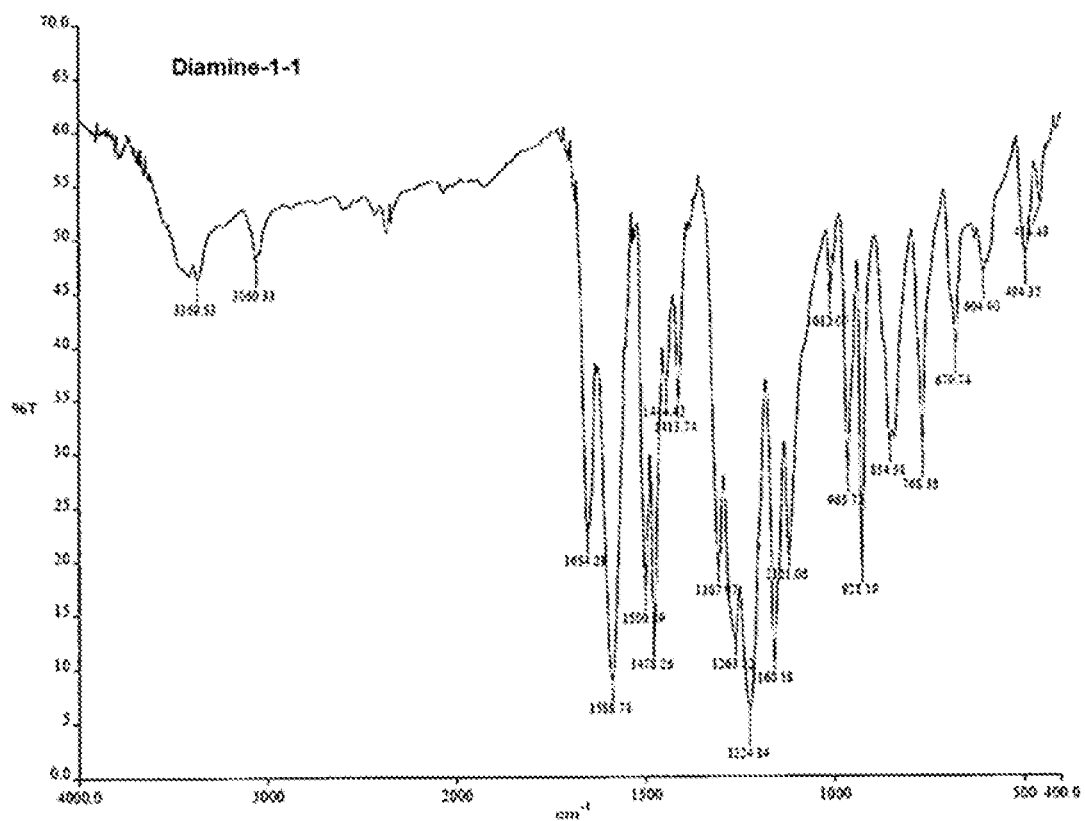

[FIG. 6]
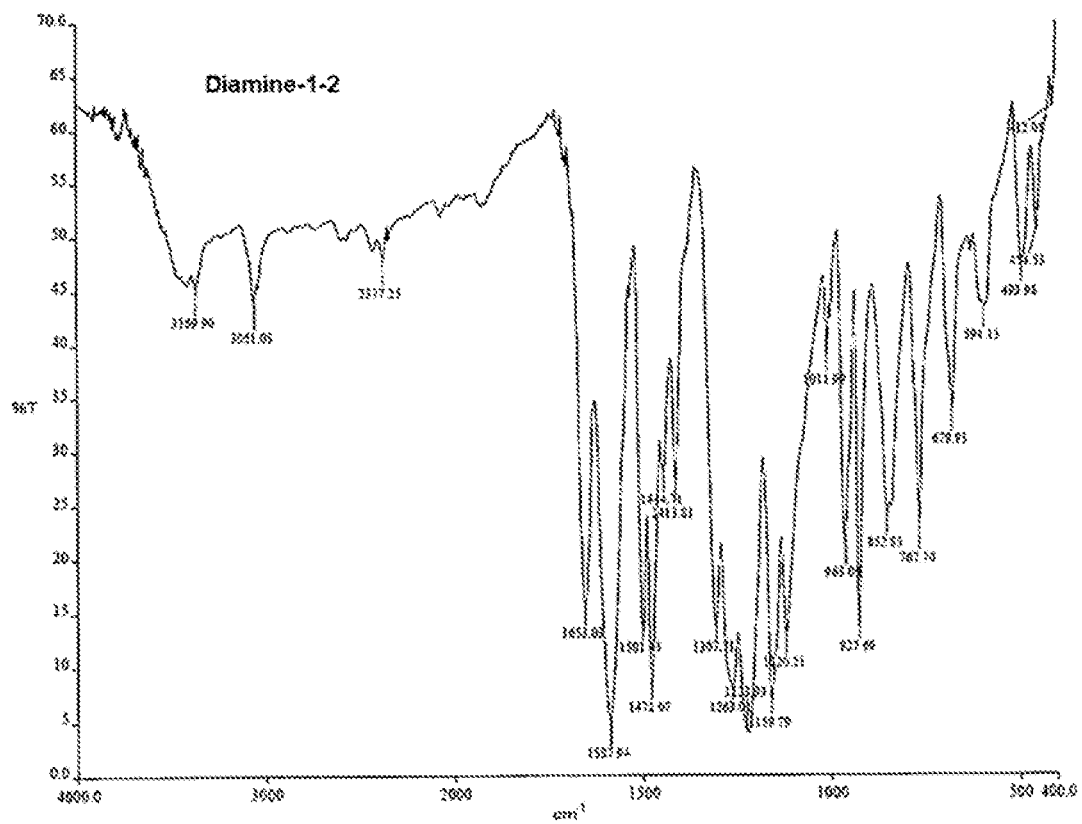

[FIG. 7]
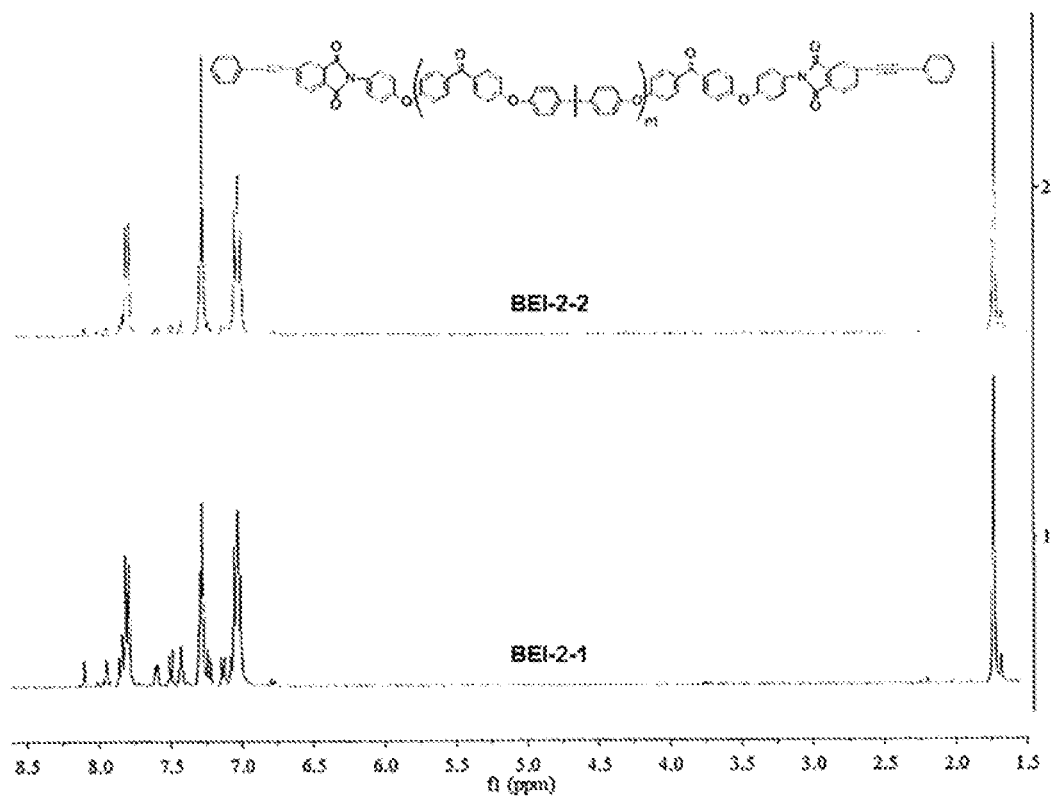

[FIG. 8]
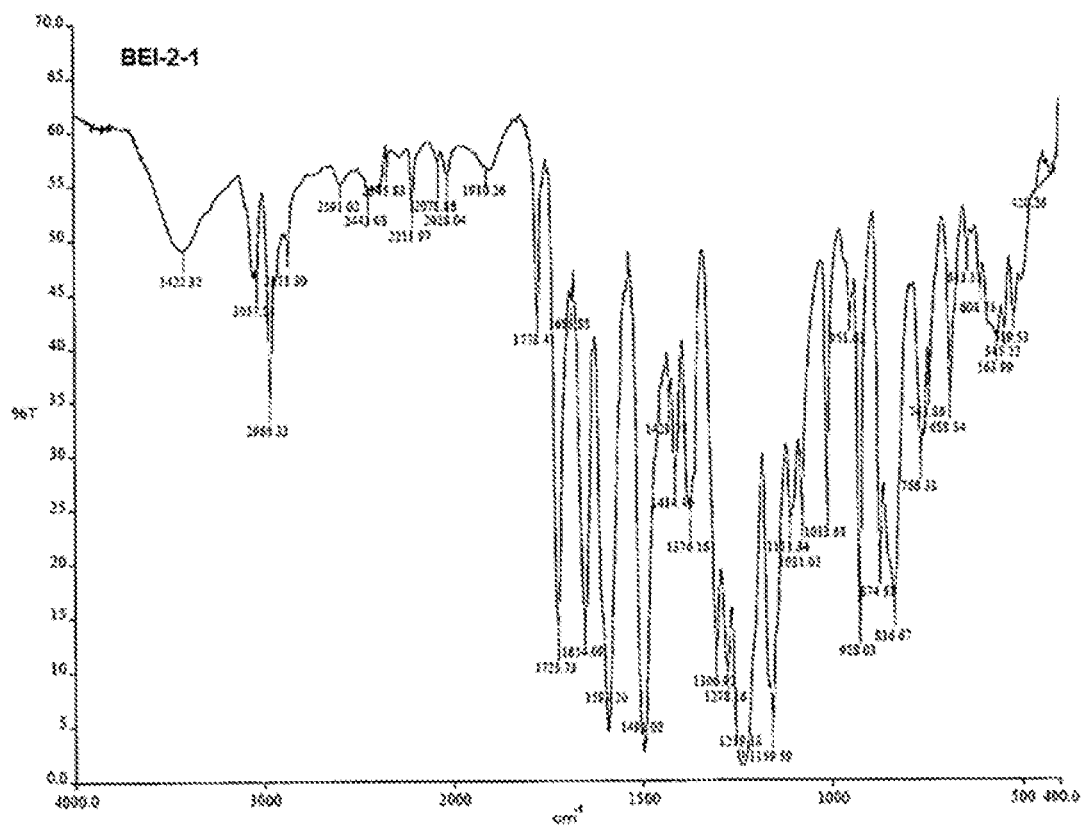

[FIG. 9]
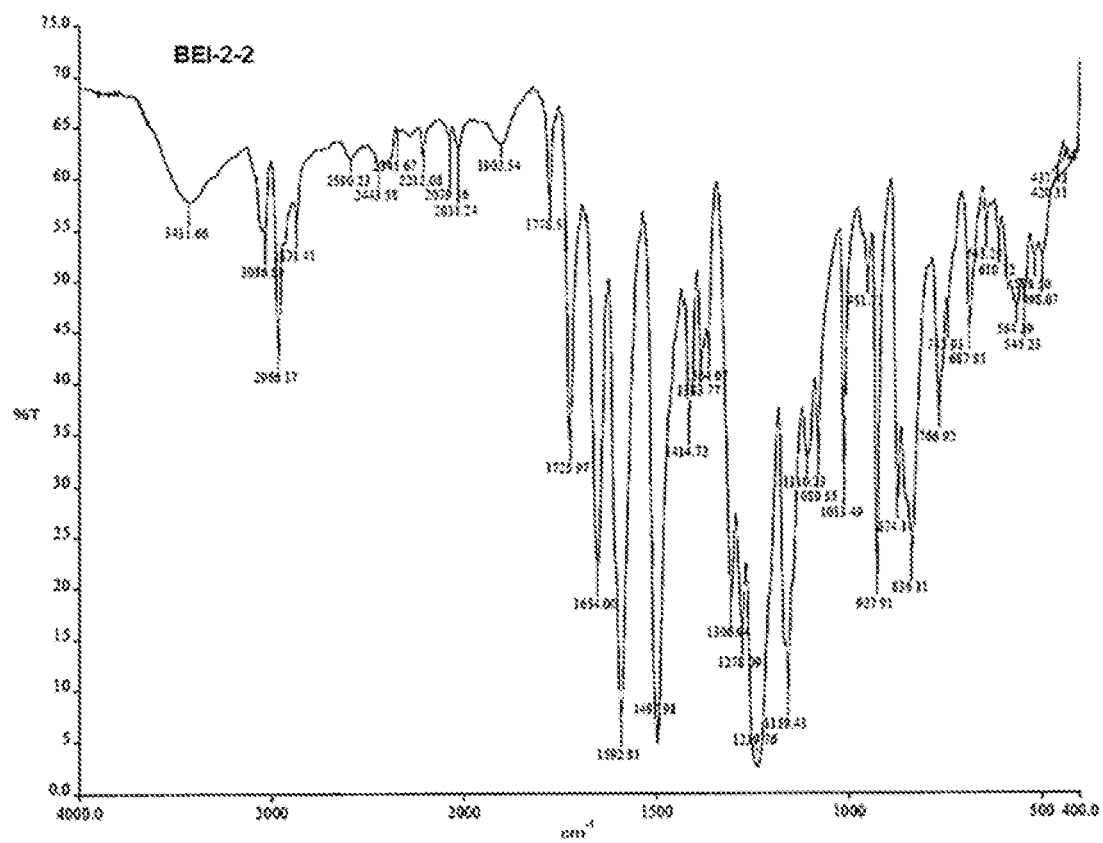

[FIG. 10]
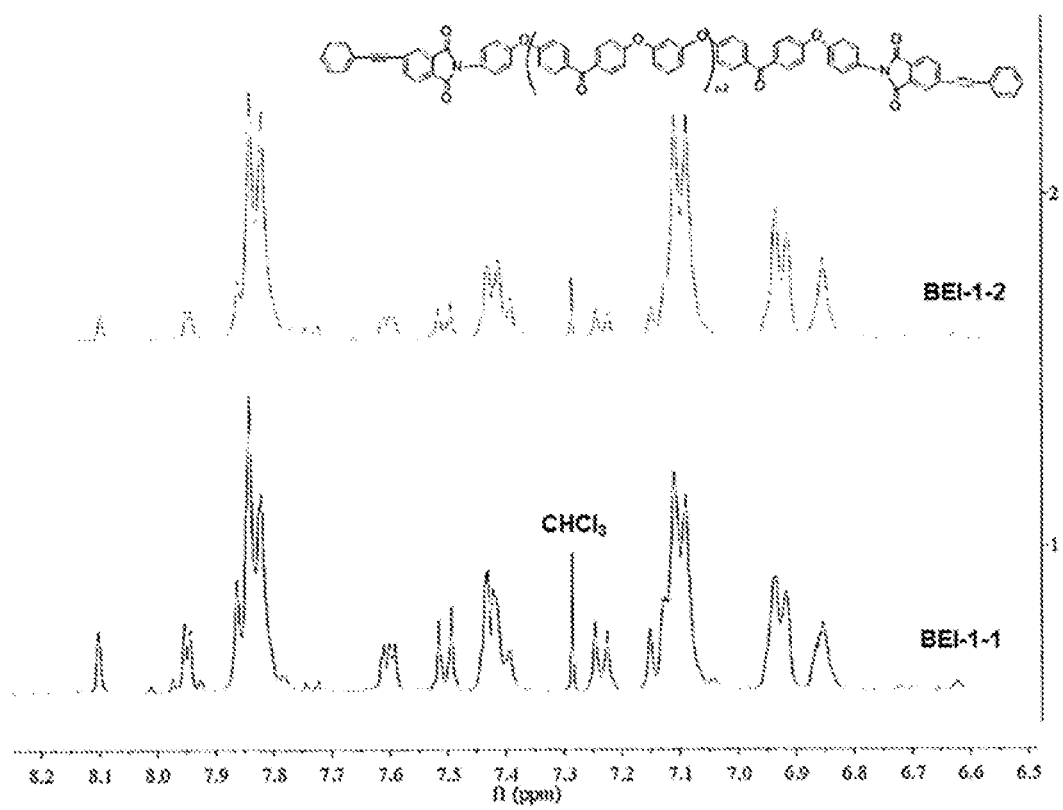

[FIG. 11]
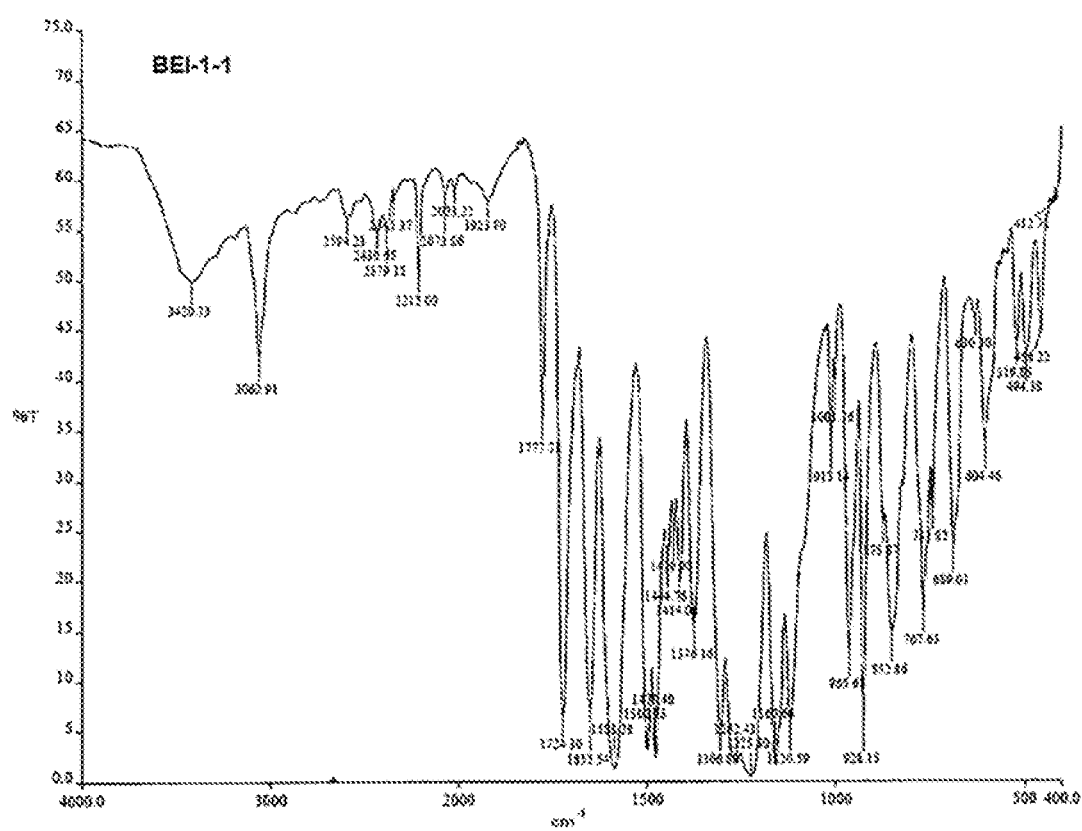

[FIG. 12]
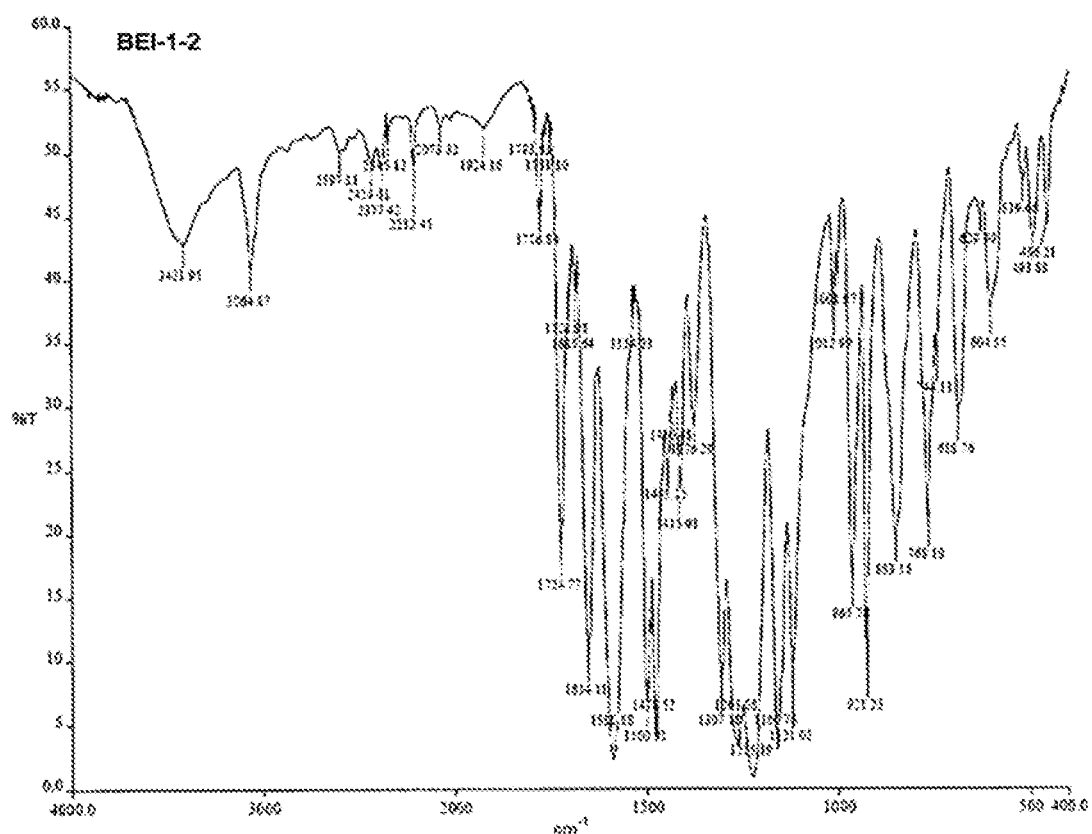

[FIG. 13]
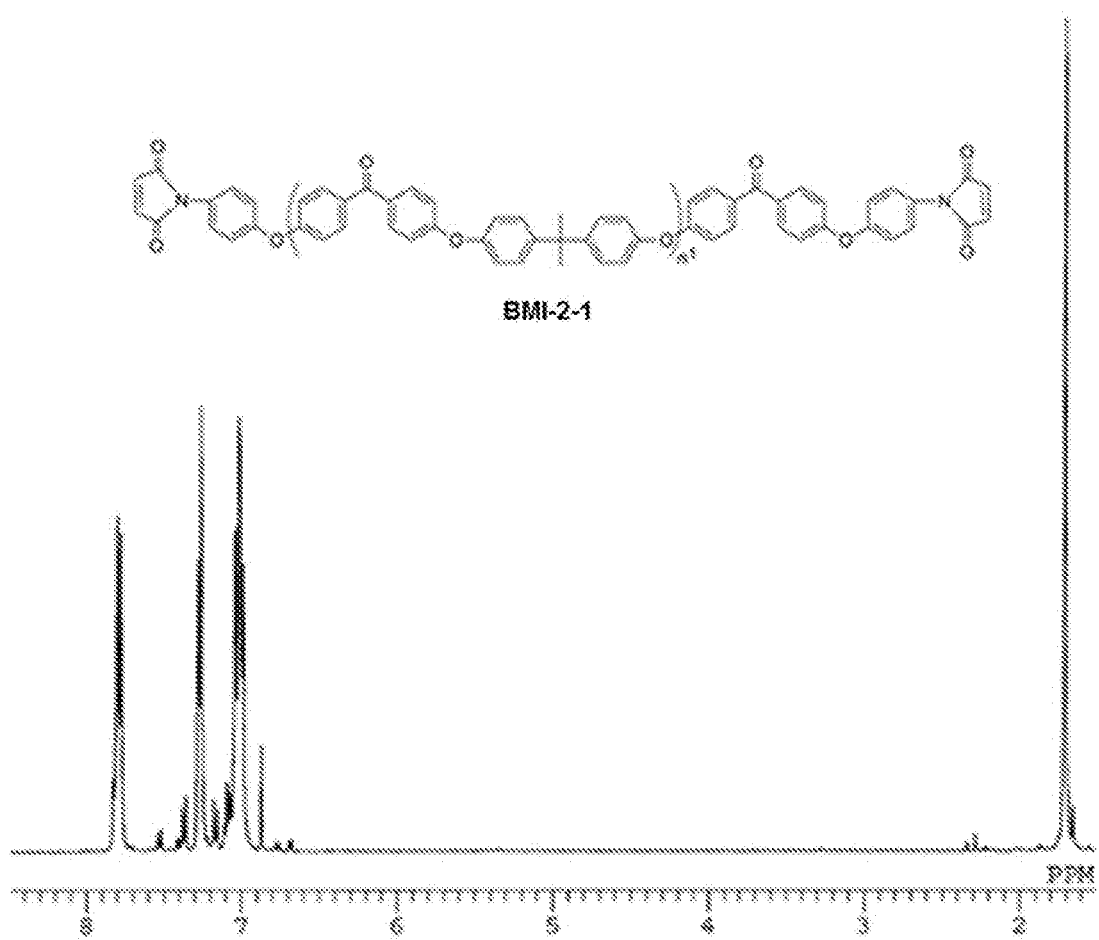

[FIG. 14]
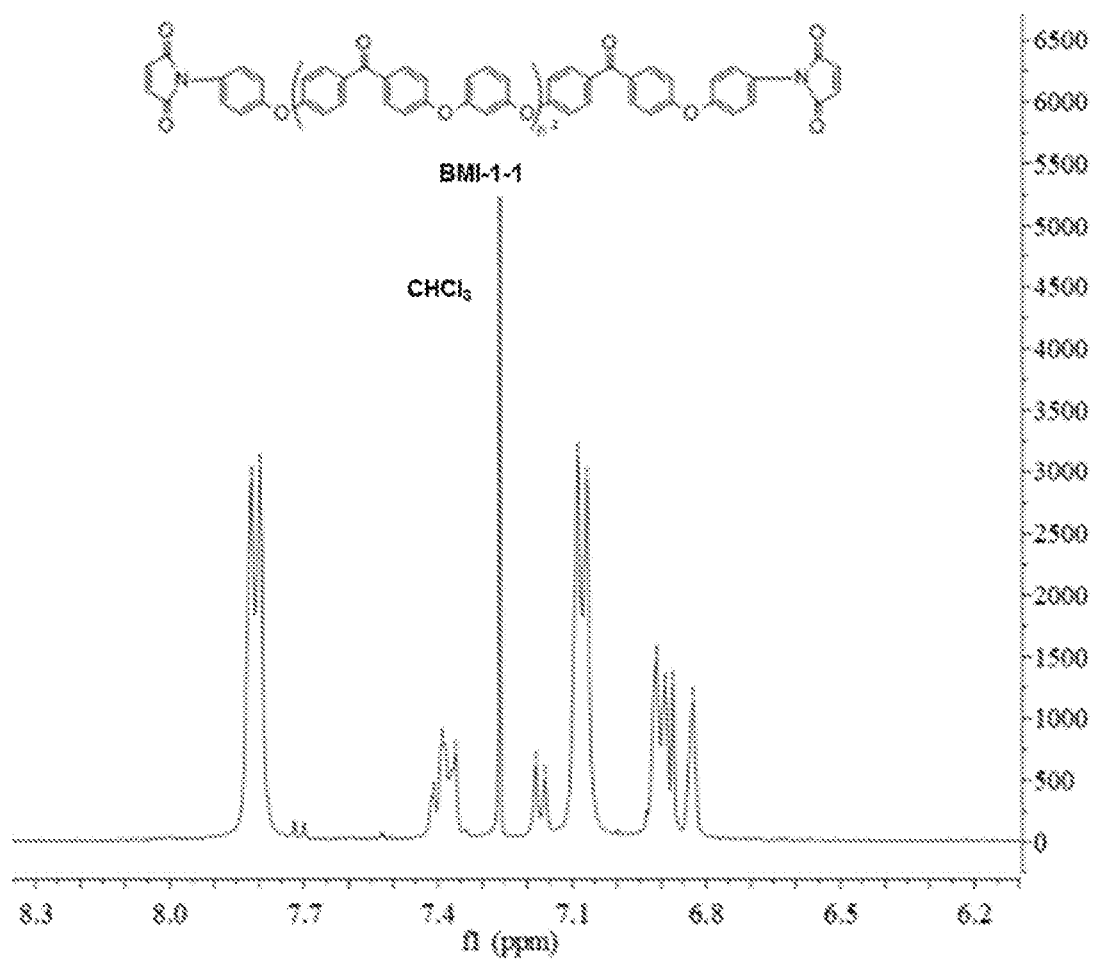

[FIG. 15]
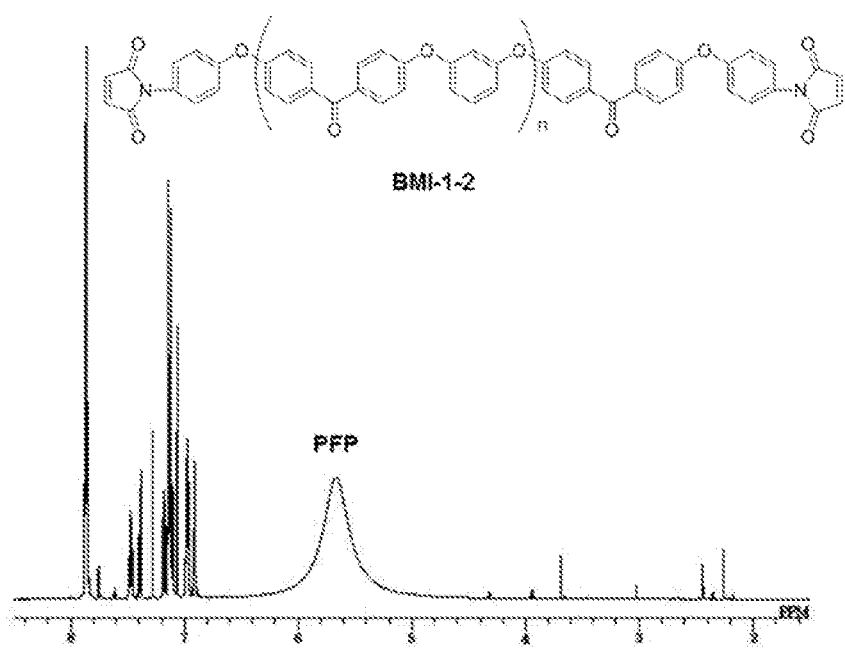

[FIG. 16]
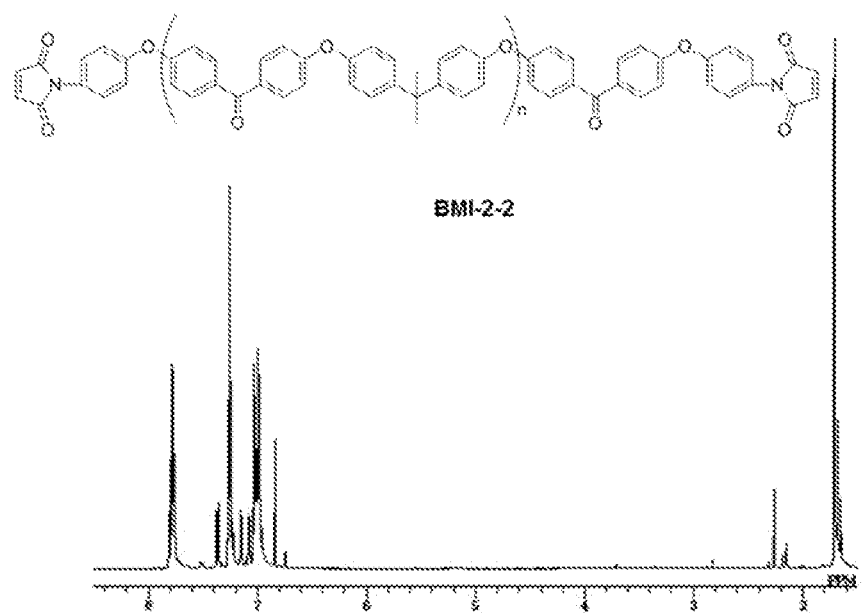

[FIG. 17]
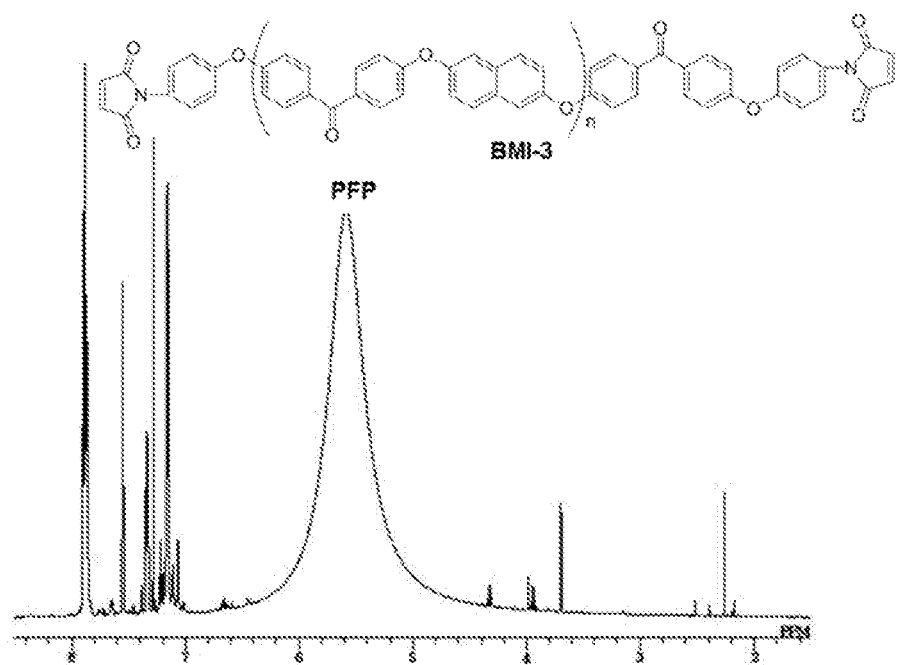

[FIG. 18]
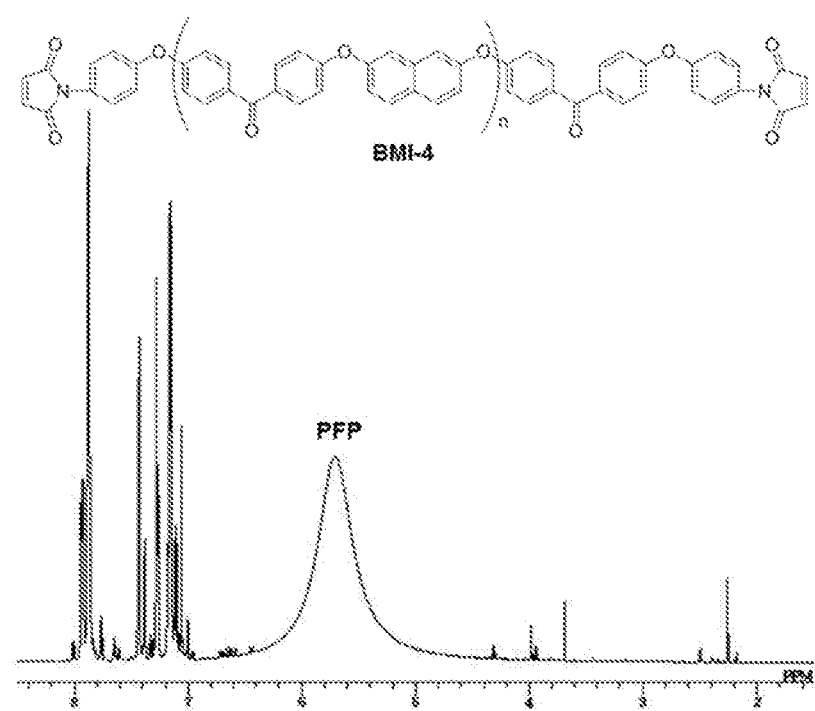

[FIG. 19]
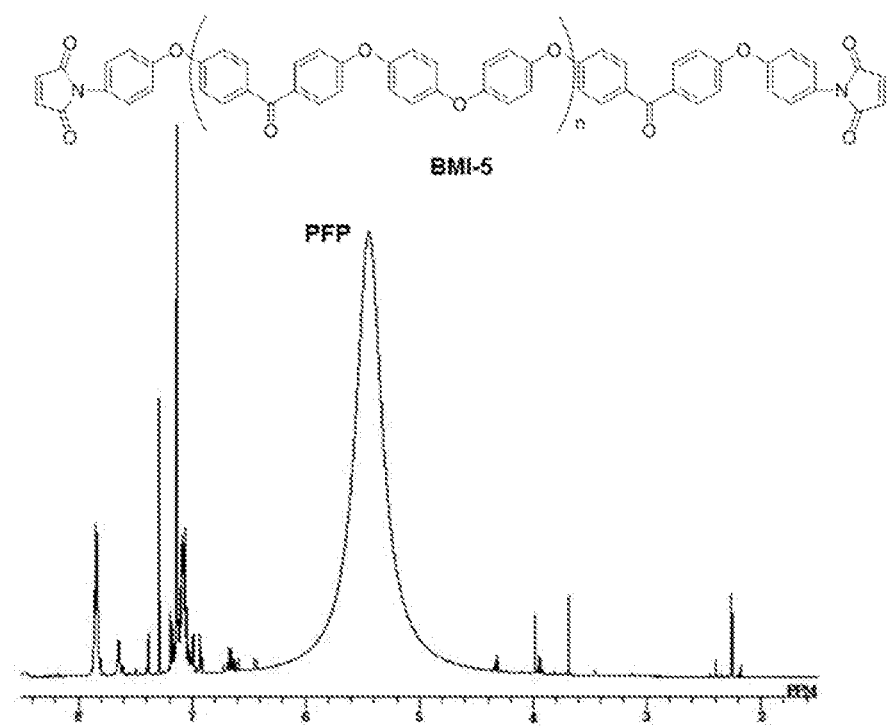

[FIG. 20]
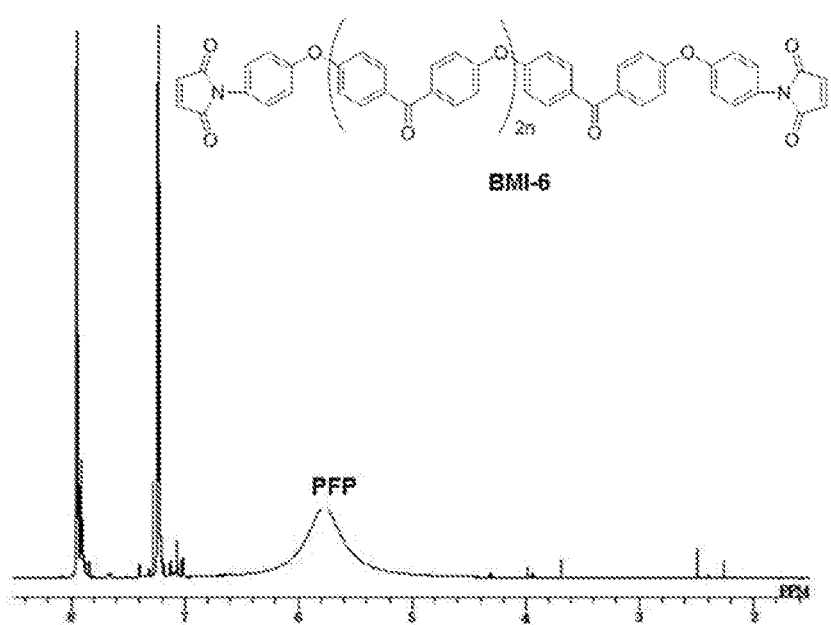

[FIG. 21]
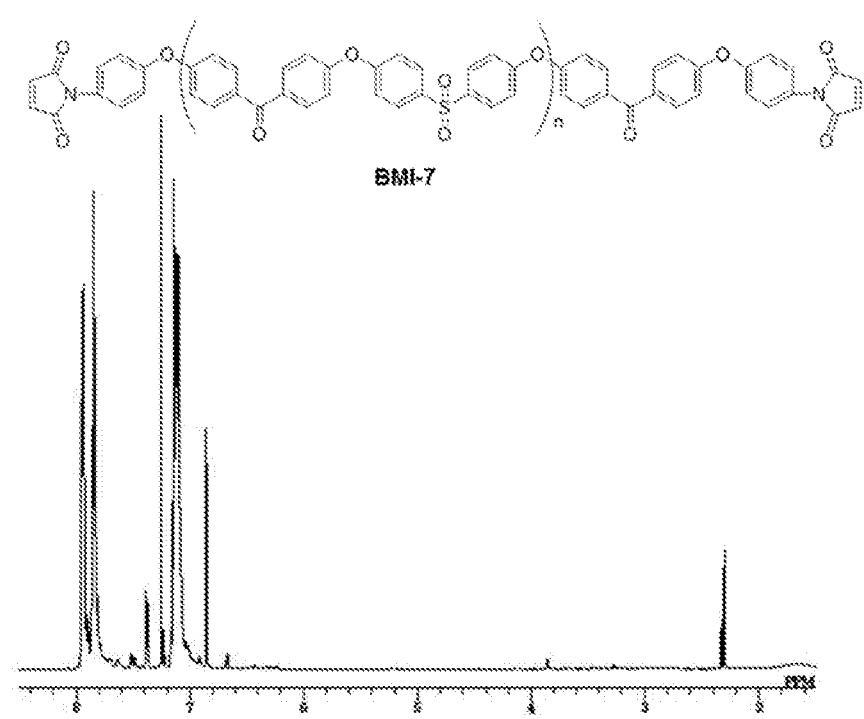

[FIG. 22]
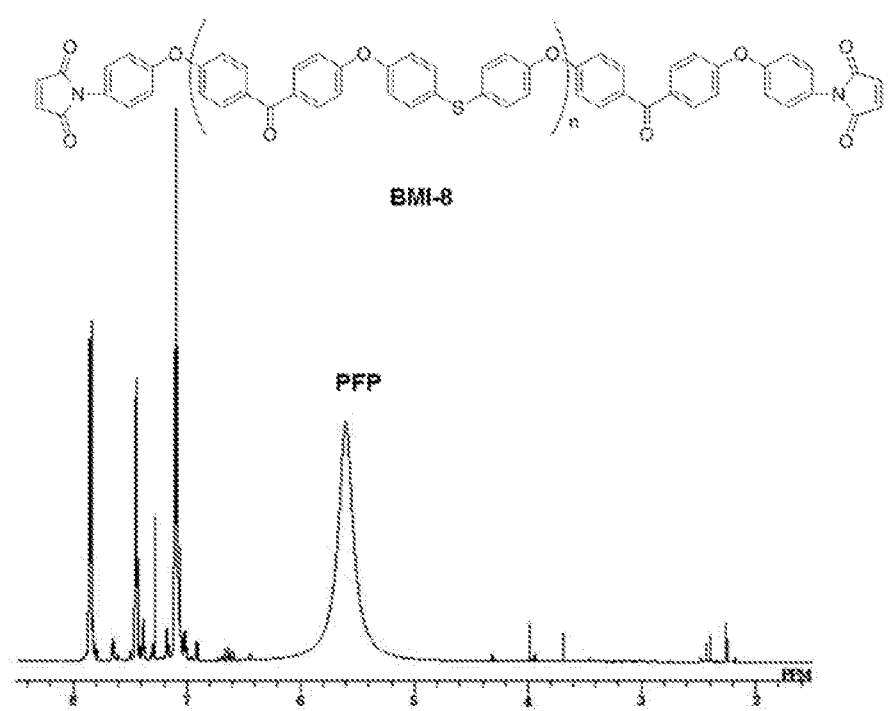

[FIG. 23]
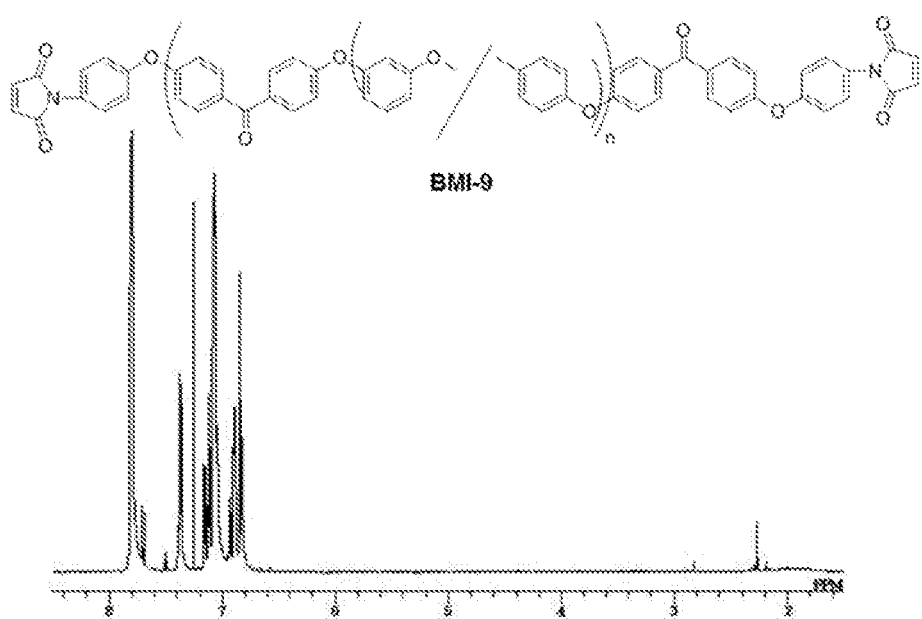

[FIG. 24]
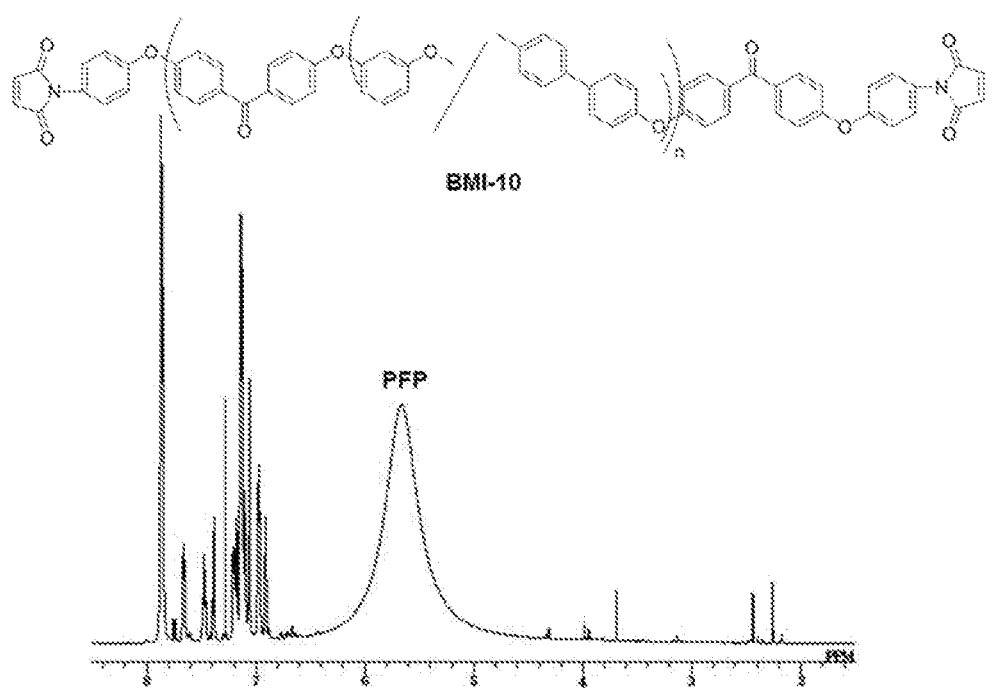

[FIG. 25]
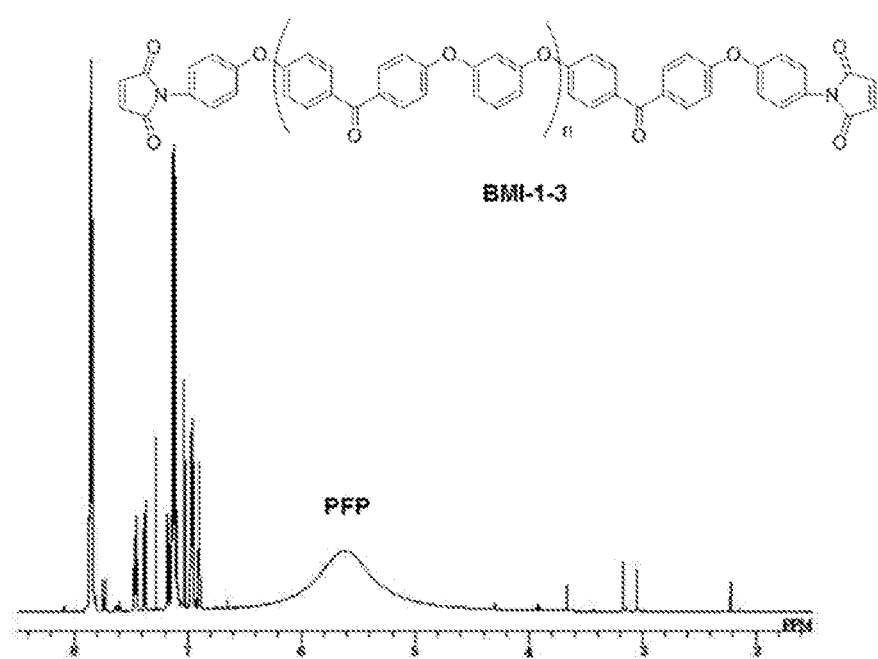

[FIG. 26]
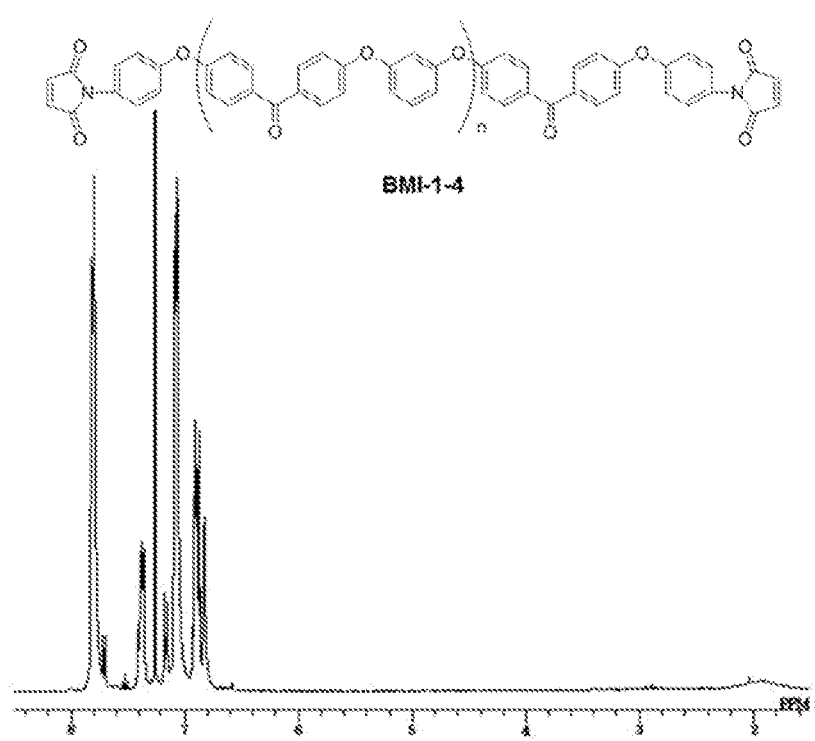

[FIG. 27]
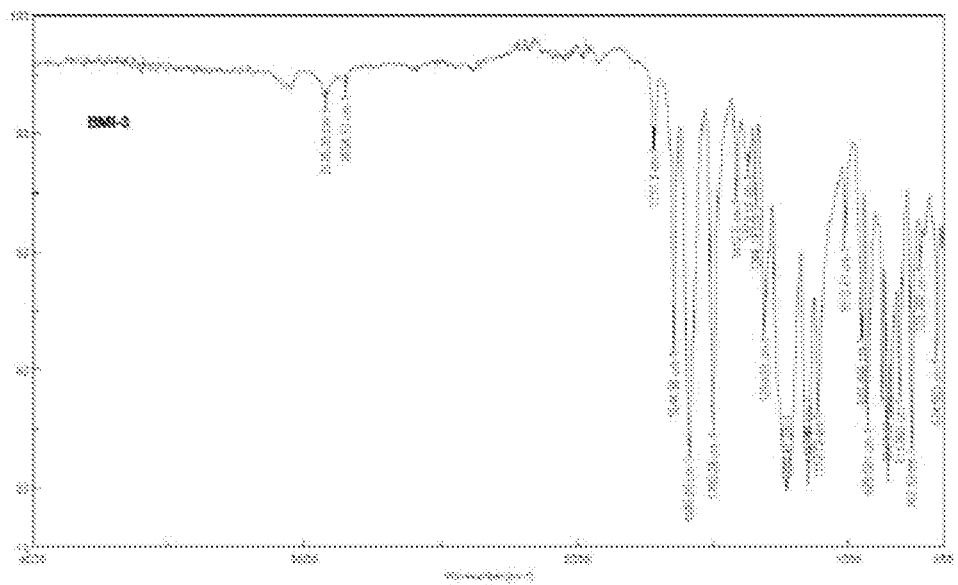
[FIG. 28]
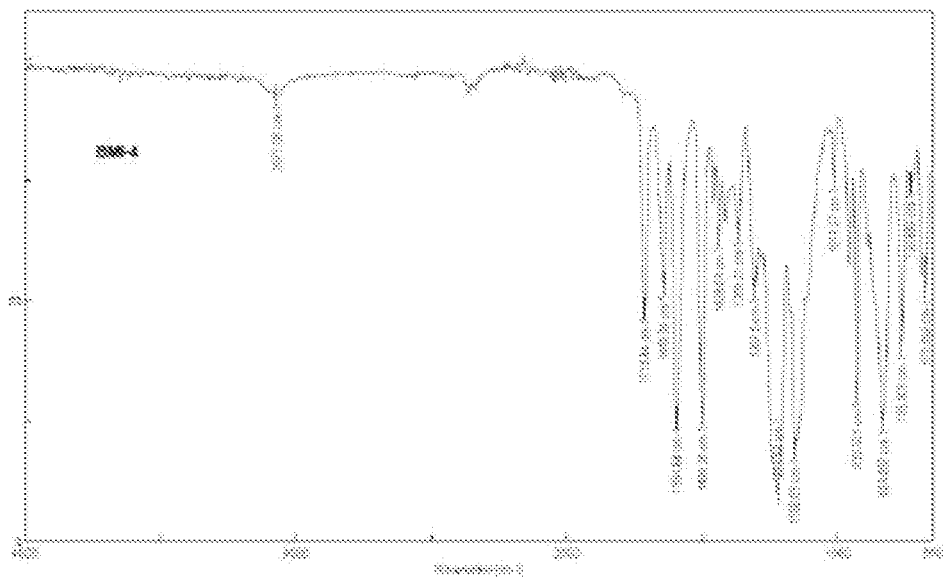

[FIG. 29]
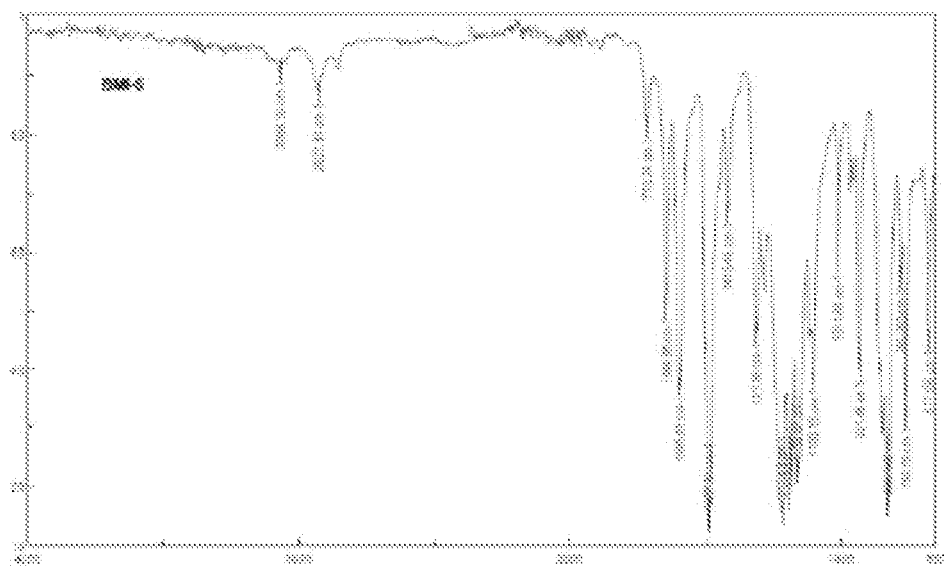
[FIG. 30]
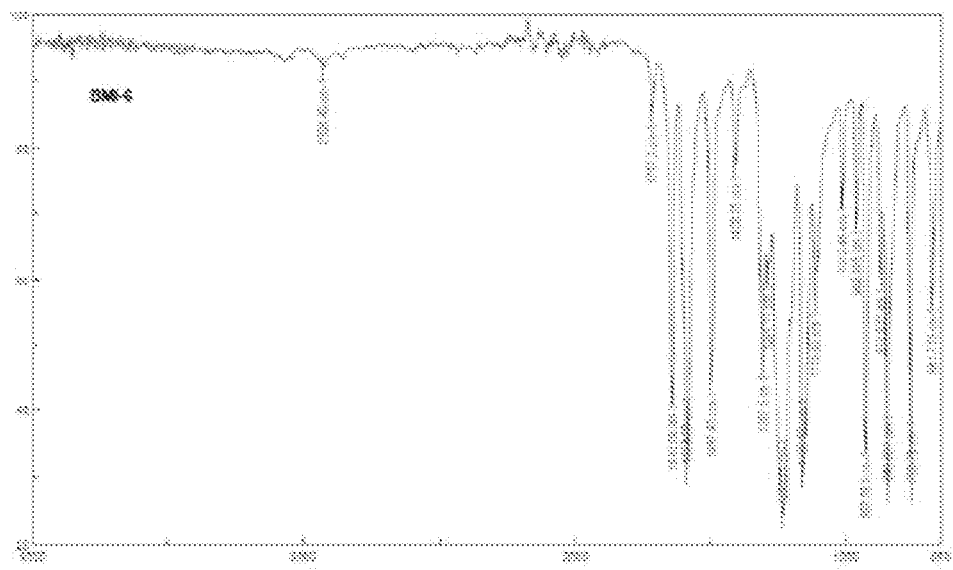

[FIG. 31]
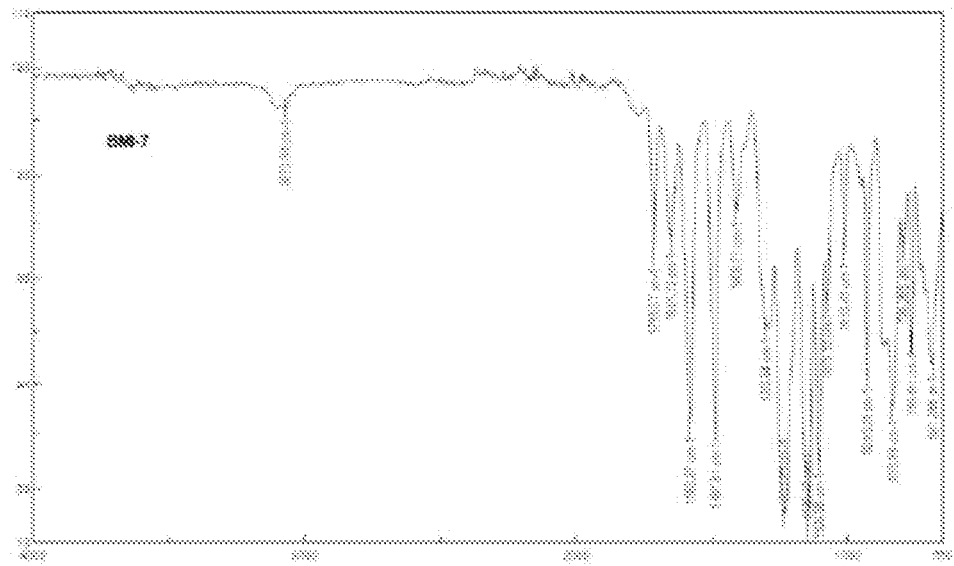
[FIG. 32]
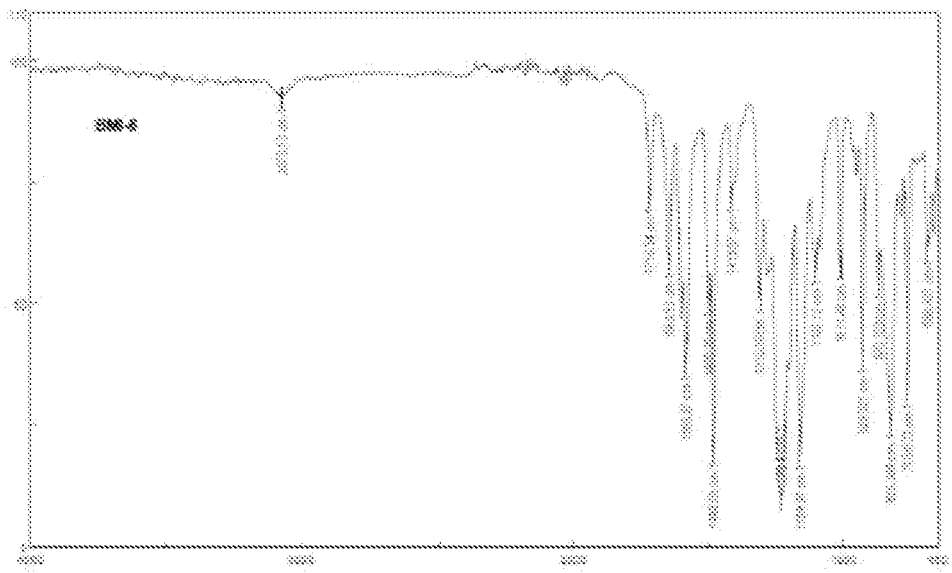

[FIG. 33]
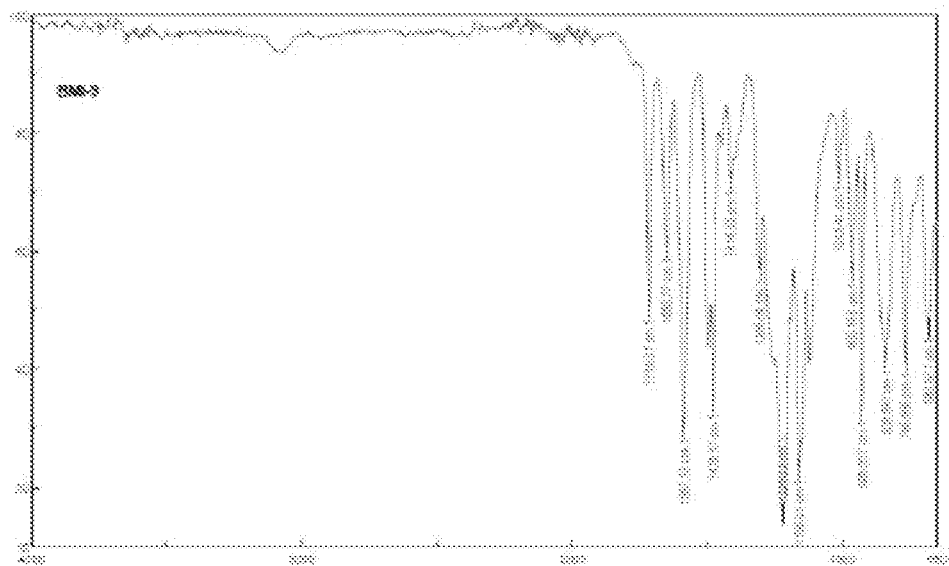
[FIG. 34]
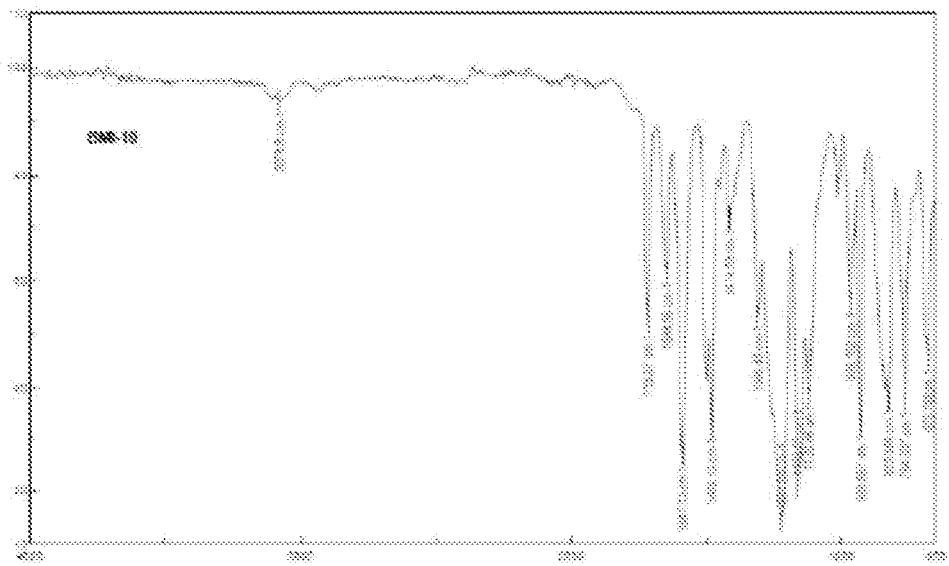

[FIG. 35]
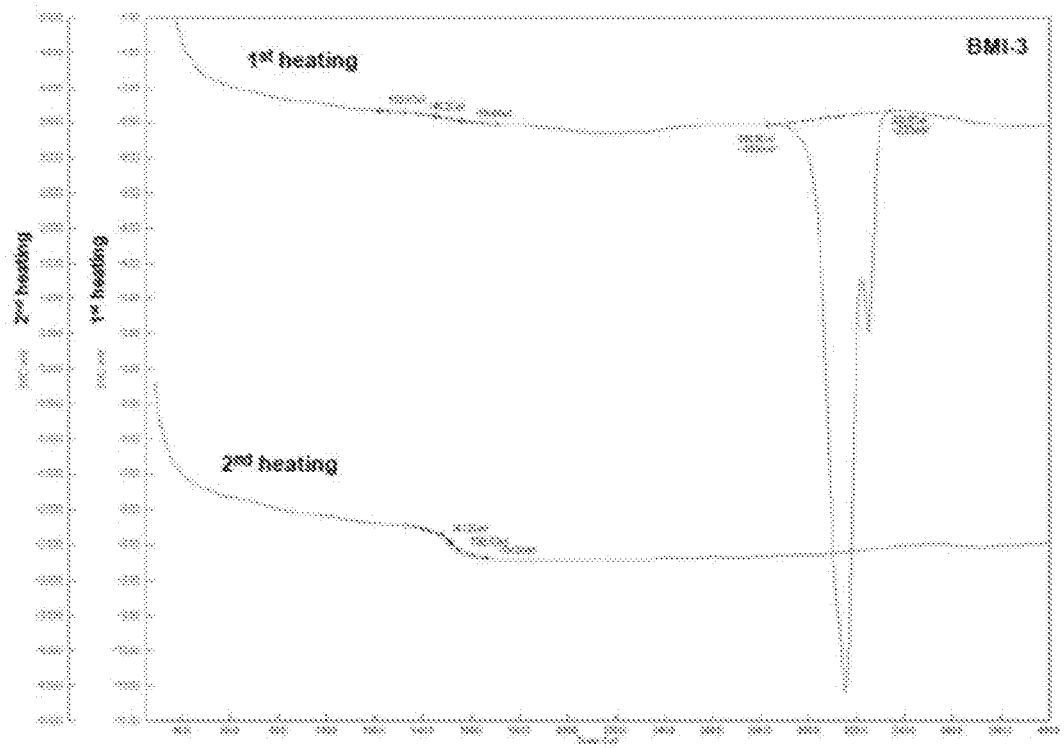
[FIG. 36]
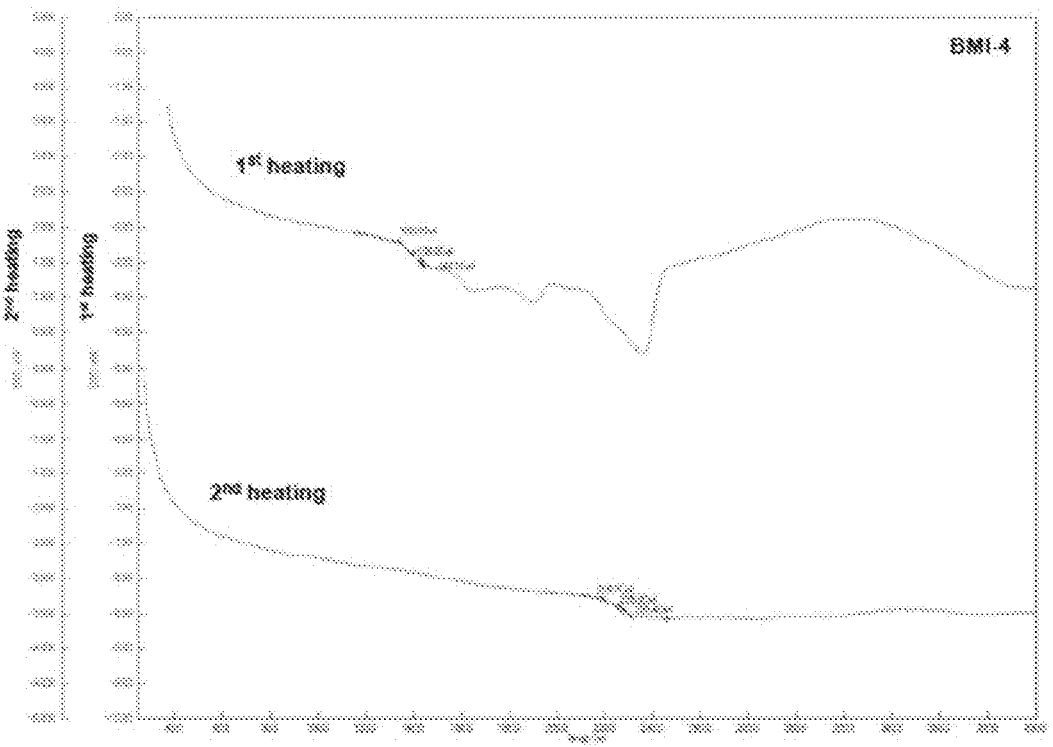

[FIG 37]
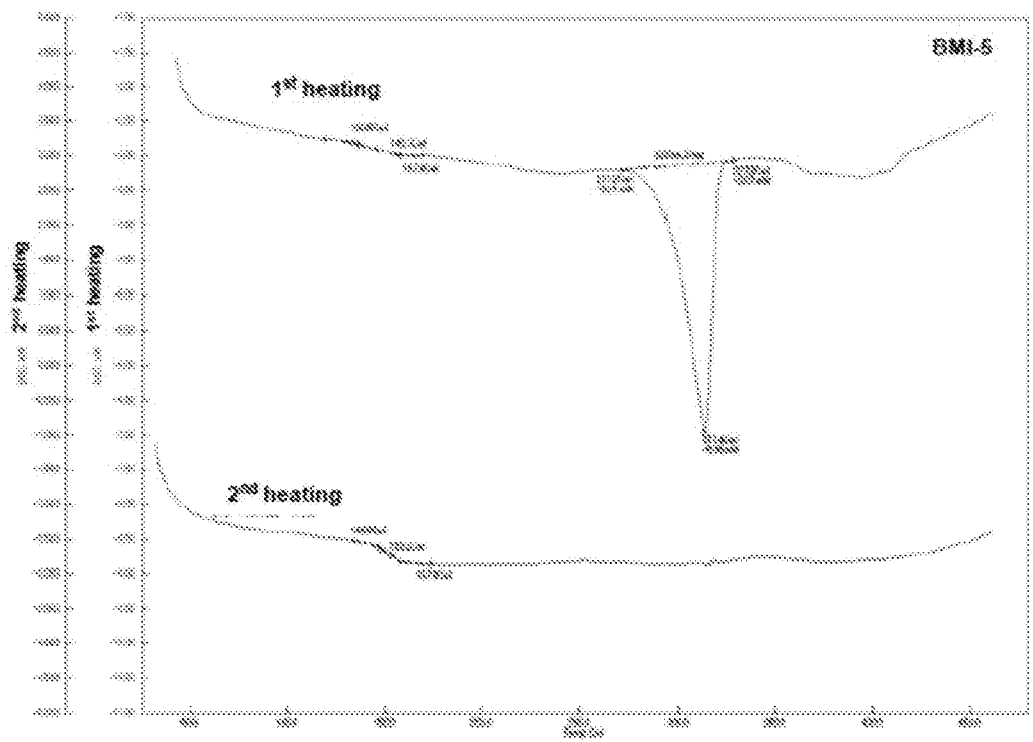
[FIG 38]
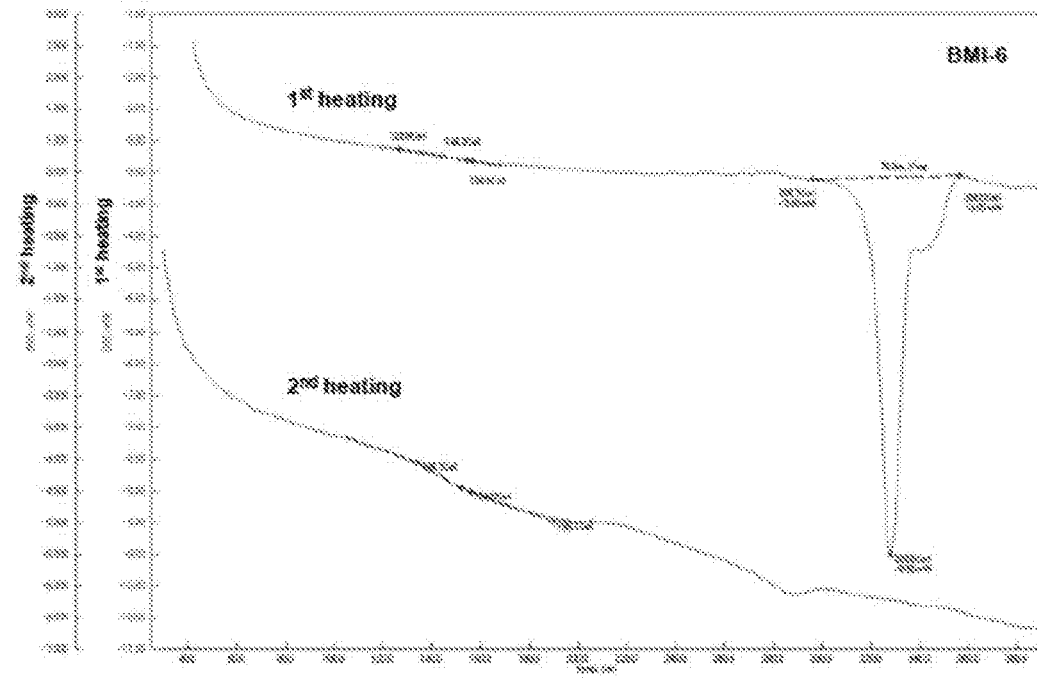

[FIG 39]
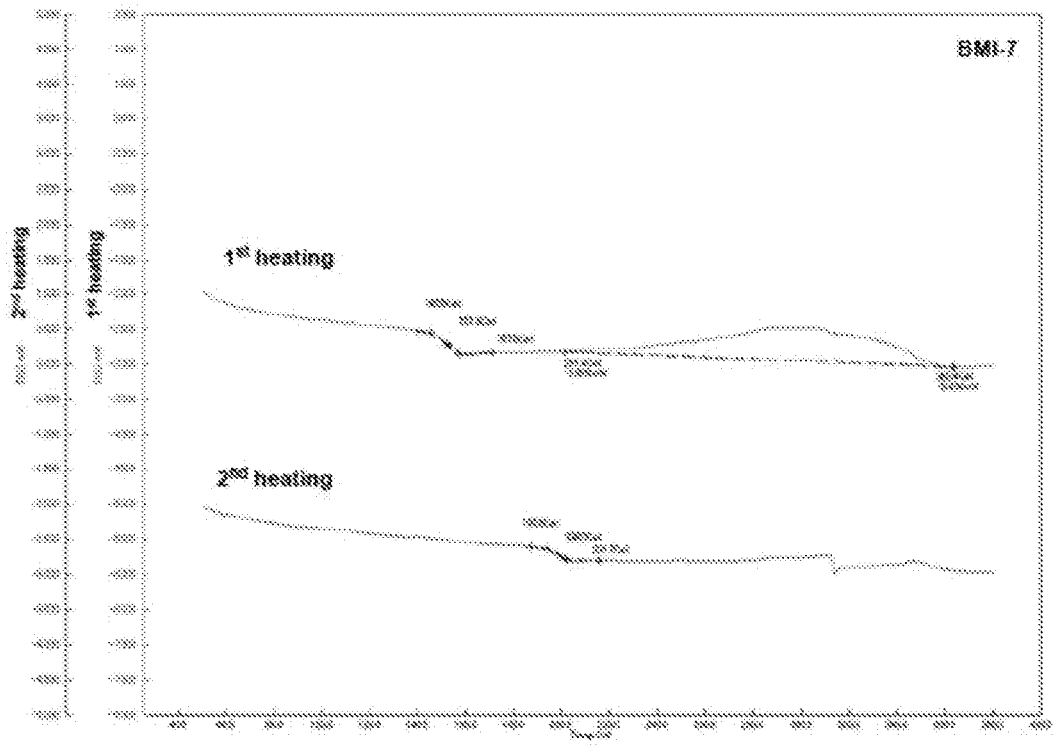
[FIG. 40]
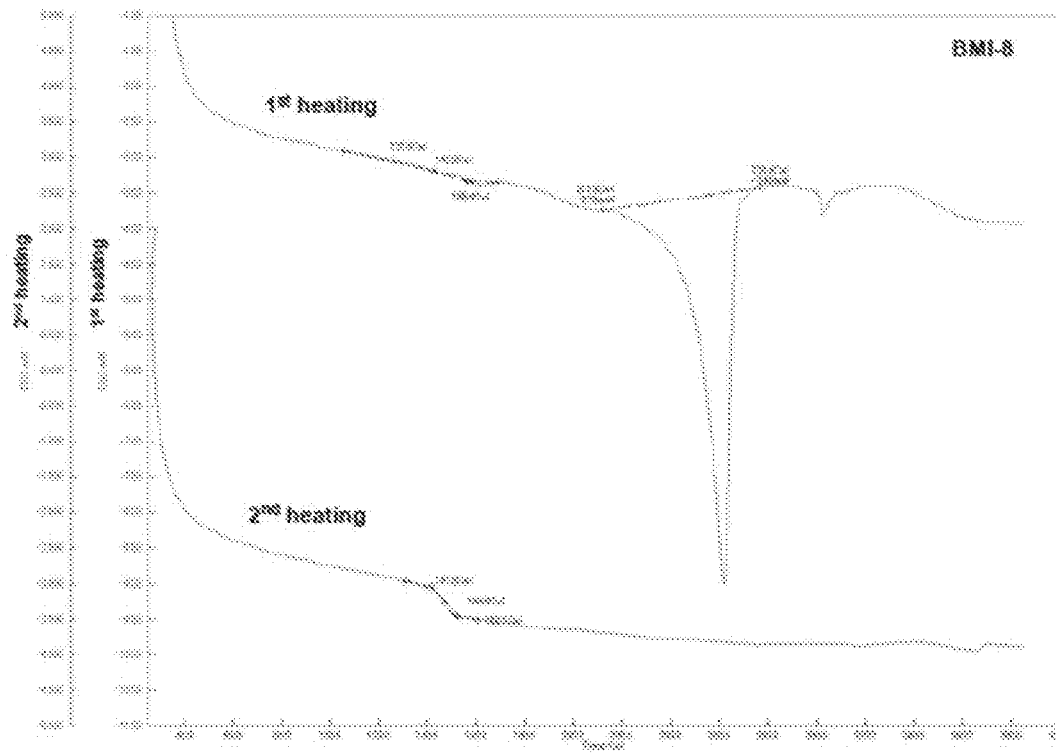

[FIG. 41]
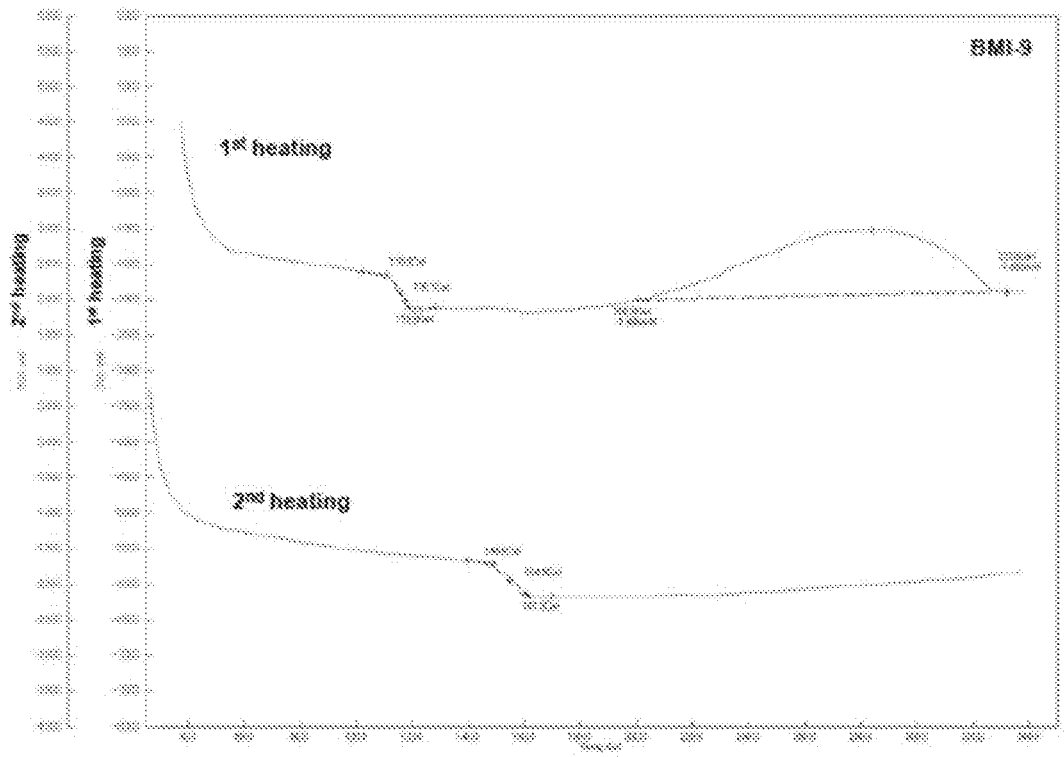
[FIG. 42]
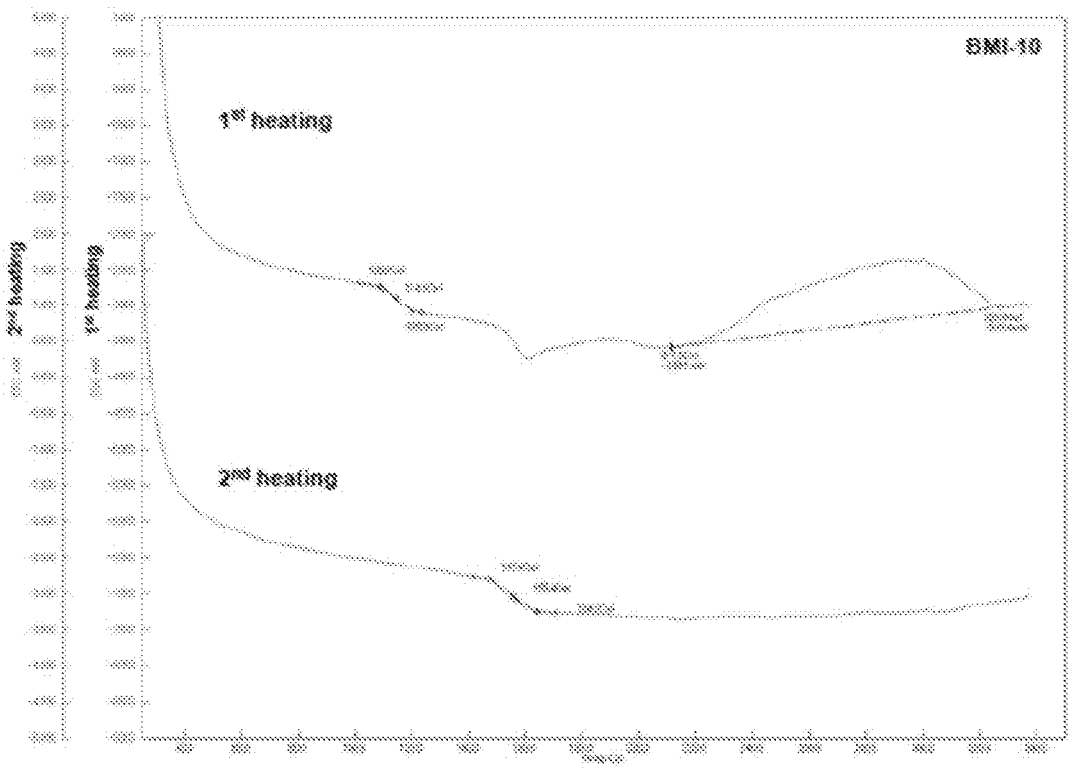

[FIG. 43]
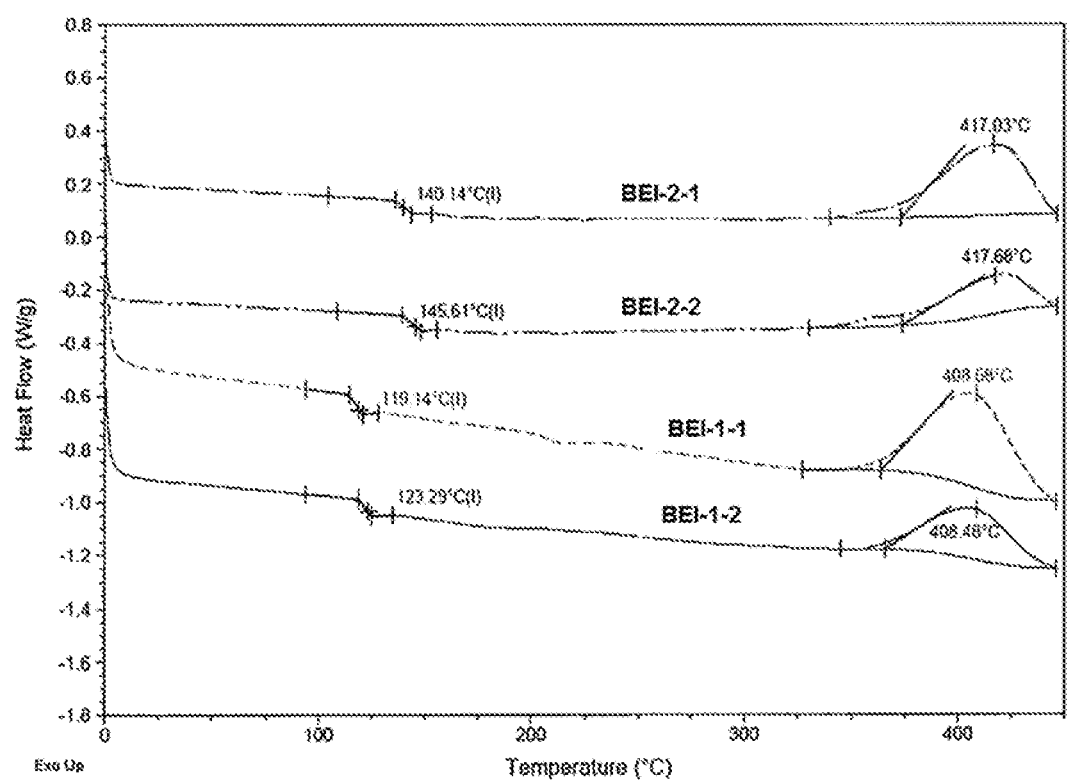

[FIG. 44]
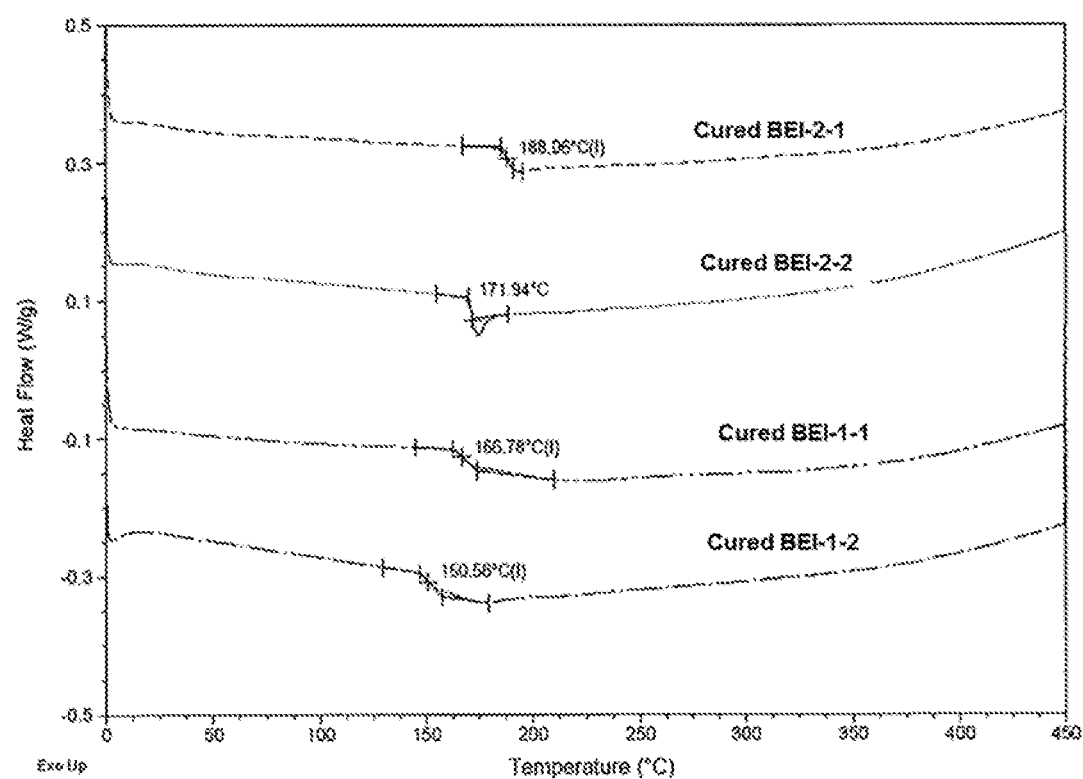

[FIG. 45]
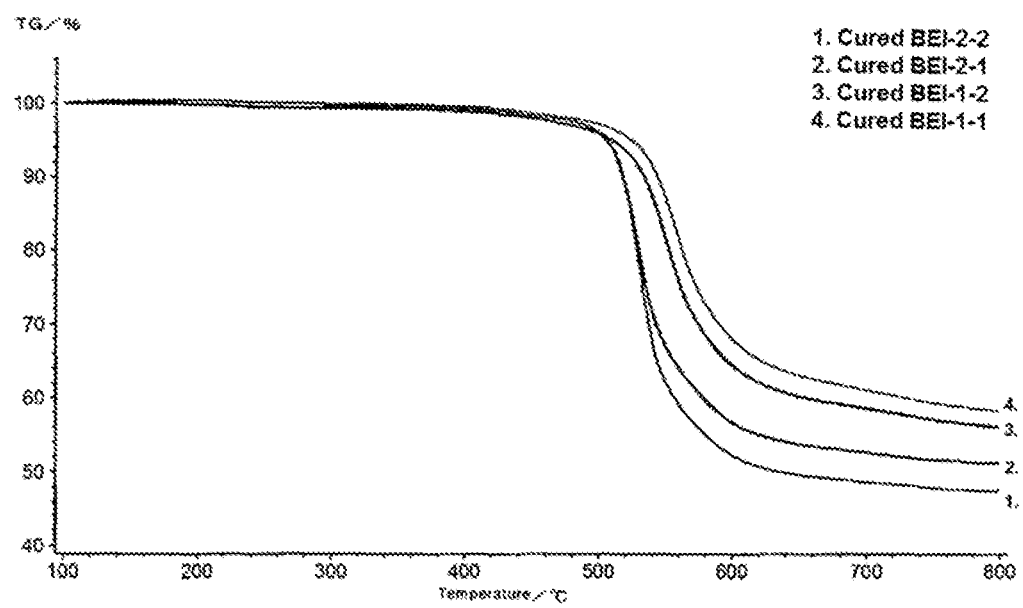
[FIG. 46]
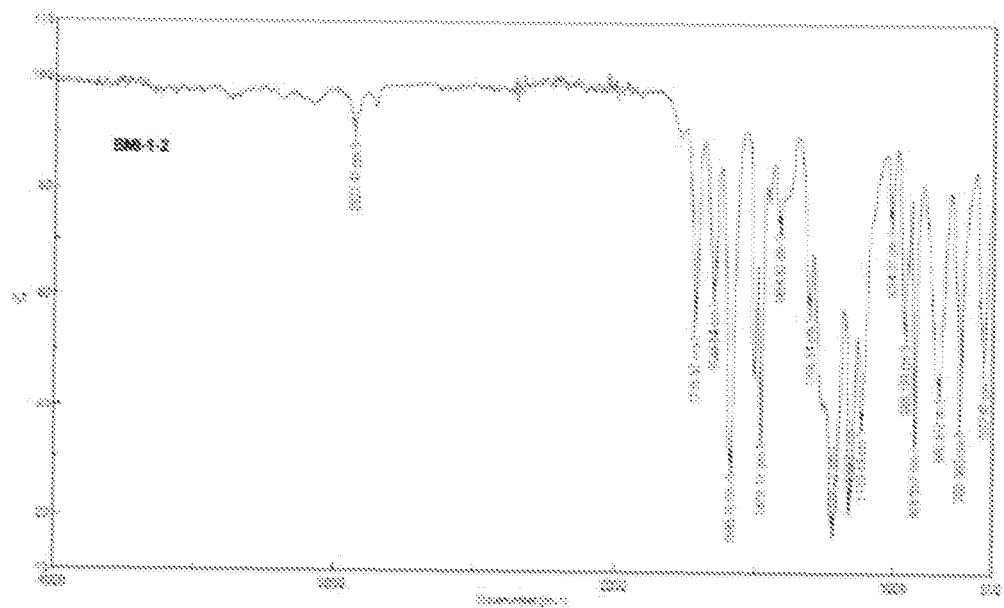

[FIG. 47]
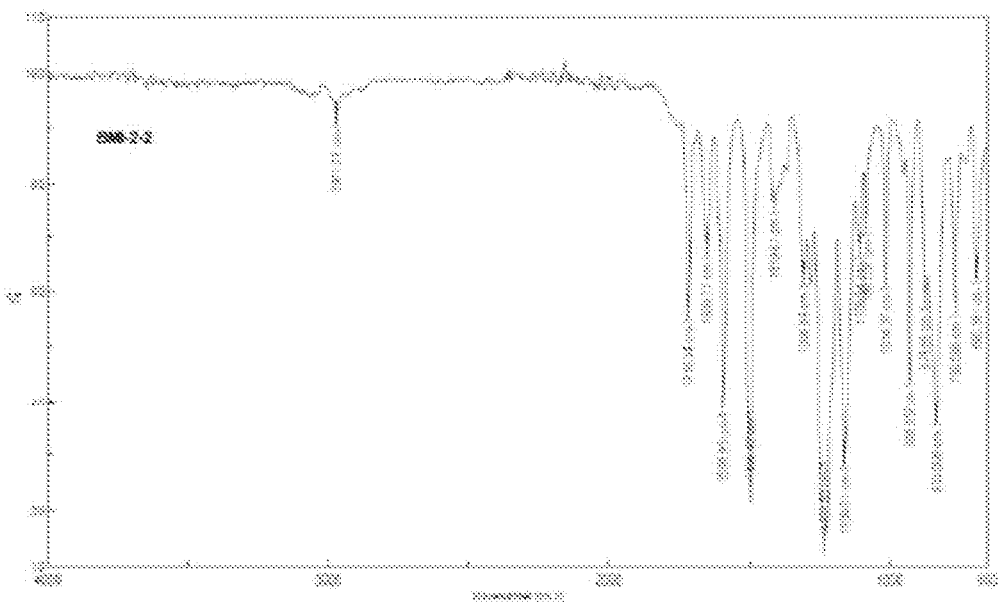

[FIG. 48]
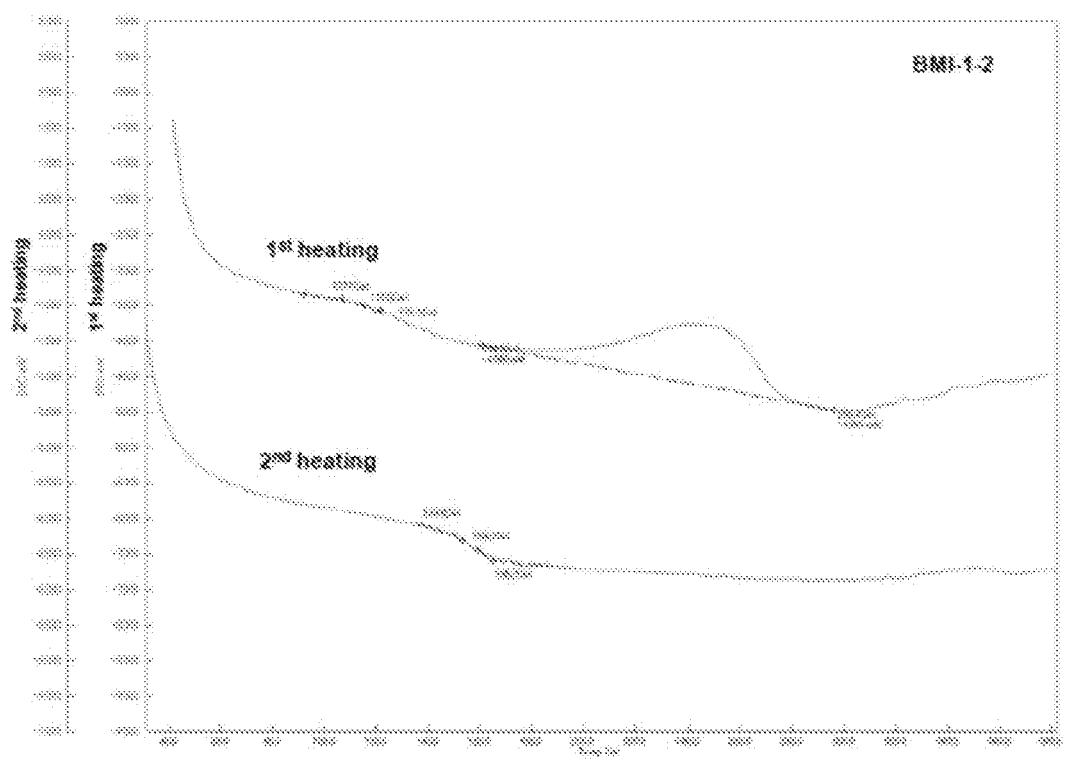
[FIG. 49]
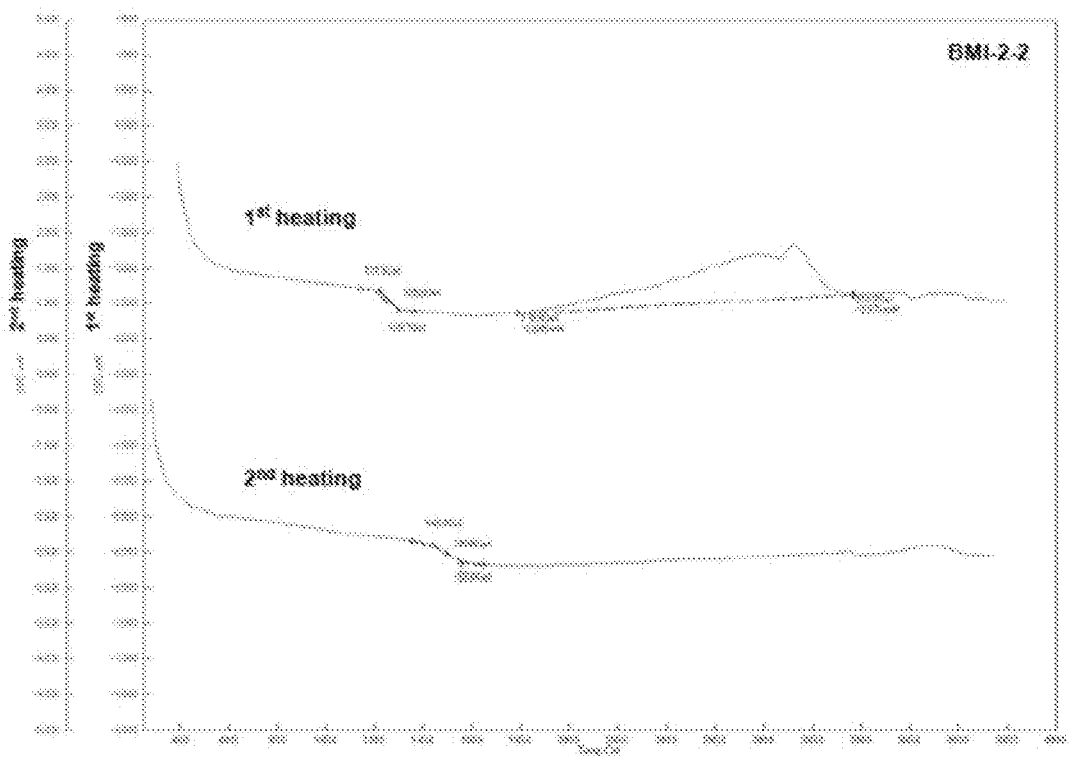

CURABLE COMPOUND

The present application claims priority of PCT/CN2016/110302, filed in the China National Intellectual Property Administration on Dec. 16, 2016, the content of which is hereby incorporated by reference.

TECHNICAL FIELD

The present invention relates to a curable compound, a curable composition comprising the curable compound, a cured material thereof, and a molding comprising the cured material. The present invention relates particularly to a material usable in the fields requiring good processability and high heat resistance, including electronic information, household appliances, cars and precision machines.

BACKGROUND ART

Engineering plastics are high-performance materials having high heat resistance as well as high mechanical properties, and are valued and used as materials essential for size reduction, weight reduction, performance enhancement and reliability enhancement of various types of parts. However, since, for example, polyimide, which has outstanding heat resistance and environmental resistance and strength properties, is hardly soluble and hardly meltable, molding methods of obtaining moldings corresponding with applications are limited. Then, research and development to overcome difficult moldability has been actively progressed and there are demanded materials having both of high mechanical properties, electric properties, chemical resistance, water resistance and high heat resistance which engineering plastics have, and good processability, that is, curable compounds having good solvent solubility and being capable of forming cured materials having super heat resistance as molding materials for composite materials to be used in a severe temperature environment and functional materials such as insulating materials and heat-resistant adhesives.

Aromatic polyimides described in Patent Literature 1 and the like are known to be excellent in heat resistance. The aromatic polyimides, however, since being difficult to dissolve in solvents, are poor in processability, making it difficult to be melt molded and to be used as matrix resins of fiber-reinforced composite materials.

Non Patent Literature 1 describes that by using an asymmetric acid dianhydride, there can be obtained a curable compound having high melt flowability and simultaneously having high heat resistance, high toughness and easy moldability. The curable compound, however, since being hardly soluble to solvents, has such a problem that the curable compound cannot be utilized in applications forming a cured material by a cast process or the like.

Non Patent Literature 2 describes that by using a special monomer containing fluorine, there can be obtained a crosslinkable polyether ketone having solubility to a solvent such as toluene. However, since the special raw material is essential, the utility thereof in the general purpose is poor.

Non Patent Literature 3 describes that a crosslinkable polyether ketone having a solvent solubility can be obtained by using, as raw materials, bisphenol A and bis(4-chlorobenzoyl)benzene or 4,4'-difluorobenzophenone. It has such a problem, however, that in a high molecular weight thereof, the processability is poor, and when the molecular weight is lowered in order to improve the processability, an obtained cured material thereof becomes brittle.

Non Patent Literature 4 describes a curable compound in which an acetylene terminal group is introduced through an ester bond to an ether ketone oligomer composed of a combination of a metaphenylene unit and a paraphenylene unit. It has such problems, however, that the curable compound has crystallinity and is low in solvent solubility and the thermal decomposition initiation temperature of an obtained cured material is also low.

CITATION LIST

Patent Literature

Patent Literature 1: Japanese Patent Laid-open No. 2000-219741

Non Patent Literature

Non Patent Literature 1: Journal of Network Polymer, Japan, Vol. 27(4), pp. 221-231(2006)
Non Patent Literature 2: Polymer Journal, Vol. 34(3), pp. 209-218 (2002)
Non Patent Literature 3: Polymer, Vol. 30, pp. 978-985 (1989)
Non Patent Literature 4: Polymer, Vol. 33(15), pp. 3286-3291 (1992)

SUMMARY OF INVENTION

Technical Problem

Therefore, an object of the present invention is to provide a curable compound having a good solvent solubility and being capable of forming a cured material having a super heat resistance, or a curable composition comprising the same.

Another object of the present invention is to provide a cured material, having a super heat resistance, of the curable composition.

Another object of the present invention is to provide a molding comprising the cured material.

Solution to Problem

As a result of exhaustive studies to solve the above problems, the present inventors have found that a compound represented by the following formula (1) has a good solvent solubility, and is cured by being imparted with an external stimulation such as heat to form a cured material having a super heat resistance. The present invention has been completed based on these findings.

That is, the present invention provides a curable compound represented by the following formula (1):

[Formula 1]

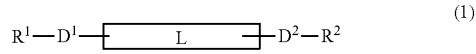

(1)

wherein $R^1$ and $R^2$ are identical or different and each represent a curable functional group; $D^1$ and $D^2$ are identical or different and each represent a single bond or a linking group; and L represents a divalent group having a repeating unit containing a structure represented by the following formula (I) and a structure represented by the following formula (II):

[Formula 2]

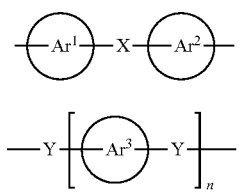
(I)

(II)

wherein Ar¹ to Ar³ are identical or different and each represent a group made by eliminating two hydrogen atoms from a structural formula of an aromatic ring or a group made by eliminating two hydrogen atoms from a structural formula in which two or more aromatic rings are bound through a single bond or a linking group; X represents —CO—, —S— or —SO$_2$—; each Y is identical or different and represents —S—, —SO$_2$—, —O—, —CO—, —COO— or —CONH—; and n represents an integer of 0 or more.

The present invention also provides the curable compound in which R¹ and R² in the formula (1) are identical or different and are each a curable functional group having a cyclic imide structure.

The present invention also provides the curable compound in which R¹ and R² in the formula (1) are identical or different and are each a group selected from groups represented by the following formulas (r-1) to (r-6):

[Formula 3]

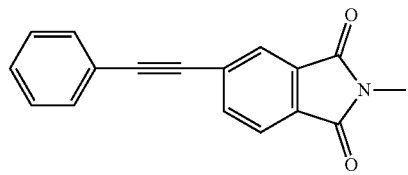
(r-1)

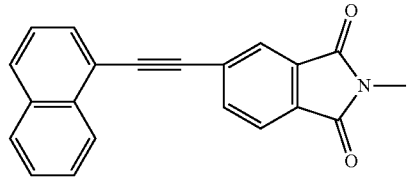
(r-2)

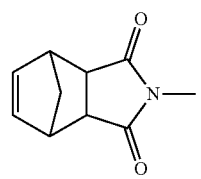
(r-3)

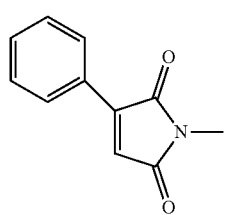
(r-4)

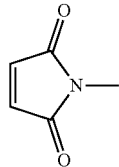
(r-5)

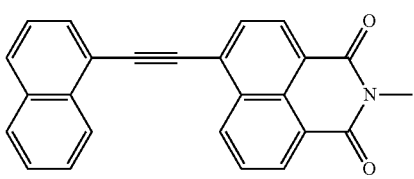
(r-6)

wherein a bond extending from a nitrogen atom in the formulas is bound to D¹ or D².

The present invention also provides the curable compound in which D¹ and D² in the formula (1) are identical or different and are each a group selected from groups containing structures represented by the following formulas (d-1) to (d-4):

[Formula 4]

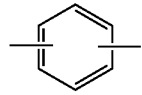
(d-1)

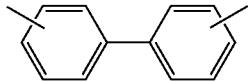
(d-2)

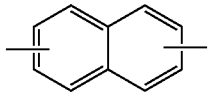
(d-3)

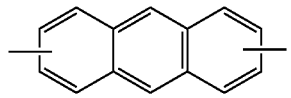
(d-4)

The present invention also provides the curable compound in which Ar¹ to Ar³ in the formula (I) and the formula (II) are identical or different and are each a group made by eliminating two hydrogen atoms from a structural formula of an aromatic ring having 6 to 14 carbon atoms, or a group made by eliminating two hydrogen atoms from a structural formula in which two or more aromatic rings having 6 to 14 carbon atoms are bound through a single bond, a straight-chain or branched-chain alkylene group having 1 to 5 carbon atoms or a group made by replacing one or more hydrogen atoms of a straight-chain or branched-chain alkylene group having 1 to 5 carbon atoms with halogen atoms.

The present invention also provides the curable compound in which the structure represented by the formula (I) is a structure derived from benzophenone.

The present invention also provides the curable compound in which the proportion of the amount of a structural unit derived from benzophenone to the total amount of the curable compound represented by the formula (1) is 5% by weight or more.

The present invention also provides the curable compound in which the structure represented by the formula (II) is a structure derived from at least one compound selected from hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone and bisphenol A.

The present invention also provides the curable compound in which the proportion of the amount of a structural unit derived from hydroquinone, resorcinol and bisphenol A to the total amount of the curable compound represented by the formula (1) is 5% by weight or more.

The present invention also provides a curable composition comprising the curable compound.

The present invention also provides a cured material of the curable composition. The present invention also provides a molding comprising the cured material.

Advantageous Effects of Invention

The curable compound having the above constitution according to the present invention (particularly a compound in which specific curable functional groups are introduced to both terminals of a molecular chain having a repeating unit containing a structural unit derived from benzophenone and a structural unit derived from at least one compound selected from hydroquinone, resorcinol and bisphenol A) has good solvent solubility. Further, the curable compound can be cured more quickly by being subjected to a heat treatment or the like to form a cured material having a super heat resistance. The cured material has also good dielectric properties (low relative dielectric constant and dielectric loss tangent). Hence, the curable compound according to the present invention can suitably be used in the fields requiring good processability (or easy moldability) and high heat resistance, including electronic information, household appliances, cars and precision machines.

BRIEF DESCRIPTION OF DRAWINGS

FIG. 1 is a diagram showing $^1$H-NMR spectra (DMSO-d6) of Diamine-2-1 and Diamine-2-2 obtained in Preparation Examples 1 and 2.

FIG. 2 is a diagram showing an FTIR spectrum of Diamine-2-1 obtained in Preparation Example 1.

FIG. 3 is a diagram showing an FTIR spectrum of Diamine-2-2 obtained in Preparation Example 2.

FIG. 4 is a diagram showing $^1$H-NMR spectra (DMSO-d6) of Diamine-1-1 and Diamine-1-2 obtained in Preparation Examples 3 and 4.

FIG. 5 is a diagram showing an FTIR spectrum of Diamine-1-1 obtained in Preparation Example 3.

FIG. 6 is a diagram showing an FTIR spectrum of Diamine-1-2 obtained in Preparation Example 4.

FIG. 7 is a diagram showing $^1$H-NMR spectra (CDCl$_3$) of BEI-2-1 and BEI-2-2 obtained in Examples 1 and 2.

FIG. 8 is a diagram showing an FTIR spectrum of BEI-2-1 obtained in Example 1.

FIG. 9 is a diagram showing an FTIR spectrum of BEI-2-2 obtained in Example 2.

FIG. 10 is a diagram showing $^1$H-NMR spectra (CDCl$_3$) of BEI-1-1 and BEI-1-2 obtained in Examples 3 and 4.

FIG. 11 is a diagram showing an FTIR spectrum of BEI-1-1 obtained in Example 3.

FIG. 12 is a diagram showing an FTIR spectrum of BEI-1-2 obtained in Example 4.

FIG. 13 is a diagram showing a $^1$H-NMR spectrum (CDCl$_3$) of BMI-2-1 obtained in Example 5.

FIG. 14 is a diagram showing a $^1$H-NMR spectrum (CDCl$_3$) of BMI-1-1 obtained in Example 6.

FIG. 15 is a diagram showing a $^1$H-NMR spectrum (CDCl$_3$/PFP=2/1) of BMI-1-2 obtained in Example 7.

FIG. 16 is a diagram showing a $^1$H-NMR spectrum (CDCl$_3$) of BMI-2-2 obtained in Example 8.

FIG. 17 is a diagram showing a $^1$H-NMR spectrum (CDCl$_3$/PFP=2/1) of BMI-3 obtained in Example 9.

FIG. 18 is a diagram showing a $^1$H-NMR spectrum (CDCl$_3$/PFP=2/1) of BMI-4 obtained in Example 10.

FIG. 19 is a diagram showing a $^1$H-NMR spectrum (CDCl$_3$/PFP=2/1) of BMI-5 obtained in Example 11.

FIG. 20 is a diagram showing a $^1$H-NMR spectrum (CDCl$_3$/PFP=2/1) of BMI-6 obtained in Example 12.

FIG. 21 is a diagram showing a $^1$H-NMR spectrum (CDCl$_3$) of BMI-7 obtained in Example 13.

FIG. 22 is a diagram showing a $^1$H-NMR spectrum (CDCl$_3$/PFP=2/1) of BMI-8 obtained in Example 14.

FIG. 23 is a diagram showing a $^1$H-NMR spectrum (CDCl$_3$) of BMI-9 obtained in Example 15.

FIG. 24 is a diagram showing a $^1$H-NMR spectrum (CDCl$_3$/PFP=2/1) of BMI-10 obtained in Example 16.

FIG. 25 is a diagram showing a $^1$H-NMR spectrum (CDCl$_3$/PFP=2/1) of BMI-1-3 obtained in Example 17.

FIG. 26 is a diagram showing a $^1$H-NMR spectrum (CDCl$_3$) of BMI-1-4 obtained in Example 18.

FIG. 27 is a diagram showing an FTIR spectrum of BMI-3 obtained in Example 9.

FIG. 28 is a diagram showing an FTIR spectrum of BMI-4 obtained in Example 10.

FIG. 29 is a diagram showing an FTIR spectrum of BMI-5 obtained in Example 11.

FIG. 30 is a diagram showing an FTIR spectrum of BMI-6 obtained in Example 12.

FIG. 31 is a diagram showing an FTIR spectrum of BMI-7 obtained in Example 13.

FIG. 32 is a diagram showing an FTIR spectrum of BMI-8 obtained in Example 14.

FIG. 33 is a diagram showing an FTIR spectrum of BMI-9 obtained in Example 15.

FIG. 34 is a diagram showing an FTIR spectrum of BMI-10 obtained in Example 16.

FIG. 35 is a diagram showing a DSC measurement result of a cured material of BMI-3 obtained in Example 9.

FIG. 36 is a diagram showing a DSC measurement result of a cured material of BMI-4 obtained in Example 10.

FIG. 37 is a diagram showing a DSC measurement result of a cured material of BMI-5 obtained in Example 11.

FIG. 38 is a diagram showing a DSC measurement result of a cured material of BMI-6 obtained in Example 12.

FIG. 39 is a diagram showing a DSC measurement result of a cured material of BMI-7 obtained in Example 13.

FIG. 40 is a diagram showing a DSC measurement result of a cured material of BMI-8 obtained in Example 14.

FIG. 41 is a diagram showing a DSC measurement result of a cured material of BMI-9 obtained in Example 15.

FIG. 42 is a diagram showing a DSC measurement result of a cured material of BMI-10 obtained in Example 16.

FIG. 43 is a diagram showing DSC measurement results of BEI-2-1, BEI-2-2, BEI-1-1 and BEI-1-2 obtained in Examples 1 to 4.

FIG. 44 is a diagram showing DSC measurement results of cured materials of BEI-2-1, BEI-2-2, BEI-1-1 and BEI-1-2 obtained in Examples 1 to 4.

FIG. 45 is a diagram showing thermogravimetric loss analysis results of cured materials of BEI-2-1, BEI-2-2, BEI-1-1 and BEI-1-2 obtained in Examples 1 to 4.

FIG. 46 is a diagram showing an FTIR spectrum of BMI-1-2 obtained in Example 7.

FIG. 47 is a diagram showing an FTIR spectrum of BMI-2-2 obtained in Example 8.

FIG. 48 is a diagram showing a DSC measurement result of BMI-1-2 obtained in Example 7.

FIG. 49 is a diagram showing a DSC measurement result of BMI-2-2 obtained in Example 8.

DESCRIPTION OF EMBODIMENTS

[Curable Compound]

The curable compound according to the present invention is represented by the following formula (1):

[Formula 5]

(1)

In the formula (1), $R^1$ and $R^2$ are identical or different and each represent a curable functional group; $D^1$ and $D^2$ are identical or different and each represent a single bond or a linking group; and L represents a divalent group having a repeating unit containing a structure represented by the following formula (I) and a structure represented by the following formula (II):

[Formula 6]

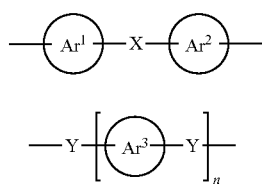
(I)
(II)

wherein $Ar^1$ to $Ar^3$ are identical or different and each represent a group made by eliminating two hydrogen atoms from a structural formula of an aromatic ring, or a group made by eliminating two hydrogen atoms from a structural formula in which two or more aromatic rings are bound through a single bond or a linking group; X represents —CO—, —S— or —SO$_2$—; each Y is identical or different and represents —S—, —SO$_2$—, —O—, —CO—, —COO— or —CONH—; and n represents an integer of 0 or more.

In the formula, $R^1$ and $R^2$ each represent a curable functional group. $R^1$ and $R^2$ may be identical or different. It is preferable that the curable functional group in $R^1$ and $R^2$ be a curable functional group having a cyclic imide structure, for example, a group represented by the following formula (r):

[Formula 7]

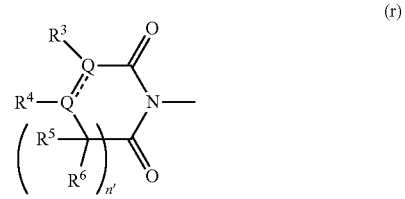
(r)

wherein the bond extending from the nitrogen atom in the formula is bound to $D^1$ or $D^2$.

In the above formula (r), Q each represents C or CH. Q may form a double bond. n' is an integer of 0 or more (for example, 0 to 3, preferably 0 or 1). $R^3$ to $R^6$ are identical or different, and each represent a hydrogen atom, a saturated or unsaturated aliphatic hydrocarbon group (preferably an alkyl group having 1 to 10 carbon atoms, an alkenyl group having 2 to 10 carbon atoms or an alkynyl group having 2 to 10 carbon atoms), an aromatic hydrocarbon group (preferably an aryl group having 6 to 10 carbon atoms, such as a phenyl group or a naphthyl group), or a group in which two or more groups selected from the above saturated or unsaturated aliphatic hydrocarbon group and the above aromatic hydrocarbon group are bound. Two groups selected from $R^3$ to $R^6$ may be bound to each other to form a ring with a neighboring carbon atom(s).

Examples of the ring which may be formed with a neighboring carbon atom(s) by mutually binding two groups selected from $R^3$ to $R^6$ include alicyclic rings having 3 to 20 carbon atoms and aromatic rings having 6 to 14 carbon atoms. Examples of the alicyclic rings having 3 to 20 carbon atoms include about 3 to 20-membered (preferably 3 to 15-membered, especially preferably 5 to 8-membered) cycloalkane rings such as a cyclopropane ring, a cyclobutane ring, a cyclopentane ring and a cyclohexane ring; about 3 to 20-membered (preferably 3 to 15-membered, especially preferably 5 to 8-membered) cycloalkene rings such as a cyclopentene ring and a cyclohexene ring; and bridged cyclic hydrocarbon groups such as a perhydronaphthalene ring, a norbornane ring, a norbornene ring, an adamantane ring, a tricyclo[5.2.1.0$^{2,6}$]decane ring and a tetracyclo [4.4.0.1$^{2,5}$.1$^{7,10}$]dodecane ring. The aromatic rings having 6 to 14 carbon atoms include a benzene ring and a naphthalene ring.

As the curable functional group having the above cyclic imide structure, above all, preferable is a curable functional group having a cyclic unsaturated imide structure or a curable functional group having a cyclic imide structure having an arylethynyl group; especially preferable is a group selected from groups represented by the following formulas (r-1) to (r-6); and particularly preferable is a group represented by the following formula (r-1) or (r-5):

[Formula 8]

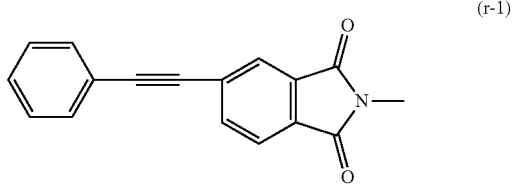
(r-1)

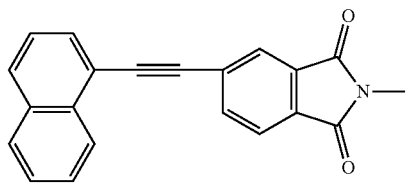
(r-2)

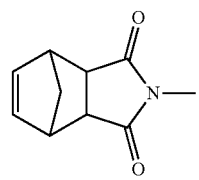
(r-3)

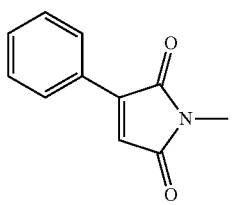
(r-4)

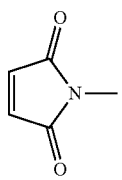
(r-5)

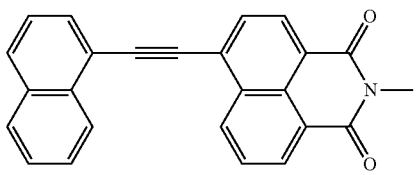
(r-6)

wherein a bond extending from a nitrogen atom in the formula is bound to $D^1$ or $D^2$.

One or two or more substituents may be bound to the groups represented by the above formulas (r-1) to (r-6). Examples of the substituents include alkyl groups having 1 to 6 carbon atoms, alkoxy groups having 1 to 6 carbon atoms and halogen atoms.

Examples of the alkyl groups having 1 to 6 carbon atoms include straight-chain or branched-chain alkyl groups such as a methyl group, an ethyl group, a propyl group, an isopropyl group, a butyl group, an isobutyl group, an s-butyl group, a t-butyl group, a pentyl group and a hexyl group.

Examples of the alkoxy groups having 1 to 6 carbon atoms include straight-chain or branched-chain alkoxy groups such as a methoxy group, an ethoxy group, a butoxy group and a t-butyloxy group.

In the formula (1), $D^2$ and $D^2$ are identical or different, and each represent a single bond or a linking group. Examples of the linking group include divalent hydrocarbon groups, divalent heterocyclic groups, a carbonyl group, an ether bond, an ester bond, a carbonate bond, an amido bond, an imido bond and groups made by linking a plurality of these groups and bonds.

The above divalent hydrocarbon groups include divalent aliphatic hydrocarbon groups, divalent alicyclic hydrocarbon groups and divalent aromatic hydrocarbon groups.

Examples of the above divalent aliphatic hydrocarbon groups include straight-chain or branched-chain alkylene groups having 1 to 18 carbon atoms and straight-chain or branched-chain alkenylene groups having 2 to 18 carbon atoms. Examples of the straight-chain or branched-chain alkylene groups having 1 to 18 carbon atoms include a methylene group, a methylmethylene group, a dimethylmethylene group, an ethylene group, a propylene group and a trimethylene group. Examples of the straight-chain or branched-chain alkenylene groups having 2 to 18 carbon atoms include a vinylene group, a 1-methylvinylene group, a propenylene group, a 1-butenylene group and a 2-butenylene group.

The above divalent alicyclic hydrocarbon groups include divalent alicyclic hydrocarbon groups having 3 to 18 carbon atoms, and examples thereof include cycloalkylene groups (including cycloalkylidene groups) such as a 1,2-cyclopentylene group, a 1,3-cyclopentylene group, a cyclopentylidene group, a 1,2-cyclohexylene group, a 1,3-cyclohexylene group, a 1,4-cyclohexylene group and a cyclohexylidene group.

Examples of the above divalent aromatic hydrocarbon groups include arylene groups having 6 to 14 carbon atoms, and examples thereof include a 1,4-phenylene group, a 1,3-phenylene group, a 4,4'-biphenylene group, a 3,3'-biphenylene group, a 2,6-naphthalenediyl group, a 2,7-naphthalenediyl group, a 1,8-naphthalenediyl group and an anthracenediyl group.

Heterocycles constituting the above divalent heterocyclic groups include aromatic heterocycles and nonaromatic heterocycles. Such heterocycles include 3 to 10-membered (preferably 4 to 6-membered) rings having carbon atoms and at least one heteroatom (for example, oxygen atom, sulfur atom or nitrogen atom) as atoms constituting the rings, and condensed rings thereof. The heterocycles specifically include heterocycles containing an oxygen atom as the heteroatom (for example, 3-membered rings such as an oxirane ring; 4-membered rings such as an oxetane ring; 5-membered rings such as a furan ring, a tetrahydrofuran ring, an oxazole ring, an isoxazol ring and a γ-butyrolactone ring; 6-membered rings such as a 4-oxo-4H-pyran ring, a tetrahydropyran ring and a morpholine ring; condensed rings such as a benzofuran ring, an isobenzofuran ring, a 4-oxo-4H-chromene ring, a chromane ring and an isochromane ring; and bridged rings such as a 3-oxatricyclo[4.3.1.1$^{4,8}$] undecan-2-one ring and a 3-oxatricyclo[4.2.1.0$^{4,8}$]nonan-2-one ring), heterocycles containing a sulfur atom as the heteroatom (for example, 5-membered rings such as a thiophene ring, a triazole ring, an isothiazole ring and a thiadiazole ring; 6-membered rings such as a 4-oxo-4H-thiopyran ring; and condensed rings such as a benzothiophene ring), and heterocycles containing a nitrogen atom as the heteroatom (for example, 5-membered rings such as a pyrrole ring, a pyrrolidine ring, a pyrazole ring, an imidazole ring and a triazole ring; 6-membered rings such as an isocyanuric ring, a pyridine ring, a pyridazine ring, a pyrimidine ring, a pyrazine ring, a piperidine ring and a piperazine ring; and condensed rings such as an indole ring, an indoline ring, a quinoline ring, an acridine ring, a naphthyridine ring, a quinazoline ring and a purine ring). The divalent heterocyclic groups are groups made by eliminating two hydrogen atoms from the structural formulas of the above heterocycles.

It is preferable, particularly from the viewpoint of providing a cured material excellent in heat resistance, that the above $D^1$ and $D^2$ each contain, above all, a divalent aromatic hydrocarbon group. As the divalent aromatic hydrocarbon group, preferable is a divalent aromatic hydrocarbon group having 6 to 14 carbon atoms; and more preferable is a group selected from groups represented by the following formulas (d-1) to (d-4); and particularly preferable is a group represented by the following formula (d-1) (1,2-phenylene group, 1,3-phenylene group or a 1,4-phenylene group).

[Formula 9]

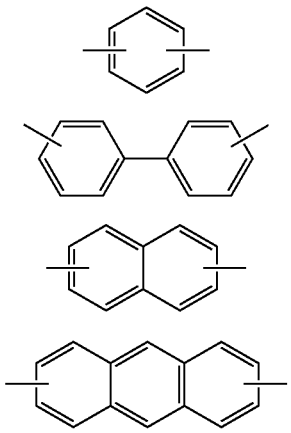

(d-1)
(d-2)
(d-3)
(d-4)

The above divalent aromatic hydrocarbon group may further have at least one group selected from the group consisting of a carbonyl group, an ether bond, an ester bond, a carbonate bond, an amido bond and an imido bond; and it is preferable to have, above all, an ether bond. Further it is preferable that the above ether bond be bound directly to L. Therefore, the $R^1$-$D^1$-group and $R^2$-$D^2$-group in the formula (1) are identical or different, and preferable is a group represented by the following formula (rd-1), (rd-2), (rd-3) or (rd-4); and especially preferable is a group represented by (rd-3) or (rd-4).

[Formula 10]

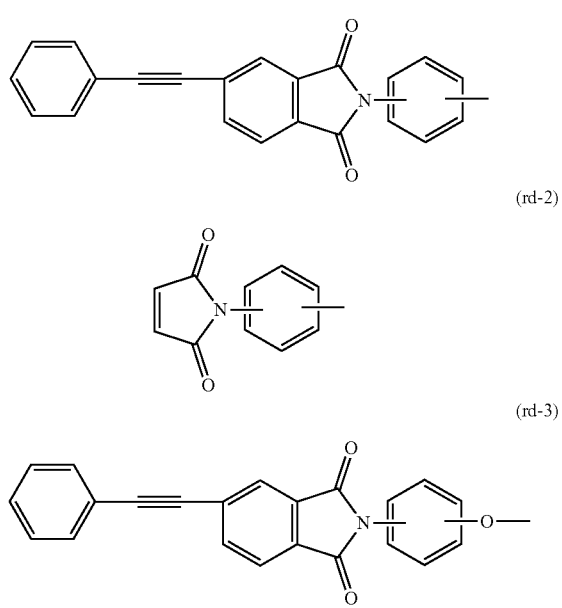

(rd-1)
(rd-2)
(rd-3)

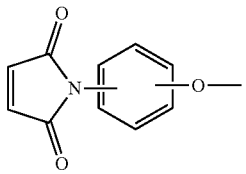

(rd-4)

wherein a bond extending from a phenylene group or an oxygen atom in the formulas is bound to L.

L in the formula (1) represents a divalent group having a repeating unit containing a structure represented by the above formula (I) and a structure represented by the above formula (II). That is, L represents a divalent group having a structure in which a unit containing a structure represented by the above formula (I) and a structure represented by the above formula (II) is repeated two or more times. $Ar^1$ to $Ar^3$ in the formula (I) and the formula (II) are identical or different and each represent a group made by eliminating two hydrogen atoms from a structural formula of an aromatic ring or a group made by eliminating two hydrogen atoms from a structural formula in which two or more aromatic rings are bound through a single bond or a linking group; X represents —CO—, —S— or —SO$_2$—; each Y is identical or different and represents —S—, —SO$_2$—, —O—, —CO—, —COO— or —CONH—, and n represents an integer of 0 or more, and is, for example, an integer of 0 to 5, preferably an integer of 1 to 5 and especially preferably an integer of 1 to 3.

Examples of the above aromatic ring (=aromatic hydrocarbon ring) include aromatic rings having 6 to 14 carbon atoms, such as benzene, naphthalene, anthracene and phenanthrene. In the present invention, it is preferable that the aromatic ring be, above all, an aromatic ring having 6 to 10 carbon atoms, such as benzene or naphthalene.

Examples of the above linking group include divalent hydrocarbon groups having 1 to 5 carbon atoms and groups made by replacing one or more hydrogen atoms of the divalent hydrocarbon group having 1 to 5 carbon atoms with halogen atoms.

Examples of the above divalent hydrocarbon groups having 1 to 5 carbon atoms include straight-chain or branched-chain alkylene groups having 1 to 5 carbon atoms such as a methylene group, a methylmethylene group, a dimethylmethylene group, a dimethylene group and a trimethylene group; straight-chain or branched-chain alkyenylene groups having 2 to 5 carbon atoms such as a vinylene group, 1-methylvinylene group and a propenylene group; and straight-chain or branched-chain alkynylene groups having carbon atoms 2 to 5 such as an ethynylene group, a propynylene group and 1-methylpropynylene group. In the present invention, above all, preferable is a straight-chain or branched-chain alkylene group having 1 to 5 carbon atoms, and especially preferable is a branched-chain alkylene group having 1 to 5 carbon atoms.

Therefore, the above $Ar^1$ to $Ar^3$ are identical or different and it is preferable that these be each a group made by eliminating two hydrogen atoms from a structural formula of an aromatic ring having 6 to 14 carbon atoms, or a group made by eliminating two hydrogen atoms from a structural formula in which two or more aromatic rings having 6 to 14 carbon atoms are bound through a single bond, a straight-chain or branched-chain alkylene group having 1 to 5 carbon atoms or a group made by replacing one or more hydrogen atoms of a straight-chain or branched-chain alkylene group having 1 to 5 carbon atoms with halogen atoms; and it is especially preferable that the $Ar^1$ to $Ar^3$ be each a group made by eliminating two hydrogen atoms from a structural formula of an aromatic ring having 6 to 14 carbon atoms, or a group made by eliminating two hydrogen atoms from a structural formula in which two or more aromatic rings having 6 to 14 carbon atoms are bound through a single bond, a branched-chain alkylene group having 1 to 5 carbon atoms or a group made by replacing one or more hydrogen atoms of a branched-chain alkylene group having 1 to 5 carbon atoms with halogen atoms.

The above $Ar^1$ to $Ar^3$ are identical or different and, it is particularly preferable that these be each a group selected from groups represented by the following formulas (a-1) to (a-5). Here, the positions where bonds in the following formulas are attached are not especially limited.

[Formula 11]

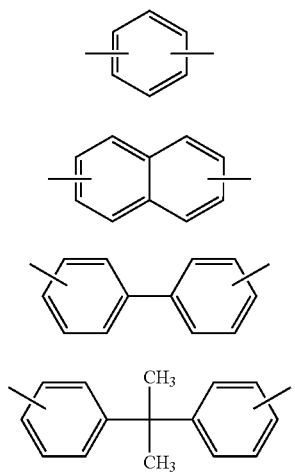

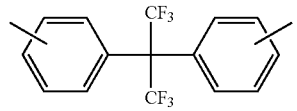

As $Ar^1$ and $Ar^2$ each in the formula (I), above all, preferable is a group made by eliminating two hydrogen atoms from a structural formula of an aromatic ring having 6 to 14 carbon atoms; and especially preferable is a group represented by the above formula (a-1) or (a-2). Then, it is preferable that X be, above all, —CO— or —SO$_2$—. It is particularly preferable that the structure represented by the formula (I) contain a structure derived from benzophenone.

The proportion of the amount of the structural unit derived from benzophenone to the total amount of the curable compound represented by the formula (1) is, for example, 5% by weight or more, preferably 10 to 62% by weight and especially preferably 15 to 60% by weight.

It is preferable that $Ar^3$ in the formula (II) be, above all, a group selected from groups represented by the above formulas (a-1), (a-4) and (a-5). Further, it is preferable that Y be, above all, —S—, —O— or —SO$_2$—. It is particularly preferable that the structure represented by the formula (II) contain a structure derived from at least one compound selected from hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone and bisphenol A.

The proportion of the amount of the structural unit derived from hydroquinone, resorcinol and bisphenol A to the total amount of the curable compound represented by the formula (1) is, for example, 5% by weight or more, preferably 10 to 55% by weight and especially preferably 15 to 53% by weight.

It is preferable, from the viewpoint of providing a cured material notably excellent in heat resistance, that L in the formula (1) is, above all, a divalent group represented by the following formula (l-1); and it is more preferable that L be a divalent group represented by the following formula (l-2) or (l-3).

[Formula 12]

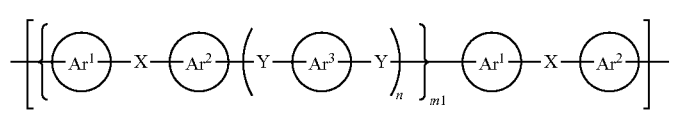

(I-1)

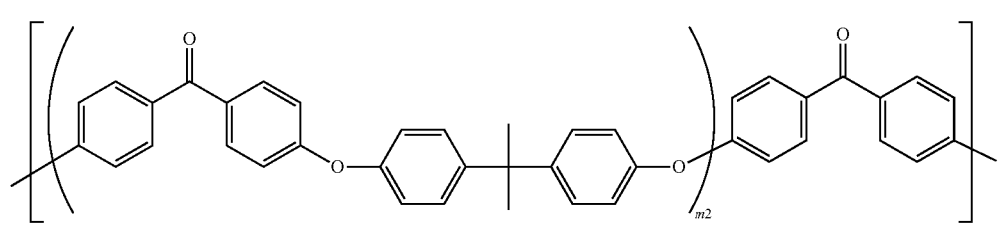

(I-2)

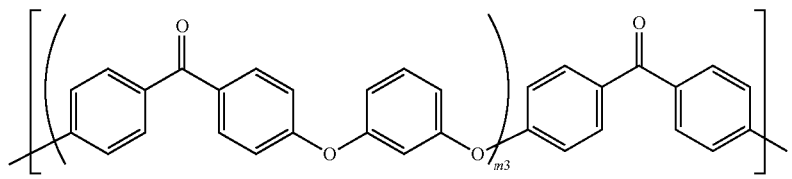

(I-3)

m1, m2 and m3 in the above formulas are the numbers of repeating units indicated in parentheses included in molecular chains (divalent groups represented by the above formulas (1-1), (1-2) and (1-3)), that is, average degrees of polymerization, which are, for example, 2 to 50, preferably 3 to 40, more preferably 4 to 30 and especially preferably 5 to 20. If m1, m2 and m3 are less than 2, the strength of an obtained cured material becomes insufficient. Here, the values of m1, m2 and m3 can be determined by GPC measurement and spectral analysis of NMR. n in the formula (1-1) is the same as in the formula (II).

The curable compound according to the present invention, since having the above constitution, can provide a cured material having a highly crosslinked structure (that is, having a high crosslinking density) and having a super heat resistance through a curing reaction using heat or the like.

Further, the curable compound according to the present invention, since having the above constitution, exhibits a solubility excellent to the following solvents.

Examples of the solvents include aromatic hydrocarbons such as benzene, toluene and xylene; hydrocarbon halides such as dichloromethane, chloroform, 1,2-dichloroethane, chlorobenzene, dichlorobenzene and benzotrifluoride; esters such as ethyl acetate; ethers such as tetrahydrofuran; ketones such as cyclohexanone; N-methyl-2-pyrrolidone, N,N-dimethylformamide, dimethyl sulfoxide, and mixtures thereof.

Among the curable compounds according to the present invention, a compound in which L in the formula (1) is a divalent group represented by the above formula (1-2) or (1-3) and m2 and m3 in the formula is 5 to 10, since melting at 300° C. or less (about 250° C.), can be melt molded at a lower temperature than PEEK and the like and is notably excellent in molding processability.

By contrast, when the average degree of polymerization of the molecular chain is below the above range, it is likely that an obtained cured material becomes brittle and mechanical properties decrease. Then, when the average degree of polymerization of the molecular chain is above the above range, it is likely that the molding processability reduces due to the decrease in the solubility to solvents, the rising in the melt viscosity, and the like.

The curable compound represented by the above formula (1) can be produced, for example, by a synthesis method described in Polymer p. 978 (1989). One example of a production method of the curable compound represented by the above formula (1) is shown in the below, but the production method is not especially limited thereto.

A compound represented by the following formula (1-1) can be produced through the following steps [1] to [3]. In the following formula, $Ar^1$ to $Ar^3$, X, Y, n, $R^3$ to $R^5$, Q and n' are the same as in the above. D represents a linking group, and Z represents a halogen atom. $n^3$ is an average degree of polymerization of the repeating unit, and is, for example, 3 to 50, preferably 4 to 30 and especially preferably 5 to 20. Among the curable compounds represented by the above formula (1), compounds other than the compound represented by the following formula (1-1) can also be produced according to the following method.

Step [1]: a compound represented by the following formula (2) and a compound represented by the following formula (3) as reaction base substances are allowed to react in the presence of a base to thereby obtain a compound represented by the following formula (4).

Step [2]: An aminoalcohol (a compound represented by the following formula (5)) is allowed to react with the compound represented by the following formula (4) to thereby obtain a diamine represented by the following formula (6).

Step [3]: A cyclic acid anhydride (a compound represented by the following formula (7)) is allowed to react with the diamine represented by the following formula (6) to thereby obtain a compound represented by the following formula (1-1).

[Formula 13]

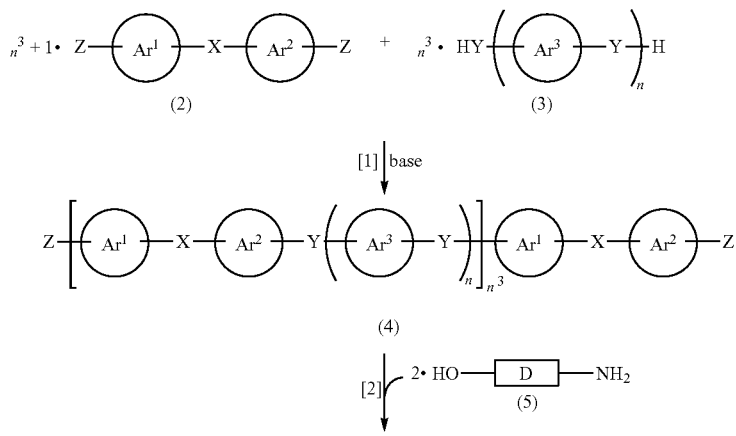

-continued

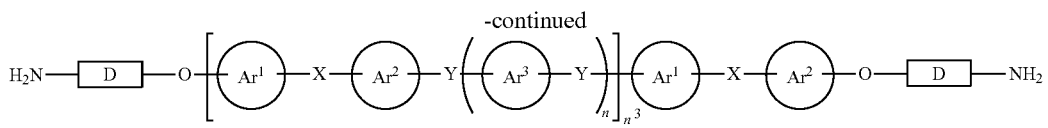

(6)

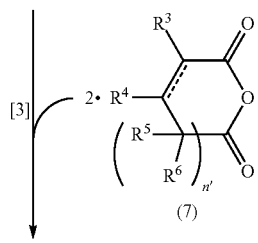

(7)

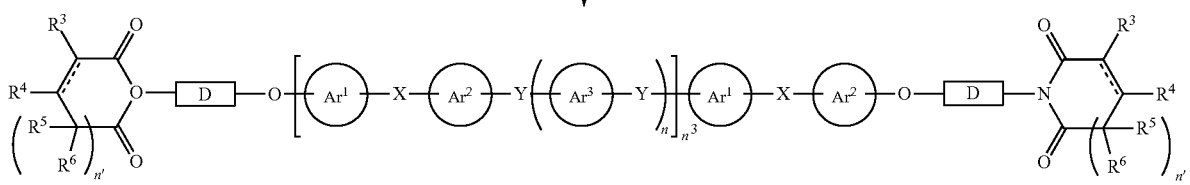

(1-1)

(Step [1])

Examples of the compound represented by the above formula (2) include halides of benzophenone, 2-naphthyl phenyl ketone and bis(2-naphthyl) ketone, and derivatives thereof.

The compound represented by the above formula (3) include hydroquinone, resorcinol, 2,6-naphthalenediol, 2,7-naphthalenediol, 1,5-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, bisphenol A, bisphenol F, bisphenol S, 2,5-dihydroxybiphenyl, and derivatives thereof. Among these, preferable are hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone and bisphenol A.

Examples of the above derivatives include compounds in which a substituent is bound to an aromatic hydrocarbon group of the compound represented by the above formula (2) or the compound represented by the above formula (3). Examples of the substituent include alkyl groups having 1 to 6 carbon atoms, alkoxy groups having 1 to 6 carbon atoms, and halogen atoms.

With respect to the amounts of the compound represented by the formula (2) and the compound represented by the formula (3) used, the compound represented by the formula (2) is usually in 1 mol or more to 1 mol of the compound represented by the formula (3), and it is desirable that the amount of the compound represented by the formula (2) used be regulated according to the average degree of polymerization of the molecular chain in a desired curable compound. It is preferable that for example, when the average degree of polymerization is 5, the compound represented by the formula (2) be used in 1.2 (1.18 to 1.22) mol to 1 mol of the compound represented by the formula (3); when the average degree of polymerization is 10, the compound represented by the formula (2) be used in 1.1 (1.08 to 1.12) mol; and when the average degree of polymerization is 20, the compound represented by the formula (2) be used in about 1.05 (1.04 to 1.06) mol.

As the compound represented by the formula (2), it is especially preferable to use at least a halide of benzophenone; and the amount of the halide of benzophenone used based on the total amount (100 mol %) of the compound represented by the formula (2) used is, for example, 10 mol % or more, preferably 30 mol % or more, especially preferably 50 mol % or more and most preferably 80 mol % or more. Here, the upper limit is 100 mol %.

As the compound represented by the formula (3), it is especially preferable to use at least one compound selected from, at least, hydroquinone, resorcinol and bisphenol A; the sum of the amounts of hydroquinone, resorcinol and bisphenol A used based on the total amount (100 mol %) of the compound represented by the formula (3) used is, for example, 10 mol % or more, preferably 30 mol % or more, especially preferably 50 mol % or more and most preferably 80 mol % or more. Here, the upper limit is 100 mol %.

The reaction of the compound represented by the formula (2) and the compound represented by the formula (3) is carried out in the presence of a base (for example, at least one selected from inorganic bases such as sodium hydroxide, potassium hydroxide, calcium hydroxide, sodium carbonate, potassium carbonate and sodium hydrogencarbonate, and organic bases such as pyridine and triethylamine). The amount of the base used can suitably be regulated according to the kind of the base. For example, in the case of using a diacidic base such as calcium hydroxide, the amount of the base used is, for example, about 1.0 to 2.0 mol to 1 mol of the compound represented by the formula (3).

Further, the reaction can be carried out in the presence of a solvent. As the solvent, there can be used, for example, an organic solvent such as N-methyl-2-pyrrolidone, dimethylformamide, dimethyl sulfoxide, acetone, tetrahydrofuran or toluene, or a mixed solvent of two or more thereof.

The amount of the above solvent used is, with respect to the total (weight) of the reaction base substances, for example, about 5 to 20 times in weight. When the amount of the solvent used exceeds the above range, the concentration of the reaction base substances decreases and the reaction velocity is likely to decrease.

The reaction atmosphere is not especially limited unless inhibiting the reaction, and there may be used any of, for example, an air atmosphere, a nitrogen atmosphere and an argon atmosphere.

The reaction temperature is, for example, about 100 to 200° C. The reaction time is, for example, about 5 to 24 hours. Further the reaction can be carried out in any method of a batch type, a semibatch type and a continuous type.

After the completion of the reaction, an obtained reaction product can be separated and refined, for example, by a separation means such as filtration, concentration, distillation, extraction, crystallization, adsorption, recrystallization or column chromatography, or a separation means in a combination thereof.

(Step [2])

Examples of the compound represented by the formula (5) include 4-aminophenol, 2-amino-6-hydroxynaphthalene, and regioisomers and derivatives thereof.

The amount of the compound represented by the formula (5) used can suitably be regulated according to the average degree of polymerization of the molecular chain in a desired curable compound. For example, in the case of an average degree of polymerization of 5, the amount used is about 0.4 to 0.6 mol to 1 mol of the compound represented by the formula (3); in the case of an average degree of polymerization of 10, the amount used is about 0.2 to 0.4 mol to 1 mol of the compound represented by the formula (3); and in the case of an average degree of polymerization of 20, the amount used is about 0.1 to 0.15 mol to 1 mol of the compound represented by the formula (3).

Since the reaction forms a hydrogen halide along with the progress of the reaction, carrying out the reaction in the presence of a base to trap the formed hydrogen halide is preferable in that the effect of promoting the progress of the reaction can be attained. Examples of the base include inorganic bases such as sodium hydroxide, potassium hydroxide, calcium hydroxide, sodium carbonate, potassium carbonate and sodium hydrogencarbonate, and organic bases such as pyridine and triethylamine. These can be used singly or in a combination of two or more.

The amount of the base used can suitably be regulated according to the kind of the base. For example, in the case of using a monoacidic base such as sodium hydroxide, the amount of the base used is, for example, about 1.0 to 3.0 mol to 1 mol of the compound represented by the above formula (5).

Then, the reaction can be carried out in the presence of a solvent. The same solvent as in step [1] can be used.

The reaction temperature is, for example, about 100 to 200° C. The reaction time is, for example, about 1 to 15 hours. Further the reaction can be carried out by any method of a batch type, a semibatch type and a continuous type.

After the completion of the reaction, an obtained reaction product can be separated and refined, for example, by a separation means such as filtration, concentration, distillation, extraction, crystallization, adsorption, recrystallization or column chromatography, or a separation means in a combination thereof.

(Step [3])

Examples of the above cyclic acid anhydride (the compound represented by the formula (7)) include maleic anhydride, 2-phenylmaleic anhydride, 4-phenylethynyl-phthalic anhydride, 4-(1-naphthylethynyl)-phthalic anhydride and bicyclo[2.2.1]hept-5-ene-2,3-dicarboxylic anhydride, and derivative thereof.

The amount of the above cyclic acid anhydride used can suitably be regulated according to the average degree of polymerization of the molecular chain in a desired curable compound. For example, in the case of an average degree of polymerization of 5, the amount used is about 0.4 to 0.8 mol to 1 mol of the compound represented by the formula (3); in the case of an average degree of polymerization of 10, the amount used is about 0.2 to 0.4 mol to 1 mol of the compound represented by the formula (3); and in the case of an average degree of polymerization of 20, the amount used is about 0.1 to 0.15 mol to 1 mol of the compound represented by the formula (3).

The reaction can be carried out in the presence of a solvent. The same solvent as used in step [1] can be used.

It is preferable that the reaction be carried out at room temperature (1 to 30° C.). The reaction time is, for example, about 1 to 30 hours. Further the reaction can be carried out by any method of a batch type, a semibatch type and a continuous type.

Then, in the reaction, removing water by-produced in the reaction by azeotropy using an azeotropic solvent of water (for example, toluene) or by use of a dehydrating agent (for example, acetic anhydride) is preferable in that the progress of the reaction can be promoted. Further it is preferable that the removal of the formed water by the dehydrating agent be carried out in the presence of a basic catalyst (for example, trimethylamine).

After the completion of the reaction, an obtained reaction product can be separated and refined, for example, by a separation means such as filtration, concentration, distillation, extraction, crystallization, adsorption, recrystallization or column chromatography, or a separation means in a combination thereof.

The exothermic peak temperature of the curable compound represented by the formula (1) is, though depending on the kind of the curable functional group, for example, 170 to 450° C., preferably 200 to 430° C. and especially preferably 220 to 420° C. The exothermic peak temperature can be determined by DSC measurement.

Since the exothermic peak temperature of the curable compound represented by the formula (1) is governed by the kind of the curable functional group, it is preferable that the curable functional group be selected according to a molding method to be adopted. For example, when the curable compound is molded in a film form by a cast method from a solution in which the curable compound is dissolved in a solvent, and cured, selection of a group represented by the above formula (r-5) as the curable functional group in the curable compound represented by the formula (1) is preferable; and in this case, a cured material can be formed by heating the cast curable compound at a temperature of about 250° C. On the other hand, when a group represented by the above formula (r-1) is selected as the curable functional group in the curable compound represented by the formula (1), the curable compound can be molded by being melted at a temperature of about 300° C. or less, and a cured material can be formed by heating the melted curable compound at a temperature of about 380° C.

Here, the heating may be carried out in the state that the temperature is held constant in the above temperature range, or may be carried out by stepwise changing the temperature in the above temperature range. It is preferable that the heating temperature be suitably regulated in the above range according to the heating time, and for example, if shortening of the heating time is desired, setting of the heating temperature on the high side is preferable. The curable compound according to the present invention, since having a structure represented by the above formula (1), can form a cured material (in detail, a cured material having a super heat resistance) without being decomposed even if being heated at a high temperature, and can form the cured material in better workability and efficiently by being heated at a high temperature for a short time. Here, a heating means is not especially limited, and a well-known and common means can be utilized.

Curing of the curable compound represented by the formula (1) can be carried out under normal pressure, or may be carried out under reduced pressure or under high pressure.

In the cured material of the curable compound represented by the formula (1), the 5%-weight loss temperature ($T_{d5}$) as measured at a temperature-rise rate of 10° C./min (in nitrogen) is, for example, 300° C. or more, more preferably 400° C. or more, especially preferably 450° C. or more and most preferably 500° C. or more. Here, the upper limit is, for example, 600° C., preferably 550° C. and especially preferably 530° C. Here, the 5%-weight loss temperature can be measured, for example, by TG/DTA (simultaneous measurement of differential calorimetry and thermogravimetry).

In the cured material of the curable compound represented by the formula (1), the 10%-weight loss temperature ($T_{d10}$) as measured at a temperature-rise rate of 10° C./min (in nitrogen) is, for example, 300° C. or more, more preferably 400° C. or more, especially preferably 480° C. or more and most preferably 500° C. or more. Here, the upper limit is, for example, 600° C. and preferably 550° C. Here, the 10%-weight loss temperature can be measured, for example, by TG/DTA (simultaneous measurement of differential calorimetry and thermogravimetry).

The relative dielectric constant of the cured material of the curable compound (curable composition) according to the present invention is not especially limited, but for example, being 6 or less (for example, 1 to 6) is desirable; being 5 or less (for example, 1 to 5) is more preferable; and being 4 or less (for example, 1 to 4) is still more preferable. Further the dielectric loss tangent of the cured material of the curable compound (curable composition) according to the present invention is not especially limited, but for example, being 0.05 or less (for example, 0.0001 to 0.05) is desirable; being 0.0001 to 0.03 is more preferable; and being 0.0001 to 0.015 is still more preferable. Here, the above "relative dielectric constant" and "dielectric loss tangent" mean values as measured according to JIS C2138 at a measurement frequency of 1 MHz at a measurement temperature of 23° C., or values as measured according to ASTM D2520 at a frequency of 1 GHz at 23° C.

The curable compound according to the present invention has good solvent solubility. Further the curable compound can be quickly cured by being subjected to a heat treatment and can form a cured material having super heat resistance as described above. Hence, the curable compound can be used as molding materials for composite materials to be used in a severe heat-resistant environment for electronic information, household appliances, cars, precision machines and the like, and as functional materials such as insulating materials and heat-resistant adhesives. Besides, the curable compound can be preferably used for encapsulants, coating agents, adhesives, inks, sealants, resists, forming materials [forming materials for, for example, substrate materials, electric insulating materials (insulating films and the like), laminated plates, composite materials (fiber-reinforced plastics, prepregs and the like), optical elements (lenses and the like), optical shaping materials, electronic papers, touch panels, solar cell substrates, optical waveguide materials, light guide plates, and holographic memory materials], and the like; and the curable compound can be preferably used particularly in applications to encapsulants covering semiconductor devices in highly heat-resistant and highly voltage-resistant semiconductor apparatuses (power semiconductors and the like), which conventional resin materials cannot meet. Further the curable compound of the present invention, since its cured material has a low relative dielectric constant and dielectric loss tangent, can be used suitably as an insulating material.

{Curable Composition}

The curable composition according to the present invention comprises one or two or more of the above curable compounds. The content (in the case of the two or more, the total amount thereof) of the above curable compounds based on the total amount of the curable composition according to the present invention is, for example, 30% by weight or more, preferably 50% by weight or more, especially preferably 70% by weight or more and most preferably 90% by weight or more. Here, the upper limit is 100% by weight. That is, the curable composition according to the present invention includes a composition composed only of the curable compounds.

The curable composition according to the present invention, in addition to the above curable compound, as required, may contain other components. As the other components, well-known and common additives can be used; examples thereof include curable compounds other than the compounds represented by the above formula (1), catalysts, fillers, organic resins (silicone resins, epoxy resins, fluororesins and the like), solvents, stabilizers (antioxidants, ultraviolet absorbents, light-resistant stabilizers, heat stabilizers and the like), flame retardants (phosphorus-based flame retardants, halogen-based flame retardants, inorganic flame retardants and the like), flame retardant auxiliary agents, reinforcing materials, nucleating agents, coupling agents, lubricants, waxes, plasticizers, mold lubricants, impact-resistance improving agents, hue improving agents, fluidity improving agents, colorants (dyes, pigments and the like), dispersants, antifoaming agents, defoaming agents, antibacterial agents, antiseptics, viscosity regulators and thickeners. These can be used singly or in a combination of two or more.

Although the curable composition according to the present invention is allowed to contain, as the curable compound, curable compounds other than the curable compounds represented by the above formula (1), the proportion of the curable compounds represented by the above formula (1) in all curable compounds contained in the curable composition is, for example, 70% by weight or more, preferably 80% by weight or more and especially preferably 90% by weight or more. Here, the upper limit is 100% by weight.

Then, the curable composition according to the present invention, without containing any crosslinking agent nor any curing accelerator (for example, even if the total content of the crosslinking agent and the curing accelerator based on the total amount of the curable composition according to the present invention is, for example, 3% by weight or less, preferably less than 1% by weight), can quickly form a cured material. Hence, an obtained cured material has a super heat resistance. Further, since in the cured material, the contents of the unreacted curing accelerator and decomposed substances of the curing accelerator can be suppressed remarkably low, generation of outgasses derived therefrom can be suppressed.

The curable composition according to the present invention, since comprising the above curable compound, by being subjected to a heat treatment, can be quickly cured and form a cured material having a super heat resistance. Here, the heat treatment condition can suitably be established in the same range as in the above-mentioned curing condition of the curable compound.

The curable composition according to the present invention can suitably be used as molding materials for composite materials (fiber-reinforced plastics, prepregs and the like) and functional materials such as insulating materials and heat-resistant adhesives to be used in a severe heat-resistant environment for electronic information, household appliances, cars, precision machines, aircrafts, devices for space industries and the like. Besides, the curable composition can be preferably used for encapsulants, coating materials, inks, sealants, resists, forming materials [forming materials for, for example, car components such as thrust washers, oil filters, seals, bearings, gears, cylinder head covers, bearing retainers, intake manifolds and pedals; components of semiconductor and liquid crystal producing apparatuses, such as substrate materials, electric insulating materials (insulating films and the like), laminated plates, electronic papers, touch panels, solar cell substrates, optical waveguide materials, light guide plates, holographic memories, silicon wafer carriers, IC chip trays, electrolytic capacitor trays and insulating films; optical components such as lenses; compressor components such as pumps, valves and seals; cabin interior trim components of aircrafts; medical device components and components of food and beverage producing facilities, such as sterilizing devices, columns and piping; and such members for electric and electronic devices as represented by housings to be used for personal computers, cell phones and the like, and keyboard supporters being members to support keyboards inside personal computers] and the like; and the curable composition can be preferably used particularly in applications to encapsulants covering semiconductor devices in highly heat-resistant and highly voltage-resistant semiconductor apparatuses (power semiconductors and the like), which conventional resin materials cannot meet. Further the curable composition according to the present invention, since its cured material has a low relative dielectric constant and dielectric loss tangent, can be used suitably as an insulating material, and can be used especially suitably as an interlayer insulating layer in electric devices or electronic devices.

(Molding)

The molding according to the present invention comprises a cured material obtained by curing the above curable composition. A method for forming the molding is not especially limited, but for example, involves applying or filling the curable composition on or in a supporter, and curing the curable composition by a heat treatment or the like. Here, the heat treatment condition can suitably be established in the same range as in the above-mentioned curing condition of the curable compound.

Examples of the molding according to the present invention include composite materials, insulating materials, heat-resistant adhesives and the like to be used in a severe heat-resistant environment for electronic information, household appliances, cars, precision machines, aircrafts, devices for space industries and the like. The molding also include semiconductor devices in highly heat-resistant and highly voltage-resistant semiconductor apparatuses (power semiconductors and the like), and electric devices or electronic devices.

EXAMPLES

Hereinafter, the present invention will be described more specifically by way of Examples, but the present invention is not any more limited to these Examples.

Then, measurements were carried out under the following conditions.

<NMR Measurement>
Measuring apparatus: BRUKER 400 MHz/54 mm or BRUKER AVANCE 600 MHz
Measuring solvent: heavy DMSO, heavy chloroform or a mixed liquid of heavy chloroform/pentafluorophenol (PFP) =2/1 (wt/wt)
Chemical shift: TMS was used as the reference
<GPC Measurement>
Apparatus: pump: "LC-20AD" (manufactured by Shimadzu Corp.)
Detector: RID-10A (manufactured by Shimadzu Corp.) or TDA-301 and UV 2501 (manufactured by Viscotek Co.)
Solvent: THF or chloroform
Column: Shodex GPC KF-801+KF-801+KF-803+KF-806M
Flow rate: 1.0 mL/min
Temperature: 40° C.
Sample concentration: 0.1% (wt/vol)
In terms of standard polystyrene
<DSC Measurement>
Apparatus: TA Q20
Temperature-rise rate: 10° C./min
Atmosphere: a nitrogen atmosphere
<TGA Measurement>
Apparatus: NETZSCH TG209F3
Temperature-rise rate: 10° C./min
Atmosphere: a nitrogen atmosphere
<IR Measurement>
Apparatus: Perkin Elmer Spectrum RX1 (ATR method)

Preparation Example 1 (Synthesis of Diamine-2-1)

Step 1: 6.865 g of 4,4'-difluorobenzophenone (4,4'-DFBP), 5.985 g of bisphenol A, 5.427 g of anhydrous potassium carbonate ($K_2CO_3$), 50 mL of N-methylpyrrolidone and 25 mL of toluene were charged in a 100-mL flask (three-necked) equipped with a stirring apparatus, a nitrogen introducing tube and Dean-Stark apparatus, and heated under stirring in a nitrogen atmosphere while toluene was refluxed at 130 to 140° C. for 4 hours. Thereafter, the resultant was further heated at 170 to 180° C. to distil away toluene. The resultant was continuously stirred at 170 to 180° C. for 10 hours, and thereafter returned to room temperature.

Step 2: 1.144 g of 4-aminophenol (4-AP), 1.447 g of anhydrous potassium carbonate, 5 mL of N-methylpyrrolidone and 25 mL of toluene were added to the flask in which a product obtained through step 1 was present, and again heated under stirring in a nitrogen atmosphere while toluene was refluxed at 130 to 140° C. for 3 hours. Thereafter, the resultant was heated at 170 to 180° C. to distil away toluene, and further continuously stirred for 4 hours at the same temperature being held. Thereafter, the resultant was cooled to room temperature; the resultant reaction liquid was added to 1,500 mL of ethanol, and filtered to thereby obtain a powdery solid. The powdery solid was washed with ethanol and water repeatedly, and thereafter vacuum dried at 100° C. for 8 hours to thereby obtain a powdery solid (Diamine-2-1, a compound represented by the following formula (6-1) wherein n1 was 6.8, yield: 95%).

[Formula 14]

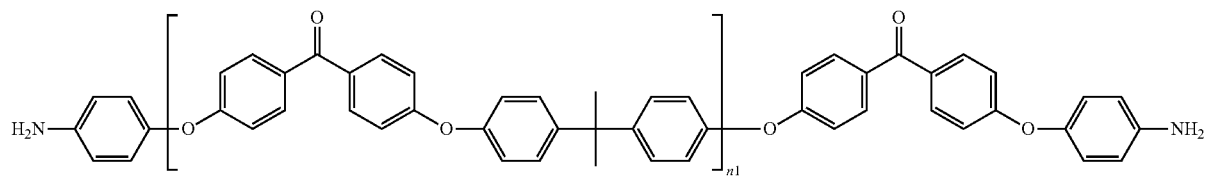

(6-1)

Preparation Example 2 (Synthesis of Diamine-2-2)

A powdery solid (Diamine-2-2, a compound represented by the above formula (6-1) wherein n1 was 9.7, yield: 95%) was obtained as in Preparation Example 1, except for, in step 1, altering the amount of 4,4'-difluorobenzophenone used to 6.586 g, the amount of bisphenol A used to 6.264 g and the amount of anhydrous potassium carbonate used to 5.680 g, and in step 2, altering the amount of 4-aminophenol used to 0.599 g, and the amount of anhydrous potassium carbonate used to 0.599 g.

Preparation Example 3 (Synthesis of Diamine-1-1)

Step 1: 8.905 g of 4,4'-difluorobenzophenone, 3.745 g of resorcinol, 7.040 g of anhydrous potassium carbonate, 50 mL of N-methylpyrrolidone and 25 mL of toluene were charged in a 100-mL flask (three-necked) equipped with a stirring apparatus, a nitrogen introducing tube and a Dean-Stark apparatus, and heated under stirring in a nitrogen atmosphere while toluene was refluxed at 130 to 140° C. for 4 hours. Thereafter, the resultant was further heated at 170 to 180° C. to distil away toluene. The resultant was further continuously stirred at 170 to 180° C. for 10 hours, and thereafter returned to room temperature.

Step 2: 1.485 g of 4-aminophenol, 1.878 g of anhydrous potassium carbonate, 5 mL of N-methylpyrrolidone and 25 mL of toluene were added to the flask in which a product obtained through step 1 was present. The resultant was again heated under stirring in a nitrogen atmosphere while toluene was refluxed at 130 to 140° C. for 3 hours. Thereafter, the resultant was heated at 170 to 180° C. to distil away toluene, and continuously stirred for 4 hours at the same temperature being held. Thereafter, the resultant was cooled to room temperature; the resultant reaction liquid was added to 1,500 mL of ethanol, and filtered to thereby obtain a powdery solid. The powdery solid was washed with ethanol and water repeatedly, and thereafter vacuum dried at 100° C. for 8 hours to thereby obtain a powdery solid (Diamine-1-1, a compound represented by the following formula (6-2) wherein n2 was 6.1, yield: 95%).

[Formula 15]

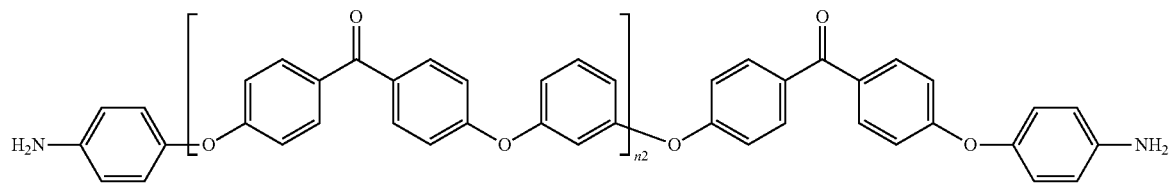

(6-2)

Preparation Example 4 (Synthesis of Diamine-1-2)

A powdery solid (Diamine-1-2, a compound represented by the above formula (6-2) wherein n2 was 8.8, yield: 93%) was obtained as in Preparation Example 3, except for, in step 1, altering the amount of 4,4'-difluorobenzophenone used to 9.121 g, the amount of resorcinol used to 4.185 g and the amount of anhydrous potassium carbonate used to 7.867 g, and in step 2, altering the amount of 4-aminophenol used to 0.829 g, and the amount of anhydrous potassium carbonate used to 1.049 g.

$^1$H-NMR spectra and FTIR spectra of the powdery solids obtained in Preparation Examples 1 to 4 are shown in FIGS. 1 to 6. Further the number-average molecular weights, the weight-average molecular weights and the average degrees of polymerization determined by gel permeation chromatography (GPC) (solvent: THF, in terms of standard polystyrenes) are shown in the following Table.

TABLE 1

| | | Number-Average Molecular Weight (Mn) | Weight-Average Molecular Weight (Mw) | Average Degree of Polymerization (n) |
|---|---|---|---|---|
| Preparation Example 1 | Diamine-2-1 | 3,150 | 5,500 | 6.8 |
| Preparation Example 2 | Diamine-2-2 | 4,350 | 9,350 | 9.7 |
| Preparation Example 3 | Diamine-1-1 | 2,160 | 3,640 | 6.1 |

TABLE 1-continued

| | | Number-Average Molecular Weight (Mn) | Weight-Average Molecular Weight (Mw) | Average Degree of Polymerization (n) |
|---|---|---|---|---|
| Preparation Example 4 | Diamine-1-2 | 2,940 | 6,320 | 8.8 |

Example 1 (Synthesis of BEI-2-1)

4.550 g of Diamine-2-1 obtained in Preparation Example, 1.395 g of 4-phenylethynyl-phthalic anhydride and 33 mL of N-methylpyrrolidone were charged in a 50-mL flask (three-necked) equipped with a stirring apparatus, a nitrogen intro-

[Formula 17]

BEI-1

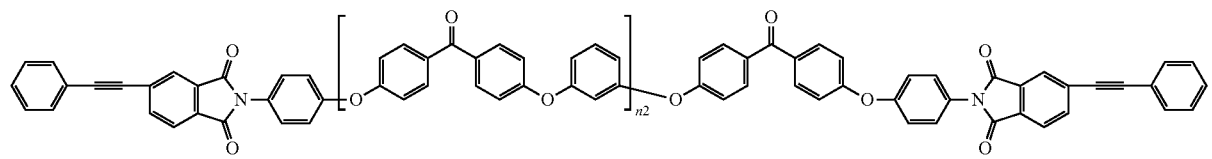

ducing tube and a drying tube, and stirred in a nitrogen atmosphere at room temperature for 18 hours. Thereafter, the drying tube was exchanged for a Dean-Stark apparatus and 25 mL of toluene was added, and thereafter, the resultant was heated to 130 to 140° C. and toluene was refluxed for 5 hours. Then, the resultant was heated to 170 to 180° C. to distil away toluene, and continuously stirred for 4 hours. Thereafter, the resultant reaction liquid was cooled to room temperature, and added to 1,500 mL of ethanol, and filtered to thereby obtain a powdery solid. The powdery solid was washed with ethanol and water repeatedly, and vacuum dried at 100° C. for 8 hours to thereby obtain a powdery solid (BEI-2-1, a compound represented by the following formula (BEI-2), yield: 90%). A $^1$H-NMR spectrum of BEI-2-1 is shown in FIG. 7 and an FTIR spectrum thereof is shown in FIG. 8.

[Formula 16]

BEI-2

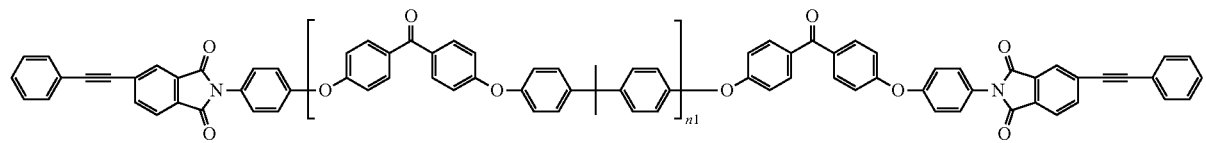

$^1$H-NMR (CDCl$_3$) δ: 1.71 (s), 7.02 (m), 7.11 (d, J=8.8 Hz), 7.21 (d, J=8.8 Hz), 7.27 (m), 7.41 (m), 7.48 (d, J=8.8 Hz), 7.58 (m), 7.81 (m), 7.93 (m), 8.08 (s)

Example 2 (Synthesis of BEI-2-2)

A powdery solid (BEI-2-2, a compound represented by the above formula (BEI-2), yield: 91%) was obtained as in Example 1, except for using 4.599 g of Diamine-2-2 obtained in Preparation Example in place of Diamine-2-1, and 0.766 g of 4-phenylethynyl-phthalic anhydride. A $^1$H-NMR spectrum of BEI-2-2 is shown in FIG. 7 and an FTIR spectrum thereof is shown in FIG. 9.

$^1$H-NMR (CDCl$_3$) δ: 1.71 (s), 7.02 (m), 7.11 (d, J=8.8 Hz), 7.21 (d, J=8.8 Hz), 7.26 (m), 7.40 (m), 7.48 (d, J=8.8 Hz), 7.58 (m), 7.80 (m), 7.93 (m), 8.08 (s)

Example 3 (Synthesis of BEI-1-1)

A powdery solid (BEI-1-1, a compound represented by the following formula (BEI-1), yield: 90%) was obtained as in Example 1, except for using 4.571 g of Diamine-1-1 obtained in Preparation Example in place of Diamine-2-1, and 1.852 g of 4-phenylethynyl-phthalic anhydride. A $^1$H-NMR spectrum of BEI-1-1 is shown in FIG. 10 and an FTIR spectrum thereof is shown in FIG. 11.

$^1$H-NMR (CDCl$_3$) δ: 6.83 (m), 6.90 (m), 7.09 (m), 7.21 (d, J=8.8 Hz), 7.39 (m), 7.48 (d, J=8.8 Hz), 7.58 (m), 7.81 (m), 7.92 (m), 8.08 (s)

Example 4 (Synthesis of BEI-1-2)

A powdery solid (BEI-1-2, a compound represented by the above formula (BEI-1), yield: 92%) was obtained as in Example 1, except for using 4.607 g of Diamine-1-2 obtained in Preparation Example in place of Diamine-2-1, and 1.046 g of 4-phenylethynyl-phthalic anhydride. A $^1$H-NMR spectrum of BEI-1-2 is shown in FIG. 10 and an FTIR spectrum thereof is shown in FIG. 12.

$^1$H-NMR (CDCl$_3$) δ: 6.83 (m), 6.90 (m), 7.09 (m), 7.21 (d, J=8.8 Hz), 7.39 (m), 7.48 (d, J=8.8 Hz), 7.58 (m), 7.81 (m), 7.92 (m), 8.07 (s)

Example 5 (Synthesis of BMI-2-1)

4.550 g of Diamine-2-1 obtained in Preparation Example, 0.551 g of maleic anhydride and 33 mL of N-methylpyrrolidone were charged in a 50-mL (three-necked) flask equipped with a stirring apparatus, a nitrogen introducing tube and a drying tube, and stirred in a nitrogen atmosphere at room temperature for 24 hours. Thereafter, 4.215 g of acetic anhydride and 1.405 g of trimethylamine were added, and stirred at 60° C. for 6 hours. Thereafter, the resultant reaction liquid was returned to room temperature, and thereafter added to 1,500 mL of ethanol, and filtered to thereby obtain a powdery solid. The powdery solid was washed with ethanol and water repeatedly, and vacuum dried at 100° C. for 8 hours to thereby obtain a powdery solid (BMI-2-1, a compound represented by the following formula (BMI-2), yield: 90%). A $^1$H-NMR spectrum of BMI-2-1 is shown in FIG. 13.

$^1$H-NMR (CDCl$_3$) δ: 1.71 (s), 6.87 (s), 7.02 (m), 7.09 (m), 7.17 (d, J=8.8 Hz), 7.26 (m), 7.37 (d, J=8.8 Hz), 7.80 (m)

obtained through step 1 was present, and again heated under stirring in an argon atmosphere while toluene was refluxed at 130 to 140° C. for 3 hours. Thereafter, the resultant was heated at 170 to 180° C. to distil away toluene, and further continuously stirred for 4 hours at the same temperature being held. Thereafter, the resultant was cooled to room temperature; the resultant reaction liquid was added to 5,000 mL of methanol, and filtered to thereby obtain a powdery solid. The powdery solid was washed with methanol and

[Formula 18]

BMI-2

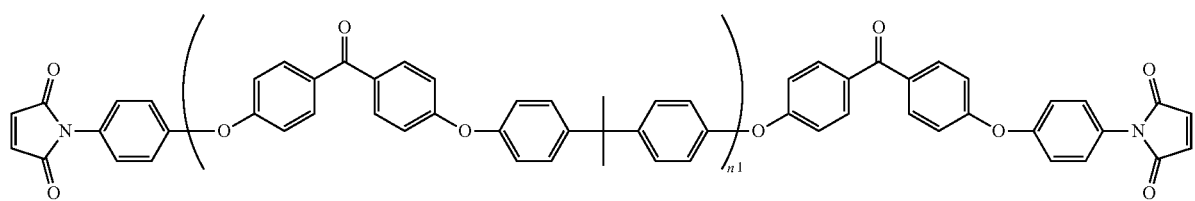

Example 6 (Synthesis of BMI-1-1)

A powdery solid (BMI-1-1, a compound represented by the following formula (BMI-1), yield: 90%) was obtained as in Example 5, except for using 4.571 g of Diamine-1-1 in place of Diamine-2-1, and altering the amount of maleic anhydride used to 0.733 g. A $^1$H-NMR spectrum of BMI-1-1 is shown in FIG. 14.

$^1$H-NMR (CDCl$_3$) δ: 6.88 (m), 7.08 (d, J=8.0 Hz), 7.17 (d, J=8.0 Hz), 7.39 (m), 7.81 (d, J=8.0 Hz)

water repeatedly, and thereafter dried at 100° C. for 8 hours to thereby obtain 37.461 g of a powdery solid (Diamine-1-3).

Step 3: 0.878 g of Diamine-1-3 obtained in step 2, 4.943 g of maleic anhydride and 240 mL of N-methylpyrrolidone were charged in a 500-mL flask (three-necked) equipped with a stirring apparatus and an argon introducing tube, and stirred in an argon atmosphere at room temperature for 18 hours. Thereafter, 8.576 g of acetic anhydride and 0.689 g of sodium acetate were added, and stirred at 60° C. for 6 hours.

[Formula 19]

BMI-1

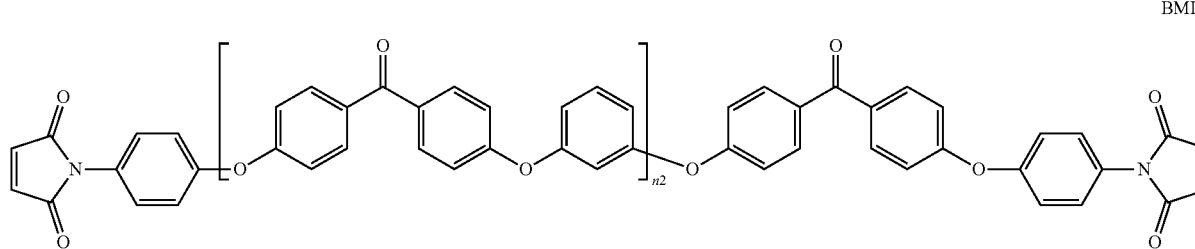

Example 7 (Synthesis of BMI-1-2)

Step 1: 31.443 g of 4,4'-difluorobenzophenone, 13.223 g of resorcinol, 29.894 g of anhydrous potassium carbonate, 180 mL of N-methylpyrrolidone and 90 mL of toluene were charged in a 500-mL flask (tree-necked) equipped with a stirring apparatus, an argon introducing tube and a Dean-Stark apparatus, and heated under stirring in an argon atmosphere while toluene was refluxed at 130 to 140° C. for 4 hours. Thereafter, the resultant was further heated at 170 to 180° C. to distil away toluene. The resultant was further continuously stirred at 170 to 180° C. for 10 hours, and thereafter returned to room temperature.

Step 2: 5.233 g of 4-aminophenol, 6.628 g of anhydrous potassium carbonate, 18 mL of N-methylpyrrolidone and 90 mL of toluene were added to the flask in which a product The resultant reaction liquid was returned to room temperature, and thereafter added to 5,000 mL of methanol to thereby obtain a powdery solid. The powdery solid was washed with methanol and water repeatedly, thereafter dried at 100° C. for 8 hours to thereby obtain 28.434 g of BMI-1-2. The number-average molecular weight and the degree of polymerization calculated from a GPC measurement of BMI-1-2, the degree of polymerization calculated from the integrated intensity ratio of signals of a $^1$H-NMR spectrum, and Tg obtained from a DSC measurement are shown in Table 4. Further the $^1$H-NMR spectrum of BMI-1-2 is shown in FIG. 15; an IR spectrum thereof is shown in FIG. 46; and the DSC measurement result is shown in FIG. 48.

$^1$H-NMR (CDCl$_3$/PFP=2/1) δ: 6.90 (m), 6.98 (d, J=7.9 Hz), 7.06 (s), 7.10 (s), 7.12 (m), 7.15 (d, 8.3), 7.38 (d, 9.8), 7.47 (dt, J=9.3 Hz, 3.2 Hz), 7.85 (d, J=8.7 Hz)

Example 8 (Synthesis of BMI-2-2)

Step 1: 10.476 g of 4,4'-difluorobenzophenone, 9.134 g of bisphenol A, 8.294 g of anhydrous potassium carbonate, 60 mL of N-methylpyrrolidone and 30 mL of toluene were charged in a 200-mL flask (tree-necked) equipped with a stirring apparatus, an argon introducing tube and a Dean-Stark apparatus, and heated under stirring in an argon atmosphere while toluene was refluxed at 130 to 140° C. for 4 hours. Thereafter, the resultant was further heated at 170 to 180° C. to distil away toluene. The resultant was further continuously stirred at 170 to 180° C. for 10 hours, and thereafter returned to room temperature.

Step 2: 1.744 g of 4-aminophenol, 2.208 g of anhydrous potassium carbonate, 6 mL of N-methylpyrrolidone and 30 mL of toluene were added to the flask in which a product obtained through step 1 was present, and again heated under stirring in an argon atmosphere while toluene was refluxed at 130 to 140° C. for 3 hours. Thereafter, the resultant was heated at 170 to 180° C. to distil away toluene, and further continuously stirred for 4 hours at the same temperature being held. Thereafter, the resultant reaction liquid was cooled to room temperature, and added to 2,000 mL of methanol, and filtered to thereby obtain a powdery solid. The powdery solid was washed with methanol and water repeatedly, and thereafter dried at 100° C. for 8 hours to thereby obtain 16.519 g of a powdery solid (Diamine-2-3).

Step 3: 9.100 g of Diamine-2-3 obtained in step 2, 1.102 g of maleic anhydride and 80 mL of N-methylpyrrolidone were charged in a 200-mL flask (three-necked) equipped with a stirring apparatus and an argon introducing tube, and stirred in an argon atmosphere at room temperature for 18 hours. Thereafter, 1.913 g of acetic anhydride and 0.154 g of sodium acetate were added, and stirred at 60° C. for 6 hours. The resultant reaction liquid was returned to room temperature, and thereafter added to 1,500 mL of methanol to thereby obtain a powdery solid. The powdery solid was washed with methanol and water repeatedly, thereafter dried at 100° C. for 8 hours to thereby obtain 8.730 g of BMI-2-2. The number-average molecular weight and the degree of polymerization calculated from a GPC measurement of BMI-2-2, the degree of polymerization calculated from the integrated intensity ratio of signals of a $^1$H-NMR spectrum thereof, and Tg obtained from a DSC measurement thereof are shown in Table 4. Further the $^1$H-NMR spectrum of BMI-2-2 is shown in FIG. 16; an IR spectrum thereof is shown in FIG. 47; and the DSC measurement result is shown in FIG. 49.

$^1$H-NMR (CDCl$_3$) δ: 1.71 (s), 6.84 (s), 6.99 (d, J=7.1 Hz), 7.03 (m), 7.07 (d, J=10.1 Hz), 7.15 (d, J=8.3 Hz), 7.26 (d, J=8.3 Hz), 7.36 (d, J=9.4 Hz), 7.78 (d, J=7.9 Hz), 7.80 (d, J=7.9 Hz)

Example 9 (Synthesis of BMI-3)

Steps 1 and 2: 13.533 g of a powdery solid (Diamine-3) was obtained by carrying out the same operation as in Example 8, except for using 2,6-naphthalenediol in place of bisphenol A, and setting the amounts of 2,6-naphthalenediol, 4,4'-difluorobenzophenone and anhydrous potassium carbonate used at those indicated in Table 2.

Step 3: 10.854 g of BMI-3 was obtained by carrying out the same operation as in Example 8, except for using the Diamine-3 in place of Diamine-2-3, and setting the amounts of Diamine-3, maleic anhydride, acetic anhydride and sodium acetate used at those indicated in Table 3. An IR spectrum of BMI-3 is shown in FIG. 27 and a DSC measurement result thereof is shown in FIG. 35. Then, the degree of polymerization calculated from the integrated intensity ratio of signals of a $^1$H-NMR spectrum of BMI-3, and Tg obtained from the DSC measurement are shown in Table 4. The $^1$H-NMR spectrum of BMI-3 is shown in FIG. 17.

$^1$H-NMR (CDCl$_3$) δ: 7.06 (s), 7.08 (m), 7.13 (s), 7.19 (m), 7.39 (d, J=8.3 Hz), 7.84 (m)

Example 10 (Synthesis of BMI-4)

Steps 1 and 2: 14.946 g of a powdery solid (Diamine-4) was obtained by carrying out the same operation as in Example 8, except for using 2,7-naphthalenediol in place of bisphenol A, and setting the amounts of 2,7-naphthalenediol, 4,4'-difluorobenzophenone and anhydrous potassium carbonate used at those indicated in Table 2.

Step 3: 12.457 g of BMI-4 was obtained by carrying out the same operation as in Example 8, except for using the Diamine-4 in place of Diamine-2-3, and setting the amounts of Diamine-4, maleic anhydride, acetic anhydride and sodium acetate used at those indicated in Table 3. An IR spectrum of BMI-4 is shown in FIG. 28 and a DSC measurement result thereof is shown in FIG. 36. Then, the number-average molecular weight and the degree of polymerization calculated from a GPC measurement of BMI-4, the degree of polymerization calculated from the integrated intensity ratio of signals of a $^1$H-NMR spectrum, and Tg obtained from the DSC measurement are shown in Table 4. The $^1$H-NMR spectrum of BMI-4 is shown in FIG. 18.

$^1$H-NMR (CDCl$_3$/PFP=2/1) δ: 7.05 (s), 7.11 (d, J=8.7 Hz), 7.16 (d, J=9.6 Hz), 7.17 (d, J=7.9 Hz), 7.27 (d, J=7.2 Hz), 7.38 (d, J=8.7 Hz), 7.43 (s), 7.88 (d, J=9.1 Hz), 7.93 (d, J=8.3 Hz)

Example 11 (Synthesis of BMI-5)

Steps 1 and 2: 14.787 g of a powdery solid (Diamine-5) was obtained by carrying out the same operation as in Example 8, except for using 4,4'-dihydroxyphenyl ether in place of bisphenol A, and setting the amounts of 4,4'-dihydroxyphenyl ether, 4,4'-difluorobenzophenone and anhydrous potassium carbonate used at those indicated in Table 2.

Step 3: 12.468 g of BMI-5 was obtained by carrying out the same operation as in Example 8, except for using the Diamine-5 in place of Diamine-2-3, and setting the amounts of Diamine-5, maleic anhydride, acetic anhydride and sodium acetate used at those indicated in Table 3. An IR spectrum of BMI-5 is shown in FIG. 29 and a DSC measurement result thereof is shown in FIG. 37. Then, the degree of polymerization calculated from the integrated intensity ratio of signals of a $^1$H-NMR spectrum of BMI-5, and Tg obtained from the DSC measurement are shown in Table 4. The $^1$H-NMR spectrum of BMI-5 is shown in FIG. 19.

$^1$H-NMR (CDCl$_3$/PFP=2/1) δ: 7.06 (s), 7.11 (d, J=10.1 Hz), 7.16 (d, J=9.4 Hz), 7.21 (m), 7.34 (d, J=9.4 Hz), 7.55 (s), 7.87 (m), 7.89 (m)

Example 12 (Synthesis of BMI-6)

Steps 1 and 2: 13.602 g of a powdery solid (Diamine-6) was obtained by carrying out the same operation as in Example 8, except for using 4,4'-dihydroxybenzophenone in place of bisphenol A, and setting the amounts of 4,4'- dihydroxybenzophenone, 4,4'-difluorobenzophenone and anhydrous potassium carbonate used at those indicated in Table 2.

Step 3: 10.435 g of BMI-6 was obtained by carrying out the same operation as in Example 8, except for using the Diamine-6 in place of Diamine-2-3, and setting the amounts of Diamine-6, maleic anhydride, acetic anhydride and sodium acetate used at those indicated in Table 3. An IR spectrum of BMI-6 is shown in FIG. 30 and a DSC measurement result thereof is shown in FIG. 38. Then, the degree of polymerization calculated from the integrated intensity ratio of signals of a $^1$H-NMR spectrum of BMI-6, and Tg obtained from the DSC measurement are shown in Table 4. The $^1$H-NMR spectrum of BMI-6 is shown in FIG. 20.

$^1$H-NMR (CDCl$_3$/PFP=2/1) δ: 7.07 (s), 7.23 (d, J=9.4 Hz), 7.32 (d, J=7.6 Hz), 7.40 (d, J=8.3 Hz), 7.91 (m), 7.95 (d, J=8.6 Hz)

Example 13 (Synthesis of BMI-7)

Steps 1 and 2: 14.118 g of a powdery solid (Diamine-7) was obtained by carrying out the same operation as in Example 8, except for using 4,4'-dihydroxydiphenyl sulfone in place of bisphenol A, and setting the amounts of 4,4'-dihydroxydiphenyl sulfone, 4,4'-difluorobenzophenone and anhydrous potassium carbonate used at those indicated in Table 2.

Step 3: 10.724 g of BMI-7 was obtained by carrying out the same operation as in Example 8, except for using the Diamine-7 in place of Diamine-2-3, and setting the amounts of Diamine-7, maleic anhydride, acetic anhydride and sodium acetate used at those indicated in Table 3. An IR spectrum of BMI-7 is shown in FIG. 31 and a DSC measurement result thereof is shown in FIG. 39. Then, the number-average molecular weight and the degree of polymerization calculated from a GPC measurement of BMI-7, the degree of polymerization calculated from the integrated intensity ratio of signals of a $^1$H-NMR spectrum, and Tg obtained from the DSC measurement are shown in Table 4. The $^1$H-NMR spectrum of BMI-7 is shown in FIG. 21.

$^1$H-NMR (CDCl$_3$) δ: 6.88 (s), 7.11 (d, J=8.3 Hz), 7.14 (d, J=9.4 Hz), 7.24 (d, J=8.3 Hz), 7.38 (d, J=8.3 Hz), 7.85 (m), 7.94 (d, J=8.6 Hz)

Example 14 (Synthesis of BMI-8)

Steps 1 and 2: 17.041 g of a powdery solid (Diamine-8) was obtained by carrying out the same operation as in Example 8, except for using 4,4'-dihydroxydiphenyl sulfide in place of bisphenol A, and setting the amounts of 4,4'-dihydroxydiphenyl sulfide, 4,4'-difluorobenzophenone and anhydrous potassium carbonate used at those indicated in Table 2.

Step 3: 13.303 g of BMI-8 was obtained by carrying out the same operation as in Example 8, except for using the Diamine-8 in place of Diamine-2-3, and setting the amounts of Diamine-8, maleic anhydride, acetic anhydride and sodium acetate used at those indicated in Table 3. An IR spectrum of BMI-8 is shown in FIG. 32 and a DSC measurement result thereof is shown in FIG. 40. Then, the degree of polymerization calculated from the integrated intensity ratio of signals of a $^1$H-NMR spectrum of BMI-8, and Tg obtained from the DSC measurement are shown in Table 4. The $^1$H-NMR spectrum of BMI-8 is shown in FIG. 22.

$^1$H-NMR (CDCl$_3$/PFP=2/1) δ: 7.06 (s), 7.09 (d, J=9.4 Hz), 7.10 (d, J=9.4 Hz), 7.17 (m), 7.31 (m), 7.45 (d, J=8.3 Hz), 7.85 (d, J=8.3 Hz)

Example 15 (Synthesis of BMI-9)

Steps 1 and 2: 11.408 g of a powdery solid (Diamine-9) was obtained by carrying out the same operation as in Example 8, except for using a mixture of resorcinol and hydroquinone in 4:1 in molar ratio in place of bisphenol A, and setting the amounts of the mixture, 4,4'-difluorobenzophenone and anhydrous potassium carbonate used at those indicated in Table 2.

Step 3: 7.109 g of BMI-9 was obtained by carrying out the same operation as in Example 8, except for using the Diamine-9 in place of Diamine-2-3, and setting the amounts of Diamine-9, maleic anhydride, acetic anhydride and sodium acetate used at those indicated in Table 3. An IR spectrum of BMI-9 is shown in FIG. 33 and a DSC measurement result thereof is shown in FIG. 41. Then, the number-average molecular weight and the degree of polymerization calculated from a GPC measurement of BMI-9, the degree of polymerization calculated from the integrated intensity ratio of signals of a $^1$H-NMR spectrum, and Tg obtained from the DSC measurement are shown in Table 4. The $^1$H-NMR spectrum of BMI-9 is shown in FIG. 23.

$^1$H-NMR (CDCl$_3$) δ: 6.63 (s), 6.85 (s), 6.90 (d, J=7.3 Hz), 7.07 (m), 7.12 (m), 7.14 (d, J=7.9 Hz), 7.37 (d, J=9.4 Hz), 7.80 (m)

Example 16 (Synthesis of BMI-10)

Steps 1 and 2: 12.073 g of a powdery solid (Diamine-10) was obtained by carrying out the same operation as in Example 8, except for using a mixture of resorcinol and 4,4'-dihydroxybiphenyl in 4:1 in molar ratio in place of bisphenol A, and setting the amounts of the mixture, 4,4'-difluorobenzophenone and anhydrous potassium carbonate used at those indicated in Table 2.

Step 3: 8.695 g of BMI-10 was obtained by carrying out the same operation as in Example 8, except for using the Diamine-10 in place of Diamine-2-3, and setting the amounts of Diamine-10, maleic anhydride, acetic anhydride and sodium acetate used at those indicated in Table 3. An IR spectrum of BMI-10 is shown in FIG. 34 and a DSC measurement result thereof is shown in FIG. 42. Then, the number-average molecular weight and the degree of polymerization calculated from a GPC measurement of BMI-10, the degree of polymerization calculated from the integrated intensity ratio of signals of a $^1$H-NMR spectrum, and Tg obtained from the DSC measurement are shown in Table 4. The $^1$H-NMR spectrum of BMI-10 is shown in FIG. 24.

$^1$H-NMR (CDCl$_3$/PFP=2/1) δ: 6.91 (m), 6.97 (m), 7.06 (s), 7.11 (d, J=9.4 Hz), 7.13 (d, J=7.6 Hz), 7.18 (d, J=8.7 Hz), 7.20 (d, J=7.6 Hz), 7.39 (d, J=9.1 Hz), 7.47 (t, J=7.9 Hz), 7.67 (d, J=7.6 Hz), 7.86 (d, J=9.4 Hz)

Example 17 (Synthesis of BMI-1-3)

Steps 1 and 2: 12.630 g of a powdery solid (Diamine-1-4) was obtained by carrying out the same operation as in Example 8, except for setting the amounts of resorcinol, 4,4'-difluorobenzophenone and anhydrous potassium carbonate used at those indicated in Table 2.

Step 3: 10.293 g of Diamine-1-4 obtained in step 2, 1.648 g of maleic anhydride, 80 mL of N-methylpyrrolidone and 60 mL of toluene were charged in a 200-mL flask (three-necked) equipped with a stirring apparatus, an argon introducing tube and a Dean-Stark apparatus, and stirred in an argon atmosphere at room temperature for 18 hours. Thereafter, 0.107 g of p-toluenesulfonic acid (pTSA) was added; the resultant was heated to 140° C. and thereafter continuously stirred for 8 hours while toluene was refluxed to remove moisture. The resultant reaction liquid was returned to room temperature, and thereafter added to 1,500 mL of methanol to thereby obtain a powdery solid. The powdery solid was washed with methanol and water repeatedly, thereafter dried at 100° C. for 8 hours to thereby obtain 9.320 g of BMI-1-3. The number-average molecular weight and the degree of polymerization calculated from a GPC measurement of BMI-1-3, the degree of polymerization calculated from the integrated intensity ratio of signals of a $^1$H-NMR spectrum thereof, and Tg obtained from a DSC measurement thereof are shown in Table 4. Further the $^1$H-NMR spectrum of BMI-1-3 is shown in FIG. 25.

$^1$H-NMR (CDCl$_3$/PFP=2/1) δ: 6.90 (m), 6.96 (d, J=7.9 Hz), 7.05 (s), 7.10 (s), 7.12 (m), 7.13 (d, 8.3), 7.38 (d, 9.8), 7.46 (dt, J=9.3 Hz, 3.2 Hz), 7.85 (d, J=8.7 Hz)

Example 18 (Synthesis of BMI-1-4)

Steps 1 and 2: 12.639 g of a powdery solid (Diamine-1-5) was obtained by carrying out the same operation as in Example 8, except for setting the amounts of resorcinol, 4,4'-difluorobenzophenone and anhydrous potassium carbonate used at those indicated in Table 2.

Step 3: 10.293 g of Diamine-1-5 obtained in step 2, 1.648 g of maleic anhydride, 80 mL of N-methylpyrrolidone and 60 mL of toluene were charged in a 200-mL flask (three-necked) equipped with a stirring apparatus, an argon introducing tube and a Dean-Stark apparatus, and stirred in an argon atmosphere at room temperature for 18 hours. Thereafter, 0.528 g of pyridinium p-toluenesulfonate (PPTS) was added; the resultant was heated to 140° C. and thereafter continuously stirred for 6 hours while toluene was refluxed to remove moisture. The resultant reaction liquid was returned to room temperature, and thereafter added to 1,500 mL of methanol to thereby obtain a powdery solid. The powdery solid was washed with methanol and water repeatedly, thereafter dried at 100° C. for 8 hours to thereby obtain 9.801 g of BMI-1-4. The number-average molecular weight and the degree of polymerization calculated from a GPC measurement of BMI-1-4, the degree of polymerization calculated from the integrated intensity ratio of signals of a $^1$H-NMR spectrum thereof, and Tg obtained from a DSC measurement thereof are shown in Table 4. Further the $^1$H-NMR spectrum of BMI-1-4 is shown in FIG. 26.

$^1$H-NMR (CDCl$_3$) δ: 6.82 (s), 6.87 (s), 6.90 (d, J=8.7 Hz), 7.08 (d, J=7.8 Hz), 7.17 (d, J=8.7 Hz), 7.38 (m), 7.81 (d, J=7.8 Hz)

TABLE 2

|  |  | Step 1 | | | | Step 2 | |
| --- | --- | --- | --- | --- | --- | --- | --- |
|  |  | 4,4'-DFBP | Diol | | K2CO3 | 4-AP | K2CO3 |
|  |  | Amount used (g) | Kind | Amount used (g) | Amount used (g) | Amount used (g) | Amount used (g) |
| Example 7 | Diamine-1-3 | 31.443 | Resorcinol | 13.223 | 24.894 | 5.233 | 6.628 |
| Example 8 | Diamine-2-3 | 10.476 | Bisphenol A | 9.134 | 8.294 | 1.744 | 2.208 |
| Example 9 | Diamine-3 | 10.482 | 2,6-Naphthalenediol | 6.412 | 8.299 | 1.745 | 2.210 |
| Example 10 | Diamine-4 | 10.483 | 2,7-Naphthalenediol | 6.412 | 8.299 | 1.745 | 2.210 |
| Example 11 | Diamine-5 | 10.479 | 4,4'-Dihydroxydiphenyl ether | 8.092 | 8.297 | 1.744 | 2.209 |
| Example 12 | Diamine-6 | 10.484 | 4,4'-Dihydroxybenzophenone | 8.577 | 8.301 | 1.745 | 2.210 |
| Example 13 | Diamine-7 | 10.475 | 4,4'-Dihydroxydiphenyl sulfone | 10.012 | 8.293 | 1.743 | 2.208 |
| Example 14 | Diamine-8 | 10.475 | 4,4'-Dihydroxydiphenyl sulfide | 8.731 | 8.293 | 1.743 | 2.208 |
| Example 15 | Diamine-9 | 10.474 | Resorcinol Hydroquinone | 3.524 0.881 | 8.293 | 1.743 | 2.208 |
| Example 16 | Diamine-10 | 10.477 | Resorcinol 4,4'-Dihydroxybiphenyl | 3.525 1.490 | 8.295 | 1.744 | 2.209 |
| Example 17 | Diamine-1-4 | 10.476 | Resorcinol | 4.405 | 8.294 | 1.744 | 2.208 |
| Example 18 | Diamine-1-5 | 10.483 | Resorcinol | 4.408 | 8.300 | 1.745 | 2.210 |

TABLE 3

|  |  | Step 3 | | | | | |
| --- | --- | --- | --- | --- | --- | --- | --- |
|  |  | Diamine | | Maleic anhydride | Acetic anhydride | Catalyst | |
|  |  | Kind | Amount used (g) | Amount used (g) | Amount used (g) | Kind | Amount used (g) |
| Example 7 | BMI-1-2 | Diamine-1-3 | 30.878 | 4.943 | 8.576 | NaOAc | 0.689 |
| Example 8 | BMI-2-2 | Diamine-2-3 | 9.100 | 1.102 | 1.913 | NaOAc | 0.154 |
| Example 9 | BMI-3 | Diamine-3 | 11.074 | 1.560 | 2.707 | NaOAc | 0.218 |
| Example 10 | BMI-4 | Diamine-4 | 12.114 | 1.707 | 2.961 | NaOAc | 0.238 |
| Example 11 | BMI-5 | Diamine-5 | 12.648 | 1.619 | 2.809 | NaOAc | 0.226 |
| Example 12 | BMI-6 | Diamine-6 | 10.616 | 1.324 | 2.298 | NaOAc | 0.185 |
| Example 13 | BMI-7 | Diamine-7 | 11.424 | 1.324 | 2.297 | NaOAc | 0.185 |
| Example 14 | BMI-8 | Diamine-8 | 13.089 | 1.619 | 2.809 | NaOAc | 0.226 |
| Example 15 | BMI-9 | Diamine-9 | 8.271 | 1.324 | 2.297 | NaOAc | 0.185 |

TABLE 3-continued

| | | Step 3 | | | | | |
|---|---|---|---|---|---|---|---|
| | | Diamine | | Maleic anhydride | Acetic anhydride | Catalyst | |
| | | Kind | Amount used (g) | Amount used (g) | Amount used (g) | Kind | Amount used (g) |
| Example 16 | BMI-10 | Diamine-10 | 8.613 | 1.324 | 2.297 | NaOAc | 0.185 |
| Example 17 | BMI-1-3 | Diamine-1-4 | 10.293 | 1.648 | | pTSA | 0.107 |
| Example 18 | BMI-1-4 | Diamine-1-5 | 10.293 | 1.648 | | PPTS | 0.528 |

TABLE 4

| | | Number-Average Molecular Weight | Degree of Polymerization | | Tg (° C.) |
|---|---|---|---|---|---|
| | | | GPC | NMR | |
| Example 7 | BMI-1-2 | 2,230 | 5.8 | 6.0 | 115 |
| Example 8 | BMI-2-2 | 2,710 | 5.3 | 5.6 | 131 |
| Example 9 | BMI-3 | — | — | 7.3 | 145 |
| Example 10 | BMI-4 | 1,900 | 4.0 | 6.2 | 140 |
| Example 11 | BMI-5 | — | — | 7.1 | 146 |
| Example 12 | BMI-6 | — | — | 7.9 | 144 |
| Example 13 | BMI-7 | 2,850 | 5.4 | 7.4 | 155 |

The sample (0.1 g) obtained in Examples 1 to 6 and 9 to 16 each was mixed with a solvent (10 g) indicated in the following Table 5, and stirred at room temperature, 50° C. and 100° C. for 24 hours. When the powdery solid was dissolved at 50° C. or less, the sample was considered to have excellent solvent solubility (⊚); when the powdery solid was dissolved at 100° C., the sample was considered to have good solvent solubility (○); and when the powdery solid was insoluble at 100° C. the sample was considered to have poor solvent solubility (x). Here, "-" indicates that no evaluation was carried out.

TABLE 5

| | | Solubility | | | | |
|---|---|---|---|---|---|---|
| | | NMP | DMSO | Chloroform | THF | Cyclohexanone |
| Example 1 | BEI-2-1 | ⊚ | ⊚ | ⊚ | ⊚ | ⊚ |
| Example 2 | BEI-2-2 | ⊚ | ⊚ | ⊚ | ⊚ | ⊚ |
| Example 3 | BEI-1-1 | ⊚ | ⊚ | ⊚ | ⊚ | ⊚ |
| Example 4 | BEI-1-2 | ⊚ | ⊚ | ⊚ | ⊚ | ⊚ |
| Example 5 | BMI-2-1 | ⊚ | ⊚ | ⊚ | ⊚ | ⊚ |
| Example 6 | BMI-1-1 | ⊚ | ⊚ | ⊚ | ⊚ | ⊚ |
| Example 9 | BMI-3 | ○ | — | ○ | — | ○ |
| Example 10 | BMI-4 | ⊚ | — | ⊚ | — | ○ |
| Example 11 | BMI-5 | ○ | — | ○ | — | ○ |
| Example 12 | BMI-6 | ○ | — | ○ | — | ○ |
| Example 13 | BMI-7 | ⊚ | — | ⊚ | — | ⊚ |
| Example 14 | BMI-8 | ○ | — | ○ | — | ○ |
| Example 15 | BMI-9 | ⊚ | — | ⊚ | — | ⊚ |
| Example 16 | BMI-10 | ○ | — | ○ | — | ○ |

NMP: N-methyl-2-pyrrolidone
DMSO: dimethyl sulfoxide
THF: tetrahydrofuran

TABLE 4-continued

| | | Number-Average Molecular Weight | Degree of Polymerization | | Tg (° C.) |
|---|---|---|---|---|---|
| | | | GPC | NMR | |
| Example 14 | BMI-8 | — | — | 6.8 | 142 |
| Example 15 | BMI-9 | 2,360 | 5.9 | 6.7 | 116 |
| Example 16 | BMI-10 | 1,980 | 4.9 | 7.0 | 115 |
| Example 17 | BMI-1-3 | 2,530 | 6.8 | 7.1 | 112 |
| Example 18 | BMI-1-4 | 3,220 | 6.6 | 6.8 | 126 |

In Table 4, "-" indicates that no measurement was carried out.

Evaluations

Tg and the exothermic peak temperature of the samples obtained in Examples 1 to 4 were determined by the DSC measurement. The results are shown in FIG. 43. BEI-2-1 and BEI-2-2 had a Tg of about 140° C.; BEI-1-1 and BEI-1-2 had a Tg of about 120° C.; and any of BEI-2-1, BEI-2-2, BEI-1-1 and BEI-1-2 had an exothermic peak by the curing reaction observed at about 400° C.

The sample obtained in Examples 1 to 6 and 9 to 16 each was placed on a glass plate uniformly so as to have a thickness of about 0.5 mm, and heated in a muffle furnace to be cured. The muffle furnace was heated at 10° C./min from 25° C. to 371° C., and held at 371° C. for 2 hours. DSC results of cured materials obtained from the samples of Examples 1 to 6 are shown in FIG. 44; and the results of the thermogravimetric loss analysis are shown in FIG. 45. Then, the 5%-weight loss temperature ($T_{d5}$) and the 10%-weight loss temperature ($T_{d10}$) of cured materials obtained from the samples of Examples 1 to 6 and 9 to 16 are shown in Table 6.

TABLE 6

| | | TG/DTA | |
|---|---|---|---|
| | | Td5 | Td10 |
| Example 1 | BEI-2-1 | 505 | 517 |
| Example 2 | BEI-2-2 | 504 | 517 |

TABLE 6-continued

| | | TG/DTA | |
| | | Td5 | Td10 |
| --- | --- | --- | --- |
| Example 3 | BEI-1-1 | 539 | 553 |
| Example 4 | BEI-1-2 | 519 | 529 |
| Example 5 | BMI-2-1 | 501 | 525 |
| Example 6 | BMI-1-1 | 512 | 528 |
| Example 9 | BMI-3 | 479 | 531 |
| Example 10 | BMI-4 | 522 | 553 |
| Example 11 | BMI-5 | 432 | 501 |
| Example 12 | BMI-6 | 471 | 525 |
| Example 13 | BMI-7 | 450 | 500 |
| Example 14 | BMI-8 | 479 | 519 |
| Example 15 | BMI-9 | 459 | 508 |
| Example 16 | BMI-10 | 479 | 522 |

Since the DSC chart of FIG. 44 exhibits no exothermic peaks, it is clear that the compounds obtained in Examples 1 to 4 were excellent in curability (all the curable functional groups were lost by curing). From FIG. 45, $T_{d5}$ of any of cured materials of the compounds obtained in Examples 1 to 4 was more than 500° C.

The viscosity (200° C.) of BMI-1-2 was measured by a rheometer, and was 180,000 mPa·s.

BMI-1-2 was cured by a vacuum compression molding method to thereby obtain a cured material. Specifically, a mold in which BMI-1-2 had been charged was set on a press machine (30-ton manual hydraulic vacuum hot press, IMC-46E2-3 type, manufactured by Imoto Machinery Co., Ltd.), and regulated at 50° C., and heated at 20° C./min up to 220° C. under vacuum and held at the temperature for 1 hour; and thereafter, the press machine was air-cooled or water-cooled and when the mold temperature became 100° C. or less, the mold was taken out to thereby obtain a cured material. Here, the molding pressure in the temperature rise of from 50° C. to 220° C. was 70 to 80 kgf/cm², and the molding pressure when the 220° C. was held was 200 to 250 kgf/cm². Physical properties of the obtained cured material were as follows.

Density (JIS K7112A, 23° C.): 1.30 g/cm³

Glass transition temperature (measured by DSC): 150° C.

Thermal expansion coefficient (according to JIS K7197) (Tg or less): 45 ppm/° C.

Thermal expansion coefficient (according to JIS K7197) (Tg or more): 185 ppm/° C.

Relative dielectric constant (according to JIS C2138, 23° C.) (1 MHz): 3.54

Relative dielectric constant (according to ASTM D2520, 23° C.) (1 GHz): 3.18

Dielectric loss tangent (according to JIS C2138, 23° C.) (1 MHz): 0.0067

Dielectric loss tangent (according to ASTM D2520, 23° C.) (1 GHz): 0.0054

INDUSTRIAL APPLICABILITY

The curable compound according to the present invention has good solvent solubility. Further the curable compound can be quickly cured by being subjected to a heat treatment and can form a cured material having super heat resistance. Hence, the curable compound can suitably be used as encapsulants for semiconductor devices, and the like.

The invention claimed is:

1. A curable compound represented by the following formula (1):

(1)

wherein $R^1$ and $R^2$ are identical or different and each represent a curable functional group; $D^1$ and $D^2$ are 1,4-phenylene group; and L represents a divalent group represented by the following formula (1-1):

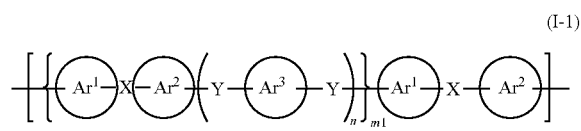

(I-1)

wherein $Ar^1$ to $Ar^3$ are identical or different and each represent a group made by eliminating two hydrogen atoms from a structural formula of an aromatic ring or a group made by eliminating two hydrogen atoms from a structural formula in which two or more aromatic rings are bound through a single bond or a linking group; X represents —CO—, —S— or —SO₂—; each Y is identical or different and represents —S—, —SO₂—, —O—, —CO—, —COO— or —CONH—; n represents an integer of 0 or more; and m1 represents 3 to 40, wherein the curable functional group is represented by the following formula (r):

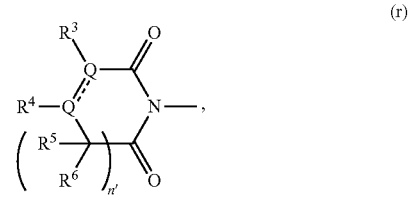

(r)

wherein the bond extending from the nitrogen atom in formula (r) is bound to $D^1$ or $D^2$, each Q represents C or CH, and Q optionally forms a double bond, n' is an integer of 0 to 3, $R^3$ to $R^6$ are identical or different, and each $R^3$ to $R^6$ represent a hydrogen atom, a saturated or unsaturated aliphatic hydrocarbon group, an aromatic hydrocarbon group, or a group in which two or more groups selected from the saturated or unsaturated aliphatic hydrocarbon group and the aromatic hydrocarbon group are bound, two groups selected from $R^3$ to $R^6$ are optionally bound to each other to form a ring with neighboring carbon atoms, and wherein the linking group represents divalent hydrocarbon groups having 1 to 5 carbon atoms or groups made by replacing one or more hydrogen atoms of the divalent hydrocarbon group having 1 to 5 carbon atoms with halogen atoms.

2. The curable compound according to claim 1, wherein $R^1$ and $R^2$ in the formula (1) are identical or different and are each a group selected from groups represented by the following formulas (r-1) to (r-6):

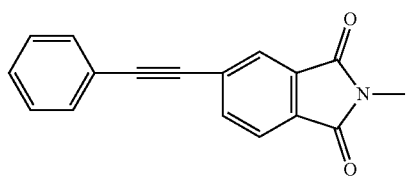
(r-1)

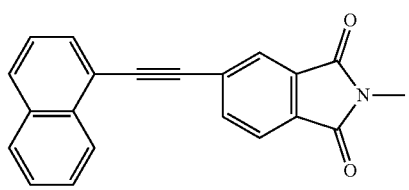
(r-2)

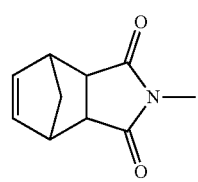
(r-3)

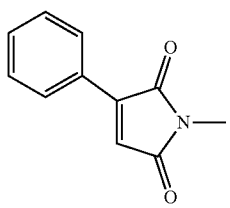
(r-4)

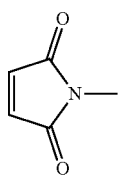
(r-5)

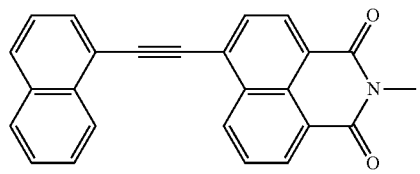
(r-6)

wherein a bond extending from a nitrogen atom in the formulas is bound to $D^1$ or $D^2$.

3. The curable compound according to claim 1, wherein $Ar^1$ to $Ar^3$ in the formula (I-1) are identical or different and are each a group made by eliminating two hydrogen atoms from a structural formula of an aromatic ring having 6 to 14 carbon atoms, or a group made by eliminating two hydrogen atoms from a structural formula in which two or more aromatic rings having 6 to 14 carbon atoms are bound through a single bond, a straight-chain or branched-chain alkylene group having 1 to 5 carbon atoms or a group made by replacing one or more hydrogen atoms of a straight-chain or branched-chain alkylene group having 1 to 5 carbon atoms with halogen atoms.

4. The curable compound according to claim 1, wherein the structure represented by the following formula (I) is a structure derived from benzophenone

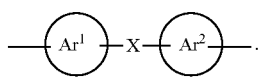
(I)

5. The curable compound according to claim 4, wherein a proportion of an amount of a structural unit derived from benzophenone to a total amount of the curable compound represented by the formula (1) is 5% by weight or more.

6. The curable compound according to claim 1, wherein the structure represented by the following formula (II) is a structure derived from at least one compound selected from hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone and bisphenol A

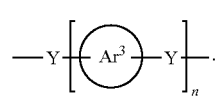
(II)

7. The curable compound according to claim 6, wherein a proportion of an amount of a structural unit derived from hydroquinone, resorcinol and bisphenol A to a total amount of the curable compound represented by the formula (1) is 5% by weight or more.

8. A curable composition comprising a curable compound according to claim 1.

9. A cured material of a curable composition according to claim 8.

10. A molding comprising a cured material according to claim 9.

11. The curable compound according to claim 1, wherein $R^1$ and $R^2$ in the formula (1) are identical or different and are each a group selected from groups represented by the following formulas (r-1) and (r-5):

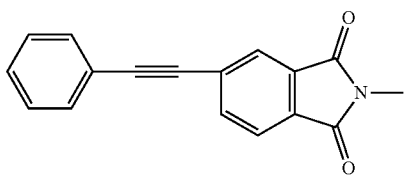
(r-1)

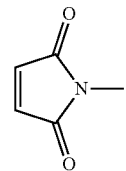
(r-5)

wherein a bond extending from a nitrogen atom in the formulas is bound to $D^1$ or $D^2$.

* * * * *